US012784918B2

(12) United States Patent
Gilbert et al.

(10) Patent No.: US 12,784,918 B2
(45) Date of Patent: Nov. 3, 2026

(54) MEDICAL DECISION SUPPORT SYSTEM WITH RULE-DRIVEN INTERVENTIONS

(71) Applicant: The Government of the United States as represented by the Secretary of the Army, Fort Detrick, MD (US)

(72) Inventors: Gary R. Gilbert, Potomac, MD (US); Jaques Reifman, New Market, MD (US); Rebecca E. Lee, Washington, DC (US); Colleen Amelia Lingley-Papadopoulos, Frederick, MD (US); Jose Salinas, San Antonio, TX (US); Tee W. Dockery, Walkersville, MD (US); Craig Andrew Fenrich, San Antonio, TX (US)

( * ) Notice: Subject to any disclaimer, the term of this patent is extended or adjusted under 35 U.S.C. 154(b) by 0 days.

(21) Appl. No.: 18/722,438

(22) PCT Filed: Dec. 21, 2022

(86) PCT No.: PCT/US2022/053736
§ 371 (c)(1),
(2) Date: Jun. 20, 2024

(87) PCT Pub. No.: WO2023/122226
PCT Pub. Date: Jun. 29, 2023

(65) Prior Publication Data

US 2025/0273349 A1 Aug. 28, 2025

Related U.S. Application Data

(60) Provisional application No. 63/292,222, filed on Dec. 21, 2021.

(51) Int. Cl.
*G16H 70/20* (2018.01)
*G16H 50/70* (2018.01)

(52) U.S. Cl.
CPC ............ *G16H 70/20* (2018.01); *G16H 50/70* (2018.01)

(58) Field of Classification Search
CPC ........ G16H 70/20; G16H 50/70; G16H 10/20; G16H 10/60; G16H 20/17; G16H 20/40; G16H 40/63; G16H 50/30; G16H 50/20
(Continued)

(56) References Cited

U.S. PATENT DOCUMENTS 7,062,251 B2 6/2006 Birkett et al.
8,880,454 B2 11/2014 Christie, IV et al.
(Continued)

FOREIGN PATENT DOCUMENTS

WO 2017037558 A1 3/2017

OTHER PUBLICATIONS

Musen et al., "Clinical Decision-support Systems", Biomedical Informatics, Chapter 22, 2014, pp. 643-674 (Year: 2014).*
(Continued)

*Primary Examiner* — Joy Chng
(74) *Attorney, Agent, or Firm* — Leigh Z. Callander

(57) ABSTRACT

A system including a main system 100 having a controller 102, a system database 104, and multiple handlers 110-116 that cooperate with a medical knowledge library 120 that may be part of the system or have one or more components external to the main system 100. The handlers 110-116 are configured to provide a communication path between the controller 102 and external systems 150-159. The medical knowledge library 120 includes a control module 122, a rules engine 124, and a serial knowledge manager 127. In at least one embodiment, the rules engine 124 is configured to analyze facts provided by a handler 118 (between the
(Continued)

controller 102 and the control module 122) to assess and provide suggested treatments to be communicated to a user through a user interface.

15 Claims, 53 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 10,431,336 | B1 | 10/2019 | Murrish et al. | |
| 10,734,115 | B1 | 8/2020 | McNair et al. | |
| 11,057,409 | B1 * | 7/2021 | Bisht | H04L 63/1441 |
| 11,978,558 | B1 | 5/2024 | Drakos | |
| 2011/0191270 | A1 * | 8/2011 | Peng | G06N 5/041 706/10 |
| 2013/0035581 | A1 | 2/2013 | Vesto | |
| 2014/0025393 | A1 | 1/2014 | Wang et al. | |
| 2015/0031321 | A1 | 1/2015 | Nakamori et al. | |
| 2015/0120321 | A1 | 4/2015 | David et al. | |
| 2015/0227710 | A1 * | 8/2015 | Pappada | G16H 70/20 705/2 |
| 2017/0116379 | A1 | 4/2017 | Scott et al. | |
| 2019/0174208 | A1 * | 6/2019 | Speicher | G06F 1/163 |
| 2022/0157423 | A1 | 5/2022 | Nanji et al. | |
| 2022/0301666 | A1 | 9/2022 | Shluzas et al. | |
| 2023/0190100 | A1 | 6/2023 | Stump | |

OTHER PUBLICATIONS

Sherimon, P.C. et al., "OntoDiabetic: An Ontology-Based Clinical Decision Support System for Diabetic Patients", Arabian Journal for Science and Engineering, Dec. 16, 2025, pp. 1145-1160 (Year: 2025).*
Yao et al., "CONFlexFlow: Integrating Flexible Clinical Pathways into Clinical Decision Support Systems using Context and Rules", Decision Support Systems, 55, No. 2, May 2013, pp. 499-515 (Year: 2013).*
European Patent Office, Extended European Search Report for EP 22912458, Nov. 11, 2025, pp. 1-9.
Demir et al., "A Next-Generation Augmented Reality Platform for Mass Casualty Incidents (MCI)", Journal of Usability Studies, Aug. 2017, pp. 193-214, vol. 12, Issue 4.
Nelson et al., "User-Centered Design and Evaluation of ARTTS: an Augmented Reality Triage Tool Suite for Mass Casualty Incidents", 2022 IEEE International Symposium on Mixed and Augmented Reality (ISMAR), Dec. 27, 2022, pp. 336-345.
U.S. Patent and Trademark Office, International Search Report for PCT/US22/53736, Jun. 15, 2023, pp. 1-5.
U.S. Patent and Trademark Office, Written Opinion for PCT/US22/53736, Jun. 15, 2023, pp. 1-12.
Musen, M.A. et al., "Clinical Decision-Support Systems", Biomedical Informatics, Chapter 22, 2014, pp. 643-674.
Sherimon, P.C. et al., "OntoDiabetic: An Ontology-Based Clinical Decision Support System for Diabetic Patients", Arabian Journal for Science and Engineering, Dec. 16, 2025, pp. 1145-1160.
Yao, W. et al., "CONFlexFlow: Integrating Flexible Clinical Pathways into Clinical Decision Support Systems using Context and Rules", Decision Support Systems, 55, No. 2, May 2013, pp. 499-515.

* cited by examiner

PROCEDURE LIST FOR INSERTING NASAPHARANGEAL AIRWAY (NPA)

SOURCE DOCUMENT:

1. Tactical Combat Casualty Care Handbook, 6 November 2020
2. TCCC Recommended Devices and Adjuncts
3. https://www.deployedmedicine.com/market/11/content/59

REQUIRED SKILL SET: Combat Lifesaver and above

SUPPLIES: Water based Lubricating gel, NPA, gloves

REASONS FOR NPA: To provide an open airway in an unconscious, breathing casualty. Do not use on patients who have sustained severe facial trauma, and disruption of the midface, nasopharynx or roof of the mouth or have signs of a basilar skull fracture.

STEP BY STEP PROCEDURE:

1. If possible/available wash hands with soap and water or hand sanitizer
2. Obtain all needed supplies
3. Assess the upper airway for visible obstruction
4. Open the airway with a head tilt or jaw thrust maneuver
5. Measure NPA for correct size
    a. Place the NPA at the tip of the nose around to the tip of the ear

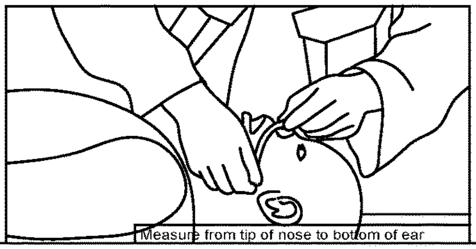

FIG. 3X

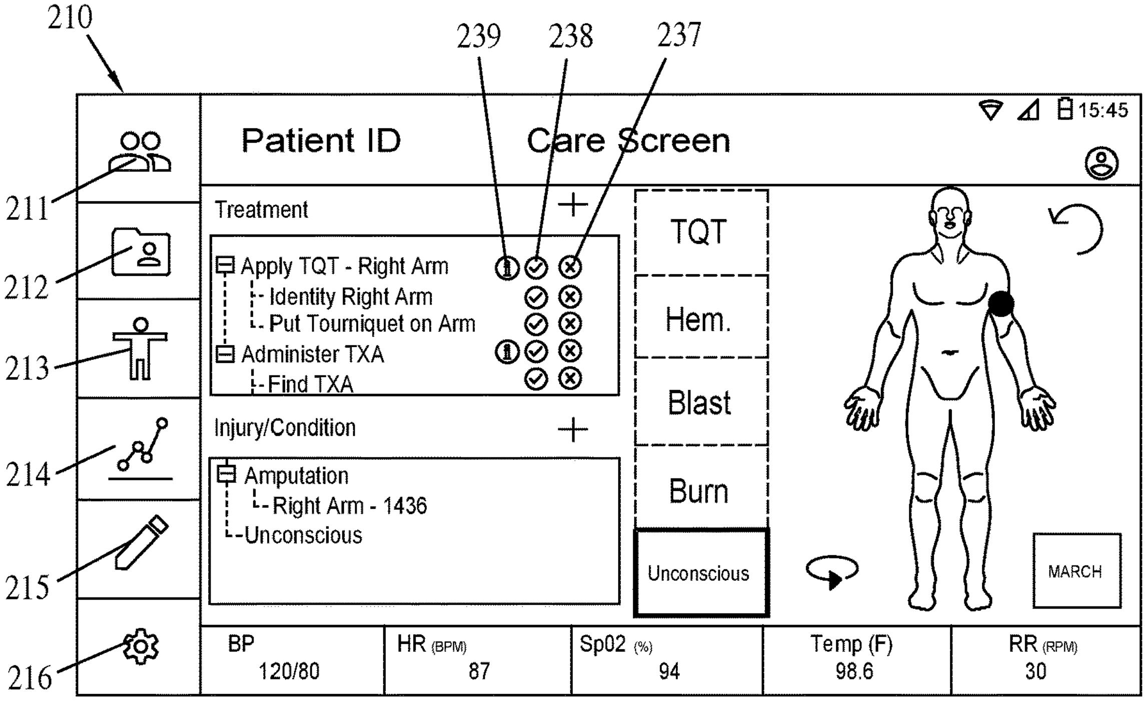

FIG. 3Y

| Time (min) | HR (bpm) | SBP (mmHg) | DBP (mmHg) | SpO2 (%) | GCS | External hemorrhage | Airway obstruction | Tension pneumothorax | Treatment | Hem. risk level | Rules Engine prompt |
|---|---|---|---|---|---|---|---|---|---|---|---|
| 0 | | | | | | | | | | | |
| 1 | 111 | | | 91 | Eye: 1<br>Verbal: 2<br>Motor: 3<br>Total: 6 | | | | | | Intubate |
| 2 | 121 | 71 | 39 | 88 | | | | | | | Tension pneumothorax? |
| 7 | 103 | 83 | 49 | 92 | | | | No | Intubation | 4 | External hemorrhage? |
| 8 | 100 | | | 100 | | No | | | | 4 | Give fluids |
| 21 | 93 | | | 96 | | | | | Fluids given | 4 | Give more fluids |
| 31 | 98 | | | 98 | | | | | Fluids given | 3 | |

FIG. 7A

| Time (min) | HR (bpm) | SBP (mmHg) | DBP (mmHg) | SpO2 (%) | GCS | Injury | External hemorrhage | Airway obstruction | Tension pneumothorax | Treatment | Hem. risk level | Rules Engine prompt |
|---|---|---|---|---|---|---|---|---|---|---|---|---|
| 1 | | | | | Total: 15 | Above knee amputation (AKA) | Yes | No | | Tourniquet | | External hemorrhage? |
| 2 | | | | | | | Yes | | | | | Apply second tourniquet |
| 5 | | | | | | | | | | Tourniquet | | External hemorrhage? |
| 6 | 133 | 110 | 67 | 97 | | | No | | | | | |
| 8 | 153 | | | 82 | | | | | | | | Tension pneumothorax? |
| 9 | 158 | 110 | 56 | 92 | | | | | No | | 4 | Give fluids |
| 22 | 156 | 104 | 74 | 100 | | | | | | Fluids given | 4 | Give more fluids |
| 32 | 140 | 112 | 67 | 100 | | | | | | Fluids given | 4 | Give more fluids |

FIG. 8A

MEDICAL DECISION SUPPORT SYSTEM WITH RULE-DRIVEN INTERVENTIONS

This patent application is a national stage application from PCT App. No. PCT/US2022/053736, filed on Dec. 21, 2022, which claims the benefit of U.S. Patent Application No. 63/292,222 filed on Dec. 21, 2021, which are hereby incorporated by reference.

A. BACKGROUND OF THE INVENTION

Even today with wide availability of communications channels, there are times when those communications channels are not readily available leaving people isolated from medical assistance as may occur in the wilderness, small islands, remote locations, or areas that have been cut-off by security conflicts, wars, civil wars, storms, wildfires, and natural phenomena such as earthquakes, volcano eruptions, landslides, blizzards, hurricanes, and tsunamis. An example of the isolation is what happens too frequently in the Caribbean, when a hurricane or an earthquake knocks out the power and communications grid leaving people isolated and dependent upon their survival skills in the short-term before assistance is able to arrive in the hours or even days after the event, particularly when there are limited ways in and out of interior mountainous areas. Isolation also occurs during military conflicts involving multi-domain operations (MDO) against peer or near peer adversaries, which can result in challenging environments where it is necessary to avoid or minimize the use of communication channels and/or results in civilians being cut-off from reliable electricity and communication networks. All of these environments may give rise to injuries and medical emergencies that require medical treatment such as prolonged casualty care (PCC), which is characterized by mass casualties, untrained individuals needing to provide care, a high ratio of casualties to individuals that can provide care, inability to evacuate rapidly, disrupted communications, and/or resource constrained cases. Although there may be first responders and medics present, their respective skill levels may vary tremendously and may be overwhelmed by the situation or in some cases they are among the injured or experiencing a medical emergency of their own leaving untrained individuals to try to treat them. In these environments, patient care and management will benefit from the use of advanced tools to improve survivability and, in the case of the military environment, maintain maximum unit combat power. In these environments where the caregiver may be stressed and/or tired over a prolonged period of care, the ability to have extra support from a system will improve outcomes by monitoring and/or alerting the caregiver to further developments for the casualty(ies) or reminding them to check the status of the casualty(ies), for example altering the care being given by adjusting a tourniquet to avoid further injuries/consequences to the casualty or checking for additional indication that further treatment is needed for an injury.

Along with skill levels of potential caregivers varying tremendously, the availability of medical supplies and even electrical power can vary and thus limit the medical treatment options beyond the caregiver's skill and knowledge level. If there is limited communication capability, then there will be no remote availability of experts to guide or assist the caregiver to consider other options. In a mass casualty situation, even in a situation where there are lots of medical supplies available, these supplies can become quickly depleted as casualties are triaged and treated. Leading to the need to adjust treatments and/or prioritize certain medical supplies for particular injuries while using other treatment approaches for other injuries.

As the casualty is transferred to a medical transport or medical facility, the ability to transfer information regarding the medical treatment and medical history since the medical event will provide for better and more expeditious medical care for that individual and improve the chances of a better outcome.

There are a variety of systems available to track vital sign information, allow entry of patient information including injuries, prepare medical records to pass along to the next level of care, and display clinical practice guidelines, but there are no decision support systems that are able to merge these disparate systems into a working decision support system to assist the caregiver to provide medical treatment to the casualty(ies) based on casualty information being used to determine the applicable clinical practice guideline(s). One example of a current system is the Battlefield Assisted Trauma Distributed Observation Kit (BATDOK) system that is able to facilitate telemedicine by providing instructions to an inexperienced medic via voice or video, but this system requires the availability of communications bandwidth, which as discussed above is not always available.

B. SUMMARY OF THE INVENTION

One solution to these problems is a system that leverages disparate data sources including: unstructured knowledge (clinical expertise and guidelines, medic (or user) observations), casualty (or patient) monitoring data, and output from other systems designed to provide relevant information based on current standards of care for PCC. In at least one embodiment, the system architecture includes a controller, a (system) database having a local database and a database controller, a serial knowledge manager, a rules engine, an optional user interface module, and handlers responsible for interacting with external devices and algorithms. In at least one implementation, clinical expertise and guidelines are converted, depending on the type of information, either into files that can be read by the system, and/or rules that can be used in the rules engine. Fielding of the system may be implemented on end user devices that will be carried by medics, first responders, medical providers, or other caregivers. Examples of end user devices include Android cell phones and tablets with their displays showing the user interface. In at least one embodiment, when the optional user interface is not present, there is a handler to communicate with an external user interface, which could be operating on the same end user device or present on a separate device.

Functional proof of concept prototypes that encompass many of the clinical decisions available to field personnel have been developed. At least one of the systems demonstrated the ability to use a rules engine to provide decision support when following the Tactical Combat Casualty care (TCCC) guidelines, Tactical Field care section. The prototypes were implemented to work on an Android phone or tablet to accept data inputs from a custom-built graphical user interface as well as blood pressure, SpO2, and heart rate from an Athena WVSM (Wireless Vital Sign Monitor) available from Athena GTX Inc., Johnston, Iowa. The Automated Processing of the Physiologic Registry for Assessment of Injury Severity (APPRAISE) algorithm, which is an Artificial Intelligent (AI) algorithm for hemorrhage risk prediction and may provide input to the system regarding a casualty's hemorrhage risk, was integrated into at least one of the prototypes. An early prototype implemented the TCCC guidelines unmodified and assumed that all supplies are available and requires user interaction.

In at least one embodiment, medical knowledge is divided into two types of information: 1) assessments, which guide the user on what to look for to identify injuries, and 2) instructions, which describe what interventions need to be done and how to perform them. The assessments and the instructions are stored in files that can be read in by the serial knowledge manager, and therefore revisable and/or updateable. In a further embodiment, the instructions are provided in an outline format, allowing the instructions to be made available in a drill-down (or expandable) style. In at least one embodiment, only the top-level instruction is shown initially to the user, but if more information is required, additional information is easily accessible by the user. The instruction files may include photos or videos and, in at least one embodiment, can be requested ad hoc if the user wants to review the information when not treating a patient. In at least one embodiment, portions of the assessment files are translatable to rules for access by the rules engine. In further embodiments, the medical knowledge is expanded to consider available inventory, the role and experience level of the user, and suggestions for prolonged field care.

In a still further embodiment, multiple prioritized suggestions will be provided to the user, since it is common for there to be multiple injuries or medical conditions requiring attention. The suggestions will be displayed in a manner which will allow the user to easily confirm which interventions or assessments have been completed. In at least one embodiment, the user interface displays vital-sign trends and/or graphs as well as alarms and alerts. In at least one embodiment, the user interface includes a button(s) for the TCCC primary assessment called MARCH (Massive hemorrhage, Airway, Respirations, Circulation, Hypothermia/head injury) to guide an inexperienced user step-by-step through the assessment process in as detailed a manner as needed.

The system architecture is designed to allow for the addition of new external components (e.g., devices and algorithms) that include input or control actions, for example to support future autonomous capabilities. In most embodiments, each added component interfaces with the system through a handler responsible for passing information between the component and the rest of the system. The original prototype specifically interfaced with both an Athena WVSM and the APPRAISE algorithm, but other external systems could be connected. In alternative embodiments, the system's open architecture supports any number of new external components such as fingerprint recognition, logistics interfaces, or AI enhanced support of different treatment modalities. Possible devices capable of carrying out actions may include a ventilator that could be controlled by the device or a robot capable of carrying out a particular intervention such as application of a tourniquet.

In at least one embodiment, the system allows for multiple casualties as well as multiple users and batch entry or downloading of roster information, including medical histories and allergies, before deployment, thereby eliminating the need to add this information in the field. In a further embodiment, the patient record will be able to be passed or otherwise transferred to another user or medic as the patient is transferred from point of injury to the next level of care, as well as to store the patient record for later upload to a de-identified database designed for the collection of data for research purposes.

In at least one embodiment, a decision support system includes a controller, a plurality of handlers, a (system) database, and a medical knowledge library (or module). In at least one embodiment, the handlers are configured to allow for communication between the controller and external systems and between the controller and the medical knowledge library. In a further embodiment, the decision support system further includes a user interface module in communication with a display to show a user interface, while, in an alternative embodiment, the user interface is provided by an external component to the decision support system. In at least one embodiment, the medical knowledge library is separate to the controller and has its own handler.

In at least one embodiment, the controller operates in a listen mode for receipt of information including data and vital-sign measurements from the handlers and the medical knowledge library to be a conduit for information from a variety of data sources including input from other systems, caregiver observations, monitoring systems, and clinical expertise and guidelines. In response to received information, the controller is configured to invoke the appropriate handler to act upon that information along with, in at least one embodiment, maintain information as to the patient state via, for example, the (system) database. Examples of patient state include, but are not limited to, a mode of injury, physical assessments, a diagnosis, an injury, vital signs, and a status of evaluations/treatments/interventions. The controller, in at least one embodiment, handles security and the login process for the design support system.

In at least one embodiment, the database is configured to support operation of the controller and may include a database controller and a local database for the storage of patient state. In further embodiments, the database controller and/or the local database will store information interface format(s) and/or routing instructions for sending/receiving information within the handlers and the controller.

In at least one method embodiment with a system that includes a controller and a medical knowledge handler to communicate with a medical knowledge library, the method includes the controller initiating an instance of the medical knowledge library for each new casualty. Once the instance of the medical knowledge library is initiated, a rules engine is initiated from a file and a serial knowledge manager is initiated to retrieve assessments and interventions from a database, which may in one embodiment be a set of XML files, to establish procedure objects that will be called by the rules engine through a control module to be sent to the medical knowledge handler based on received facts (or procedure facts asserted by the rules engine). In at least one embodiment, the control module initiates the rules engine and the serial knowledge manager. The controller upon initiation of a new medical knowledge library instance retrieves information from a connected database (e.g., a system database) to be converted into facts by the medical knowledge handler (and/or the controller) that will serve as preliminary facts on which the rules engine will act. The system then waits for the user to make a selection or provide other input through the user interface which then sends a message (fact) to the controller then to the medical knowledge library for the rules engine. Upon receiving the fact(s), the control module sends the fact to the rules engine and, in a further embodiment, followed by a run (or similar) command to cause the rules engine to act on the fact(s) in view of the fact(s) already present in the rules engine. The rules engine makes a decision as to what assessment needs to be sent to gather more information or, alternatively, the suggested treatment (or intervention) and informs the control module, for example with a procedure fact. The control module will retrieve the assessment/intervention (optionally as a procedure object) from the serial knowledge manager and send it to the medical knowledge handler for the controller and on to the user interface and optionally the system database. The user interface receives the assessment that the rules engine wishes the user to perform to gather information regarding the casualty or, alternatively, the suggested treatment to be performed. Once the user completes the assessment or intervention, a message(s) will be sent to the controller and onto the active medial knowledge library instance as a fact(s) to serve as additional input into the rules engine for further action including requesting additional information and/or suggested interventions for care of the casualty.

In a further embodiment to the previous embodiment, the initial information retrieved from the connected database includes inventory levels of medical items, which inventory levels in a further embodiment are decremented as medical items are used with new inventory fact for that medical item being provided to all active instances.

Further to any of the method embodiments above, examples of suggested treatments (or interventions) include, but are not limited to, applying a tourniquet, a bandage, or a wound dressing to stop a hemorrhage, tightening, replacing, or removing a tourniquet, administrating a medication, an intravenous solution, a blood transfusion, or a beverage, inserting an airway and/or a chest tube, performing a cricothyroidotomy, providing oxygen, performing rescue breathing, a jaw thrust, or head tilt, placing the casualty in rescue position, monitoring temperature or oxygen level, applying or burping a chest seal, performing a needle decompression, attaching a splint or other immobilization device to secure a fracture and/or a sprain, and covering at least a portion of the casualty with a blanket or other protective covering.

Based on this disclosure and the attached claims, a person having ordinary skill in the art should appreciate that the dependent claims may be arranged in multiple levels of multiple dependent structures other than when the dependent claim is an alternative to another dependent claim preventing logical dependency from each other. Based on this disclosure, it should be appreciated that the various user interfaces depicted in the figures may be illustrated without the presence of casualty and/or user information.

C. BRIEF DESCRIPTION OF THE DRAWINGS

The following drawings form part of the present specification and are included to further demonstrate certain embodiments of the present invention. The invention may be better understood by reference to one or more of these figures in combination with the detailed description of specific embodiments presented herein.

D. DETAILED DESCRIPTION

Figure 1A:
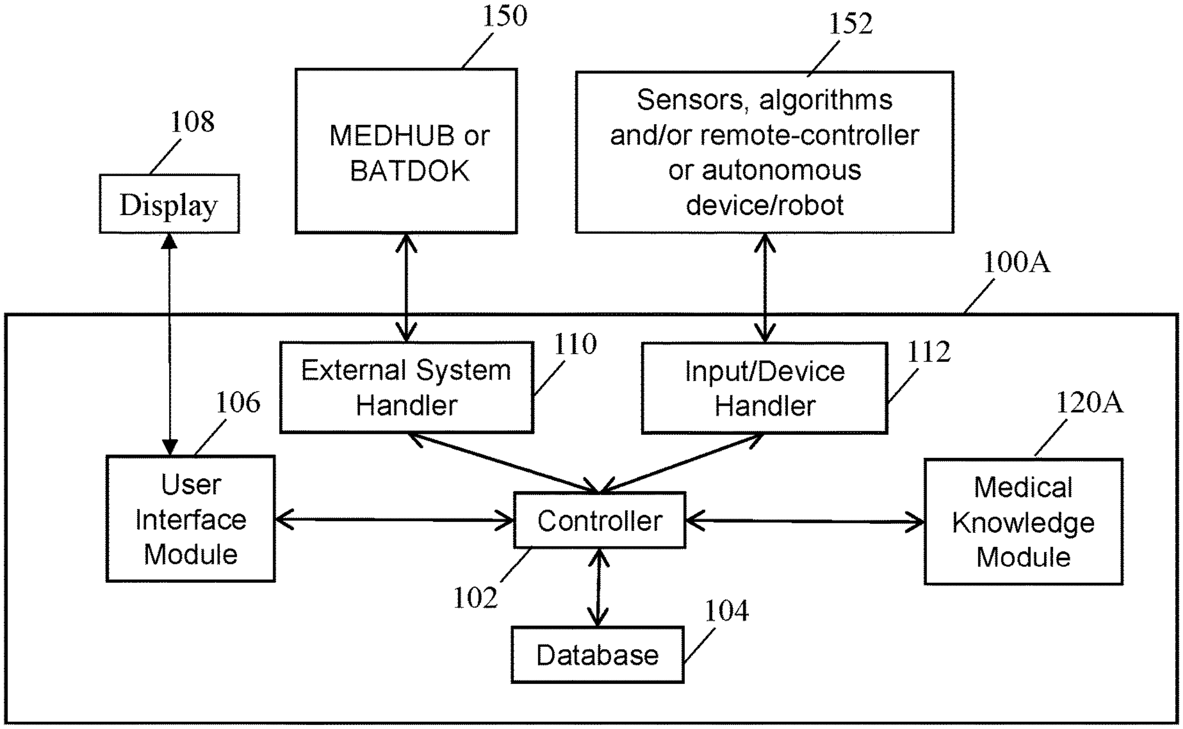
FIGS. 1A-1G illustrate block diagrams according to different embodiments of the invention.
Figure 1B:
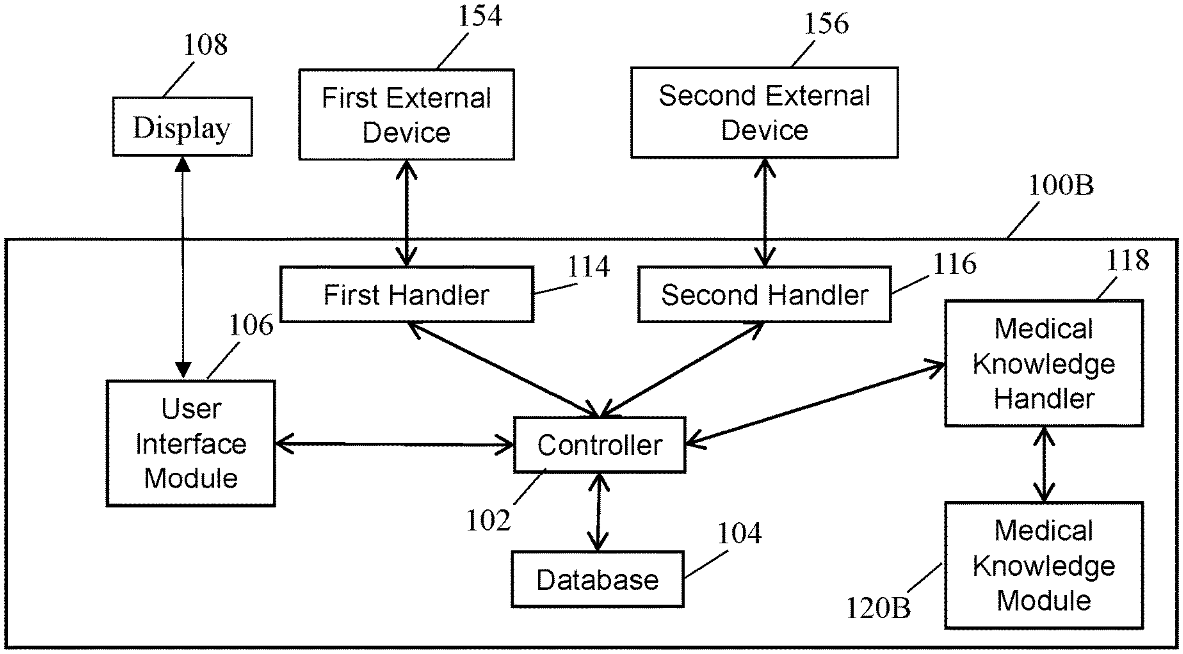
Figure 1C:
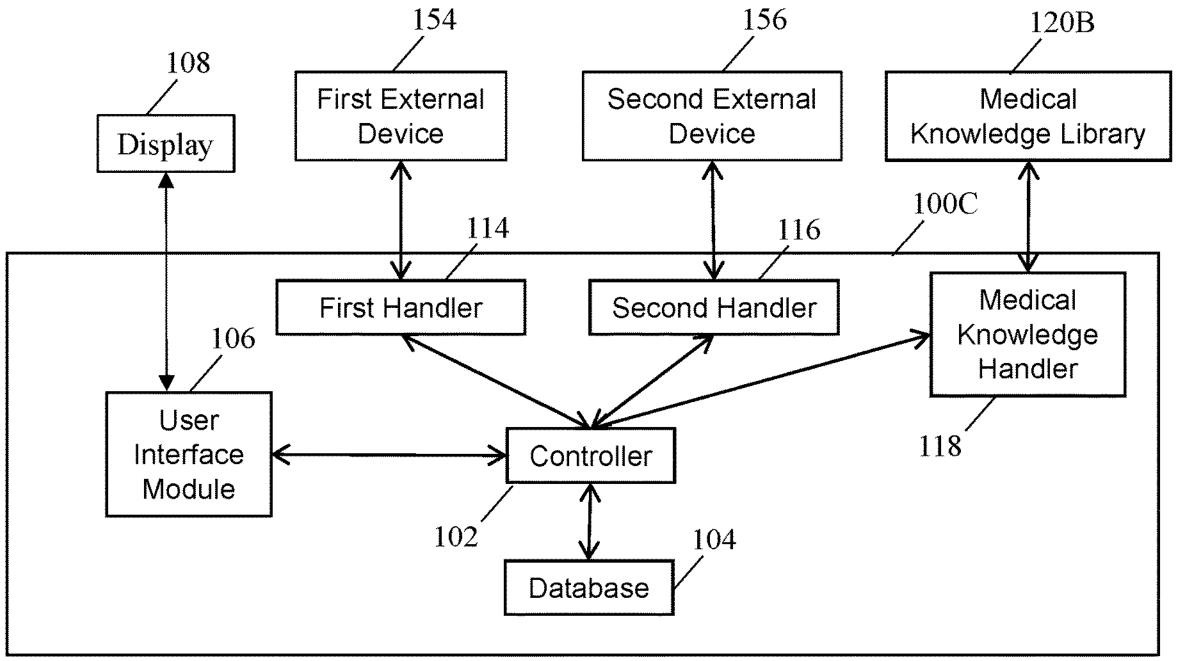
Figure 1D:
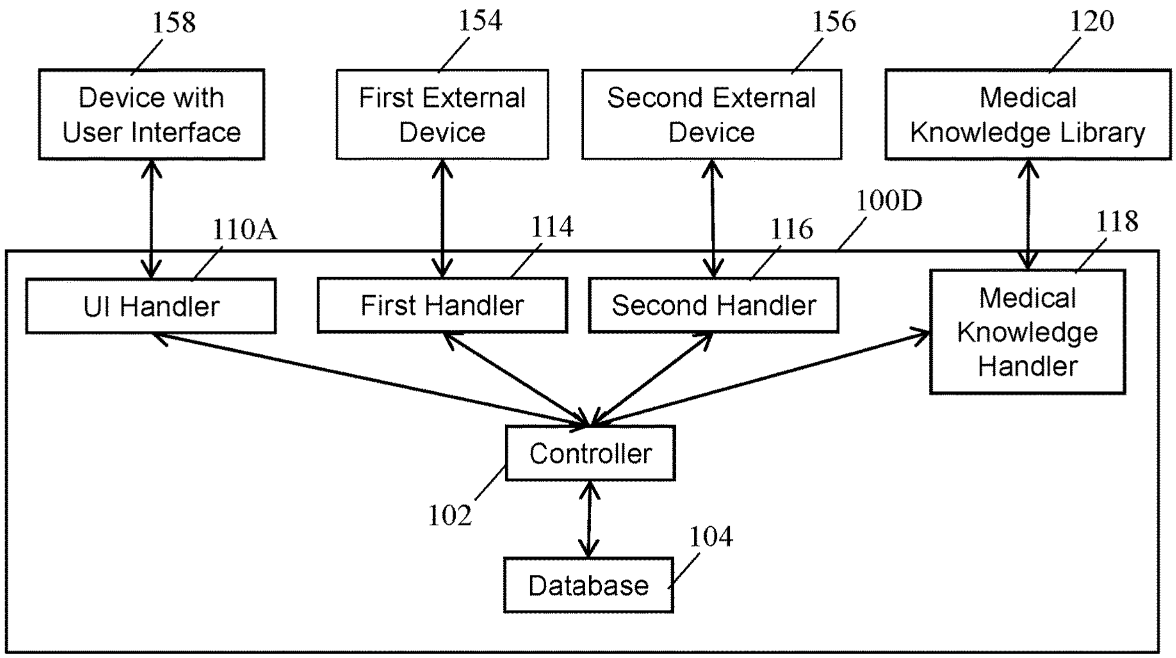
Figure 1E:
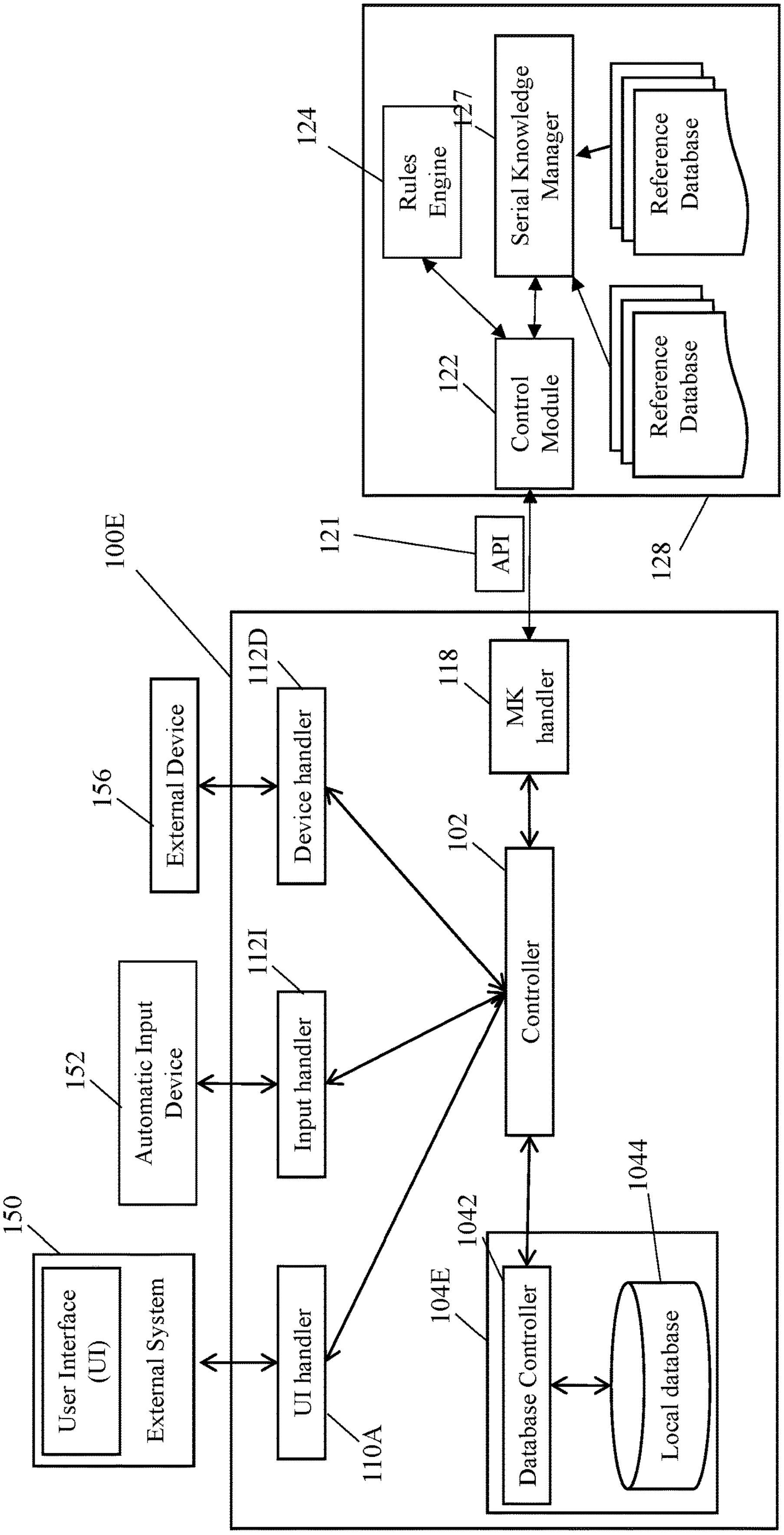
Figure 1F:
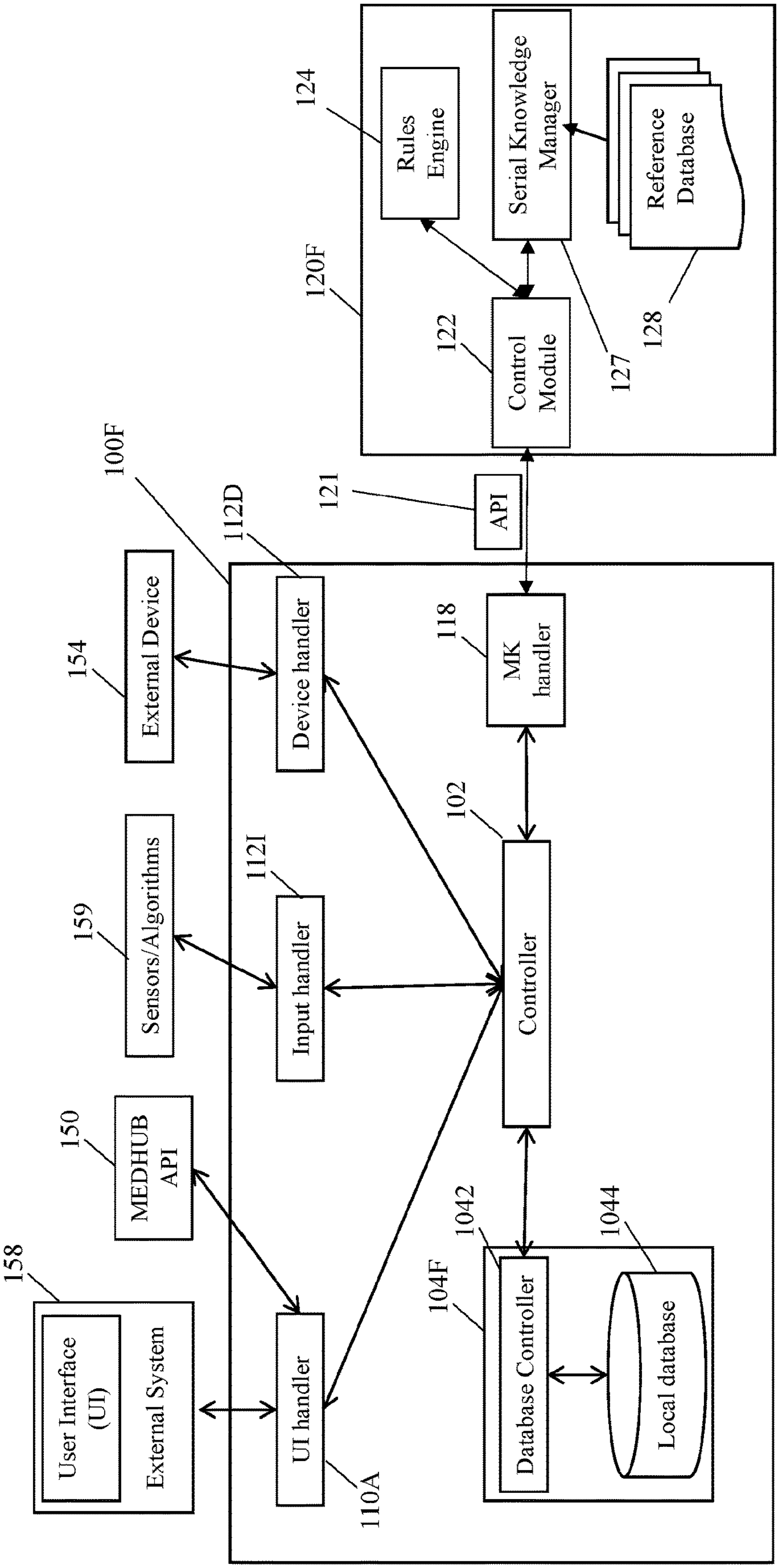
Figure 1G:
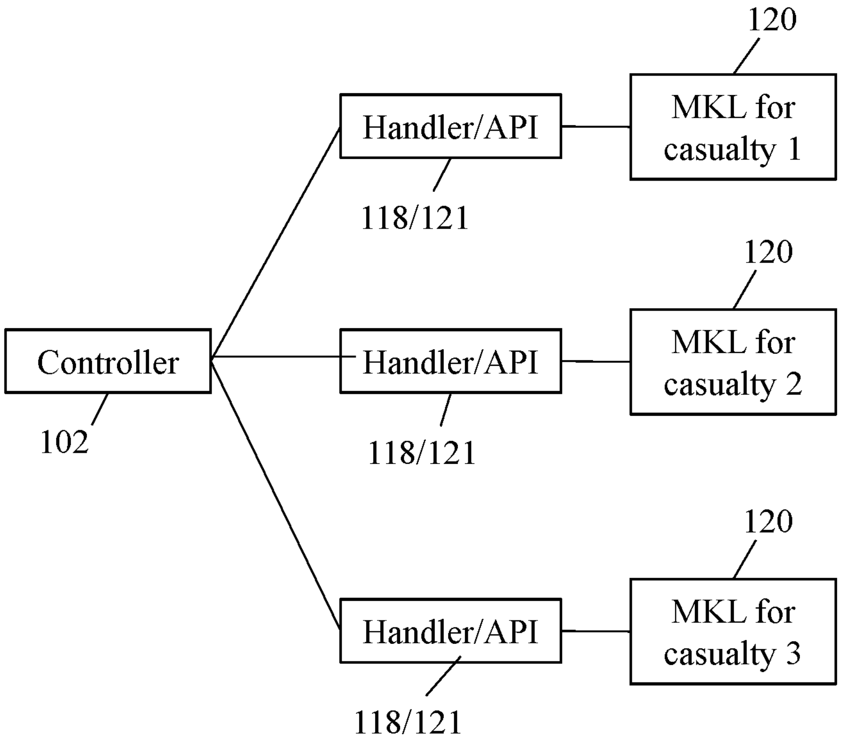

FIGS. 1A-1F illustrate different implementations of a decision support or hub 100A-100E (collectively main system 100) and external components that, for example, can be used to provide prolonged care to casualty(ies), which for the purposes of this disclosure includes individuals who are assessed using the disclosed system to determine if the individual is injured and/or should receive suggested treatments. In at least one embodiment, the system operates on a processor(s) configured to run code to provide the described functionality in this disclosure with an optional touchscreen display to show the user interface. FIGS. 1A and 1B illustrate alternative high-level views of a decision support system 100A, 100B including a controller 102, multiple handlers 110-116 (to connect to external devices 150-156), a (system) database 104, a medical knowledge module 120A, and an optional user interface module 106 to interface with a display 108. FIG. 1B illustrates the medical knowledge handler 118 being separate from the medical knowledge module 120. FIGS. 1C and 1D illustrate alternative embodiments of a hub (or front end) system 100C, 100D where the active medical knowledge library 120 is external to the hub system 100C, 100D and is an external library and not a module. FIG. 1D illustrates an alternative embodiment where the user interface is present on an external device (or application) 158 and an UI handler 110A is present. FIGS. 1E and 1F illustrate more detailed embodiments of a system with hub systems 100E, 100F, respectively, medical knowledge libraries 120E, 120F, respectively, and optional external devices/systems. In at least one embodiment when configured to handle multiple casualties, the system will have multiple instances of the medical knowledge library 120 (represents variants 120A-120F) running with each casualty having their own respective instance as illustrated in FIG. 1G, which illustrates an example where three medical knowledge libraries 120 are in communication through respective APIs 121 and/or medical knowledge handlers 118 with the controller 102 with remaining components omitted from the figure for simplicity purposes. Based on this disclosure, it should be understood any number of medical knowledge library instances may be running simultaneously with each other. In FIGS. 1A-1E, the controller 102 provides the hub through which information including data flows through the system and between the connected components 150-158, the handlers 110-118, the (system) database 104, the medical knowledge library or module 120, and the optional user interface module 106. FIGS. 2A-5G illustrate example interfaces, which in at least one embodiment include preset buttons to trigger a message to be sent to the medical knowledge library for a particular action to occur (or fact to be asserted/considered) and areas into which information provided by the medical knowledge library 120 is populated (e.g., a textual window 230T and a vital-signs footer 250). FIGS. 6A-9 provide examples of how information flows through the system. In at least one alternative embodiment, the user interface is provided by a component external to the hub system 100D, 100F, for example as illustrated in FIGS. 1D and 1F through an UI handler 110A and an external system 150, 158. For the purposes of this disclosure, a user of the system includes an individual directly using the system and/or a first individual acting in response to output of and providing input for the system where a second individual is directly using the system as a relay for the first individual.

Each connected handler 110-116 provides an interface for the controller 102 to an external system 150-159 (i.e., external to the system 100 and not always on a separate device from the decision support main system 100) with examples of the external system including medical records systems; vital-sign monitors 157 or 159; fitness tracking devices or other wearable devices; artificial intelligence (AI) systems; and/or robotic/motorized care systems/equipment such as a ventilator, a mechanical tourniquet, or an evacuation drone. In at least one embodiment, the external systems are separate from the device on which the main system 100 is resident, while in other embodiments the AI systems, the user interface, and the medical knowledge library 120 may be present on the same device (or hosting device) as the controller 102. When the external system is a separate device, the external system in many embodiments will typically communicate with the appropriate handler 110-116 through a wireless connection through the hosting device on which the handler 110-116 resides while in an alternative embodiment the external system is connected with a wire to the device on which the handler 110-116 resides including some external systems being connected via wire and others wireless. The handler 110-116 provides the information conduit through which information can be provided by the external system 150-159 and/or sent to the external system 150-159 by the controller 102. In at least one embodiment, the handler 110-116 translates the syntax and message structure of the information being shared to conform to the external system's syntax and/or protocols and the syntax used by the decision support main system 100 because many vital-sign monitors have proprietary syntaxes for their data outputs. The handler 110-116 will convert and/or separate messages and/or data stream into the message syntax for the intended recipient. An example of how the syntax for the main system 100 is structured is discussed later in this disclosure. In at least one embodiment, the handlers 110-116 operate in a message listener state with the controller 102 and optionally the external system 150-159 in communication with that handler 110-116.

In at least one embodiment, the (system) database 104 stores information regarding individuals that are associated with or become associated with the decision support main system 100, for example a unit roster. When the decision support main system 100 is being used in a triage or ad hoc environment where the database 104 has not been prepopulated, the decision support main system 100 allows for a new entry of the casualty (or patient) through, for example, the optional interface module 106 (e.g., FIGS. 1A-1C) or an interface in an external system (e.g., FIG. 1D). In other circumstances, the database 104 may be prepopulated with information about individuals operating in the same unit (or group) as the user of the decision support main system 100, for example residents of an area impacted by a natural disaster, a wild land firefighter crew such as a hotshot crew, a search and rescue unit, a military unit, a remote research site staff, a regular hiking group, an outdoor adventure group, a safari group, a mountaineering group, or other groups that have the possibility of losing or being out of contact with communications networks and the potential to have an injury and/or a medical emergency. In at least one embodiment, prepopulated information and/or facts can be sent to the medical knowledge library 120 to provide faster instructions and/or guidance with fewer inquiries regarding the casualty being treated and/or evaluated than with ad hoc use of the system. Allowing for faster treatment (or intervention) options will lead to less frustration, delay, and opportunity for confusing the user particularly when the user is not a medic or other medical professional experienced with the diagnosis and/or treatment of the injury(ies) of the casualty (or individual) being evaluated. It has been found that for many situations the ad hoc use without the benefit of an individual's medical history should be sufficient to facilitate any assessment and/or treatment of the individual. In another situation, the database 104 will include a list of names (or roster) for the unit (or group) to allow for a quicker start to any assessment by providing information to be converted into initial facts for the medical knowledge module 120. In at least one embodiment, the database 104 includes a database controller 1042 and a local database 1044 as illustrated in FIGS. 1E and 1F, which may be included as part of the databases 104 in FIGS. 1A-1D.

In at least one embodiment, the medical knowledge library 120 communicates with the controller 102 or other front end systems through an optional API 121 in communication with a medical knowledge handler 118, which in one embodiment is grouped with the other handlers 150-159. In at least one embodiment, the medical knowledge library 120 includes a control module 122 connected to a rules engine 124 and a serial knowledge manager 127 that together receive, request, and provide medical information. The control module 122 may serve the role of the constructor in a CLIPS implementation and initiate the rules engine 124 and the serial knowledge manager 127. In at least one embodiment as illustrated, for example, in FIGS. 1C-1E, the medical knowledge library 120 is external to the front end system 100C-100E. In at least one embodiment, the medical knowledge library 120 receives information that is categorized as facts by the medical knowledge handler 118 for processing by the rules engine 124 to provide treatment support for at least one casualty. In a further embodiment, an individual instance of the medical knowledge module 120 is used per casualty. Based on the received facts, the medical knowledge library 120 requests additional medical information and/or provides intervention instructions to the user. In at least one embodiment, the medical knowledge library 120 includes an internal facts repository (or listing) that is configured to store and assist in tracking facts and other information for one or more casualties. In a further embodiment, the facts repository is associated with one casualty that the medical knowledge library 120 is running as an instance. In a further embodiment, the medical knowledge library 120 will use an identifier, for example the casualty's name (or part of the name) and/or number, to identify the appropriate casualty information to consider in the rules engine 124.

In at least one embodiment, the level of instructions is determined based on the skill level of the user, and in a further embodiment, the instructions can be expanded by the user to allow the user to receive more detailed instructional steps for performing a particular evaluation and/or treatment (or intervention). In a yet further embodiment, the user interface may be switched to a button layout for more experienced users to facilitate data collection before suggesting additional treatment options. In at least one embodiment, the user will indicate via the user interface which treatments and/or treatment sub-steps have been performed with the main system 100 with the medical knowledge library 120 tracking when the step was performed and in a further embodiment, setting reminders or starting timers for follow-up on a given treatment as discussed later.

In at least one embodiment, the medical knowledge library 120 tracks received updated medical information to provide warnings to the user if a material change in a casualty's vital-signs has occurred that requires further evaluation and/or treatment. In a further embodiment, the medical knowledge library 120 will provide a prioritized listing and/or use color coding if there are multiple casualties requiring further evaluation and/or treatment to assist the user in prioritizing what to do particularly when the user may not be a medically trained person and less aware of the need for continued monitoring. In an embodiment with multiple medical knowledge library 120 instances, the controller 102 will provide prioritized listings based on preset priority levels as provided by the serial knowledge manager 127. Depending upon the situation, the tracking and use of timers/alarms/reminders will help the user to monitor multiple casualties and provide assistance particularly with the passage of time and potential need for sleep by the user and/or the stress/chaos of the environment in which the group/unit is.

FIGS. 2A-5G illustrate examples of user interfaces that may be present in an external module 150, 158 (e.g., FIGS. 1D-1F) or displayed by the optional user interface module 106 (e.g., FIGS. 1A-1C), for example through a display 108. Based on this disclosure, a person having ordinary skill in the art will appreciate that the arrangement and contents of the example interfaces could be different than that illustrated. In at least one embodiment, the user interface includes icons that will trigger the creation of a message (or a fact) to be delivered to the medical knowledge library 120. FIGS. 2A-2L and 3D-3W include a static icon/button menu 210, an information (or care) screen 230 that can be subdivided between a textual section 230T and a homunculus section 240, and a vital-signs footer 250 that will be discussed later in this disclosure. FIG. 3D illustrates the interface framework with some vital-sign measurements populated as an example of the vital-signs footer 250 below the care window 230. FIGS. 3I-3Q illustrate a care window 230 showing the textual screen 230T interface that includes procedures (or treatment options) and a homunculus section 240 above the vital-signs footer 250. FIGS. 4A-5G illustrate alternative user interfaces. A common trait amongst many of the illustrated interface embodiments of FIGS. 2A-4D is the use of color to provide visual cues to the user, and example colors include red, yellow, and green. Examples of where color may be present is in the virtual ward screen 260 (e.g., FIGS. 3E and 3F) and the care window 230 (e.g., footer in FIG. 3I and FIGS. 3Y, 4B, and 4C). In at least one embodiment, the order of questions to answer or treatments to be performed are prioritized and/or in a larger font size. In at least one embodiment, as questions are answered or treatments completed, the question/treatment is moved to a completed section 230C. In at least one further embodiment to the user interface embodiments with M A R C H icons (or tabs) 231, 231A or expandable listings are present, the user may skip assessment categories and proceed to the questions/treatments for a particular element of the MARCH assessment. In an alternative embodiment, the system is configured to display in the user interface a set of assessment icons and corresponding assessment steps based on the contents of a database associated with the serial knowledge manager 127 such as the reference database 128 or the assessment questions database 128A. For the purposes of the medical knowledge library 120, database includes a data repository, a file repository, a collection of files (e.g., XML or HTML files), or a directory. Other examples of casualty assessments are Airway, Breathing, Circulation (ABC); Pain, Antibiotics, Wounds, Splinting (PAWS); and burn assessments. Based on this disclosure, a person having ordinary skill in the art should appreciate that the various discussions of MARCH may be replaced by a different assessment illustrating the flexibility of the system architecture to allow for the use of other assessments by changing the content files store in one of these databases. In at least one alternative embodiment, the medical knowledge instance selects a rules engine and a serial knowledge manager to initiate based on the requested assessment approach from the user. In at least one embodiment, the assessment questions database 128A includes one or more XML files.

Turning back to the illustrated embodiment of FIG. 1B, the controller 102 is the hub of the main system 100 through which all information passes between the handlers 110-118 and the database 104. Depending on the particular implementation as illustrated in the figures, the main system 100 may be configured to have a user interface handler 110A and an input and/or device handler(s) 110-116. FIG. 1E also illustrates the medical knowledge library 120 connect through an optional application programming interface (API) 121 that is connected to a handler 118, which connects with the controller 102. Each handler 110-116 shares the common ability to handle information to and from the external system for the controller 102. In a further embodiment, the handlers 110-118 are APIs. Examples of the information handling include requests for data, transmitting data, prioritizing communications, and relaying capabilities of the external system. Illustrative examples of information flows and case studies will be discussed later in connection with FIGS. 6A-6F, 7B-7G, 8B-8I, and 9.

Figure 6A:
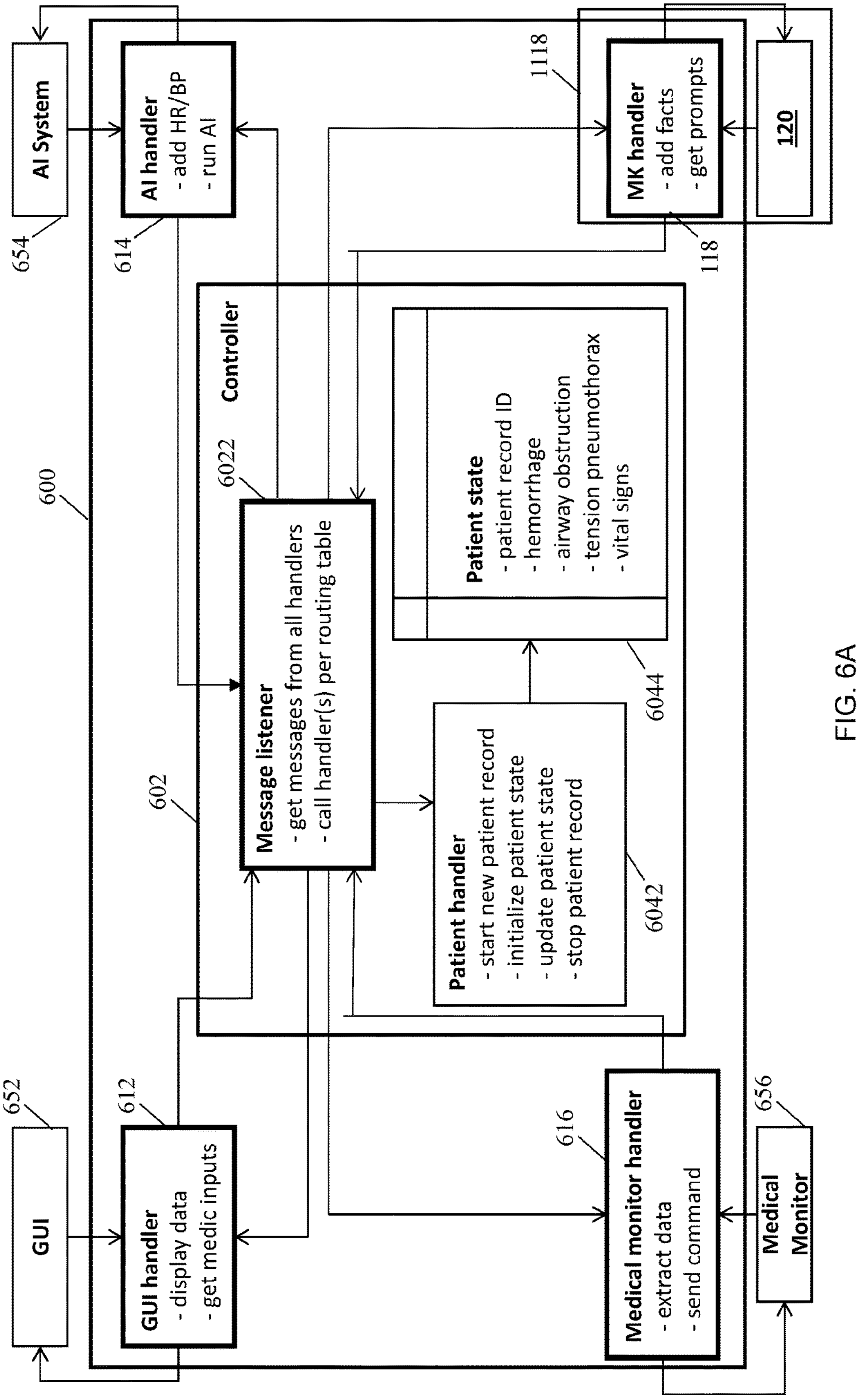
FIGS. 6A-6F illustrate information flows according to at least one embodiment of the invention.
Figure 6B:
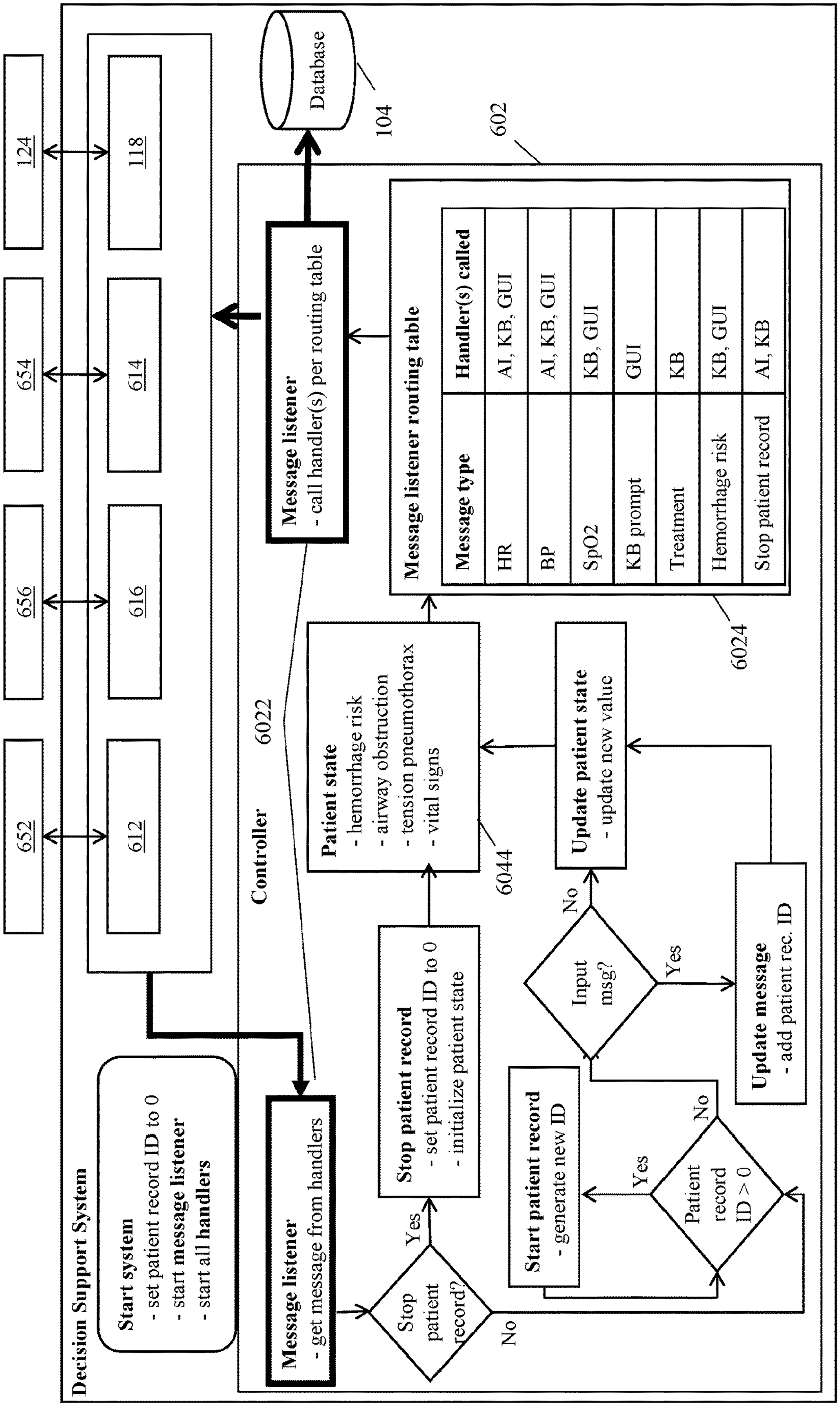

The controller 102, in at least one embodiment, listens for information being passed by the handlers 110-118 or the database 104 to be routed to the proper recipient component(s) as some information is relevant for multiple components in the system, for example as illustrated in the Message listener routing table 602 of FIG. 6B. See also FIGS. 7B-7G and 8B-8I. In at least one embodiment, this is accomplished in substantially real-time, and in a further embodiment, it is implemented by the controller 102 actively polling one or more active handlers 110-118 for information or checking a receiving buffer for information from the active handlers 110-118 being present. The controller 102 in conjunction with the database 104 maintains the patient state for each casualty and in some embodiments the other individuals in the user's group/unit. In terms of a casualty, the mode of injury, physical assessments, the diagnosis, the injury, vital signs, and the results and statuses of any evaluations, treatments, and/or interventions are maintained. As discussed previously in connection with a multi-casualty environment, the medical knowledge library 120 will store some or all of this information as facts where each casualty will have their own respective medical knowledge library 120 instance operating in conjunction with the controller 102.

In at least one embodiment, the controller 102 also tracks which handlers 110-116 are in use and the capabilities and data requirements (e.g., desired data and form of the data) for the external systems in communication with the respective handlers. In at least one embodiment, the handler information is maintained in the database 104, a handler specific database, a look-up table, or an XML file to facilitate the routing of information through the controller. In at least one embodiment, the handler information is modifiable to include current information as handlers are connected and disconnected to the system and/or particular casualties (or individuals), which in at least one embodiment allows for efficient use of monitoring equipment with the more injured individuals and/or individuals who are at greater risk of their condition worsening. In an example where there is a robot or algorithm system connected, the controller 102 could track, for instance, that the robot is only interested in facts that say tourniquet=apply, or it could say the algorithm system is only interested in SpO2, heart rate, and blood pressure values. This adaptability will allow the controller 102 to connect to different handlers, in part, because the new handler will translate the messages between the controller 102 and the device/system that is in communication with the handler. In a further embodiment to these embodiments, the controller 102 activates and deactivates handlers as external systems are connected or disconnected to the device on which the front end main system 100 resides and/or as the controller 102 receives input from the user as to the connection status of the external devices which in a further embodiment allows the user to adjust the attached external systems, for example to conserve battery life of the device or external systems. In a still further or alternative embodiment, the controller 102 include an API to the device operating system that is configured to communicate to the controller 102 when an external system is connected or disconnected. In a still further embodiment, the controller 102 in response to a connection communication will send an inquiry to the user interface inquiring of the user whether to start the respective handler and/or identify which casualty is attached to the external system (if applicable).

Figure 3A:
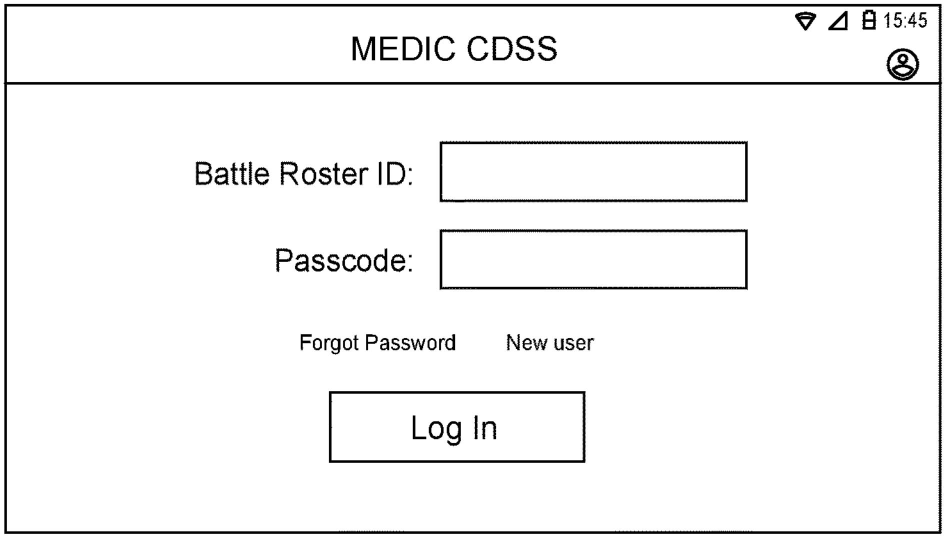
FIGS. 3A-3Y illustrate a series of user interfaces according to at least one embodiment of the invention.
Figure 3B:
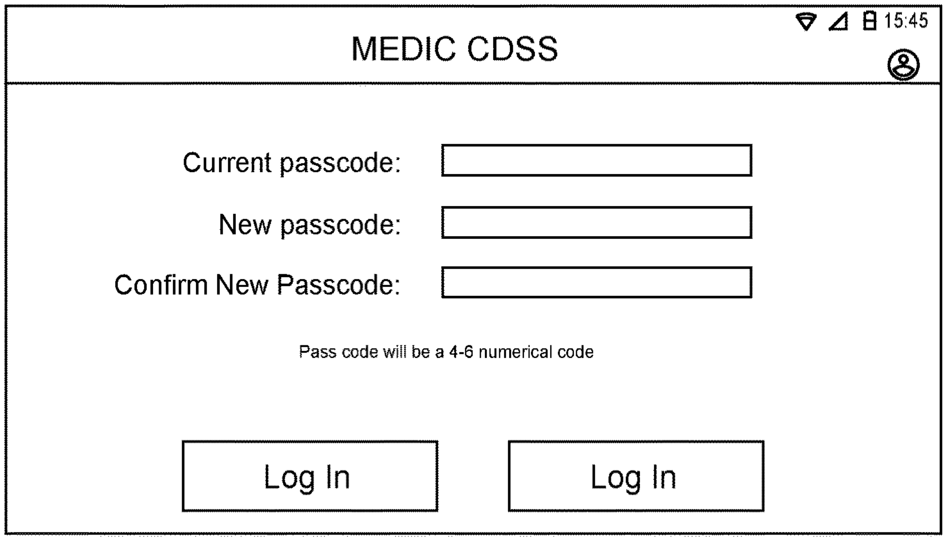
Figure 3C:
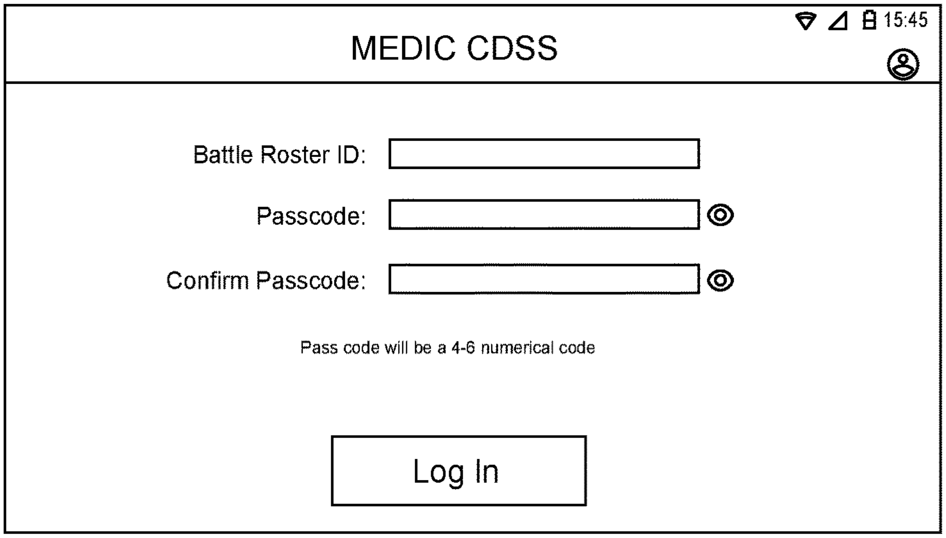

As with many systems, the controller 102 can be responsible for handling security, data encryption, the login process, and data upload/download, and in a further embodiment the controller performs these activities in conjunction with the user interface, for example, such as those illustrated in FIGS. 3A-3C. In at least one further embodiment, the controller 102 handles the security and the login for the user(s), which as mentioned later may include fingerprint and/or facial recognition, but could be other login approaches and authentications.

In at least one embodiment, the system database 104E as illustrated in FIGS. 1E and 1F includes a database controller 1042 and a local database 1044. The system database 104E may be used as the database 104 in FIGS. 1A-1D. The database controller 1042 handles the movement of information between the controller 102 and the local database 1044, which stores the information collected by the front end system 100E, 100F and any preloaded unit/group information, for example a roster. In at least one embodiment, all of the information collected by the front end system 100E, 100F is stored in the local database 104E and where applicable as facts in the medical knowledge library 120. In at least one embodiment, the stored information is timestamped and in a further embodiment the source of the information is identified. The information may include the information queries and the suggested procedures sent from the medical knowledge library 120. The database controller 1042 formats the information going between the controller 102 and the local database 1044 and acts as the database controller for the local database 1044. In at least one embodiment, the stored information in the local database 1044 is encrypted. In at least one embodiment, the local database 1044 resides in memory or other data storage of the hosting device main system 100.

In at least one embodiment, the local database 1044 is prepopulated with user information, individuals' information for potential casualties, connected systems/devices, and supply information beforehand but allows the user to add new information as needed. In a further embodiment, the handler database is included in the local database 1044. The prepopulated information may be received, for example, in a streaming data feed if communications are available as well as being stored and uploaded prior to use if communications are expected not to be available. Examples of potential user information include demographic information about the user as well as information about the inventory available to them, their experience level and their login credentials. Information about individuals may include, for example, personal and demographic information about all unit/group members. Examples of device information include identification (ID) numbers and when appropriate capabilities, status, and data requirements. The local database 1044 may also include casualty information such as personal and demographic information about the casualty as well as any information about the state of that patient or evaluations or interventions started/completed. In at least one embodiment the local database 1044 is a relational database. In a further embodiment, the relational database links the individuals' information to the patient and/or the user information as applicable.

In at least one embodiment, the controller 102 (or the database controller 1042) will timestamp each piece of information provided to the local database 1044 and indicate its source. In at least one embodiment, the timestamp may be in addition to or omitted when the information includes a timestamp. See, e.g., FIG. 6C ("Extract vital signs" box). In at least one further embodiment, the database controller 1042 (or the controller 102) will normalize the vital-sign measurements into predetermined units. In at least one embodiment, only the controller 102 will directly access the local database 1044 via the database controller 1042 with the controller 102 able to upload or download data to/from the cloud and received from or sent to the other modules.

FIG. 1E illustrates the medical knowledge library 120E being external to the front end system 100E although in at least one embodiment both the front end system 100 and the medical knowledge library 120E are present on the same device although they may run on separate processors, and in a further embodiment the medical knowledge library 120E or part of it is part of the front end system 100A as illustrated, for example, in FIGS. 1A-1B. Based on this disclosure, the different illustrated medical knowledge libraries 120A, 120B, 120E, 120F may be interchanged with each other in FIGS. 1A-ID. The illustrated medical knowledge handler 118 may have a similar configuration as other handlers for handling data and/or information going between the controller and the medical knowledge library 120B or 120E, or, alternatively, it is included as part of the medical knowledge library, for example in FIG. 1A. In a further embodiment, the medical knowledge handler 118 translates the received messages from the controller 102 having information into facts to be used by the medical knowledge library 120 and vice versa.

In at least one embodiment, the medical knowledge handler 118 will convert the message received into a fact by parsing and converting the parts of the message into a fact(s) for the rules engine 124. For example, if the message includes a heart rate for the individual, then the handler 118 will convert this into a vital-sign field with heart rate and a second field with the value of the heart rate. In an alternative embodiment, the individual will be identified so that the medical knowledge library 120, may use previously received/determined facts or, in an alternative embodiment, request retrieval of existing information from the database 104 by the controller 102. In an alternative embodiment, the handler 118 will use a case statement or a look-up table as part of the controller message conversion into a fact for the rules engine 124.

In at least one embodiment, the controller message is in the form of fact received from the user interface when the assessment or the treatment instructions coding provided by the medical knowledge library 120 includes a conditional fact to be triggered based on a selection or an entry by the user. In this situation, the handler 118 will pass the fact to the medical knowledge library 120 for the rules engine 124 and also onto the optional facts repository (depending on the embodiment) and convert the fact into a message to be sent to the system database 104 and possibly other handlers 110-116 depending on the message content (or type) as determined by the controller 102. The created message will enable the system database 104 to store the fact in a syntax for the database structure.

The illustrated medical knowledge library 120E, 120F includes a controller module 122, a rules engine 124, a serial knowledge manager 127, and a database(s) (e.g., an assessments database 128A, an interventions database 128B, and/or a reference database 128). In a further embodiment, the rules engine 124 will include a facts repository (or list). In at least one embodiment, medical knowledge is resident in the rules engine 124. In at least one embodiment, the medical knowledge library 120 will use a priority handling structure that tags any evaluations and treatments with a priority level that can be used by other components to display the evaluations and treatments in a priority order and in some embodiments color code them based on their priority, for example red, yellow, and green. Examples of priority levels code be numeric, for example from 0 to 5, 1 to 5, 0 to 10, or 1 to 10. In a further embodiment, the priority level is preset and included in the reference database. In an alternative embodiment, the priority level is set based on the salience for the rule that triggered the assessment question and/or the intervention.

Figure 6C:
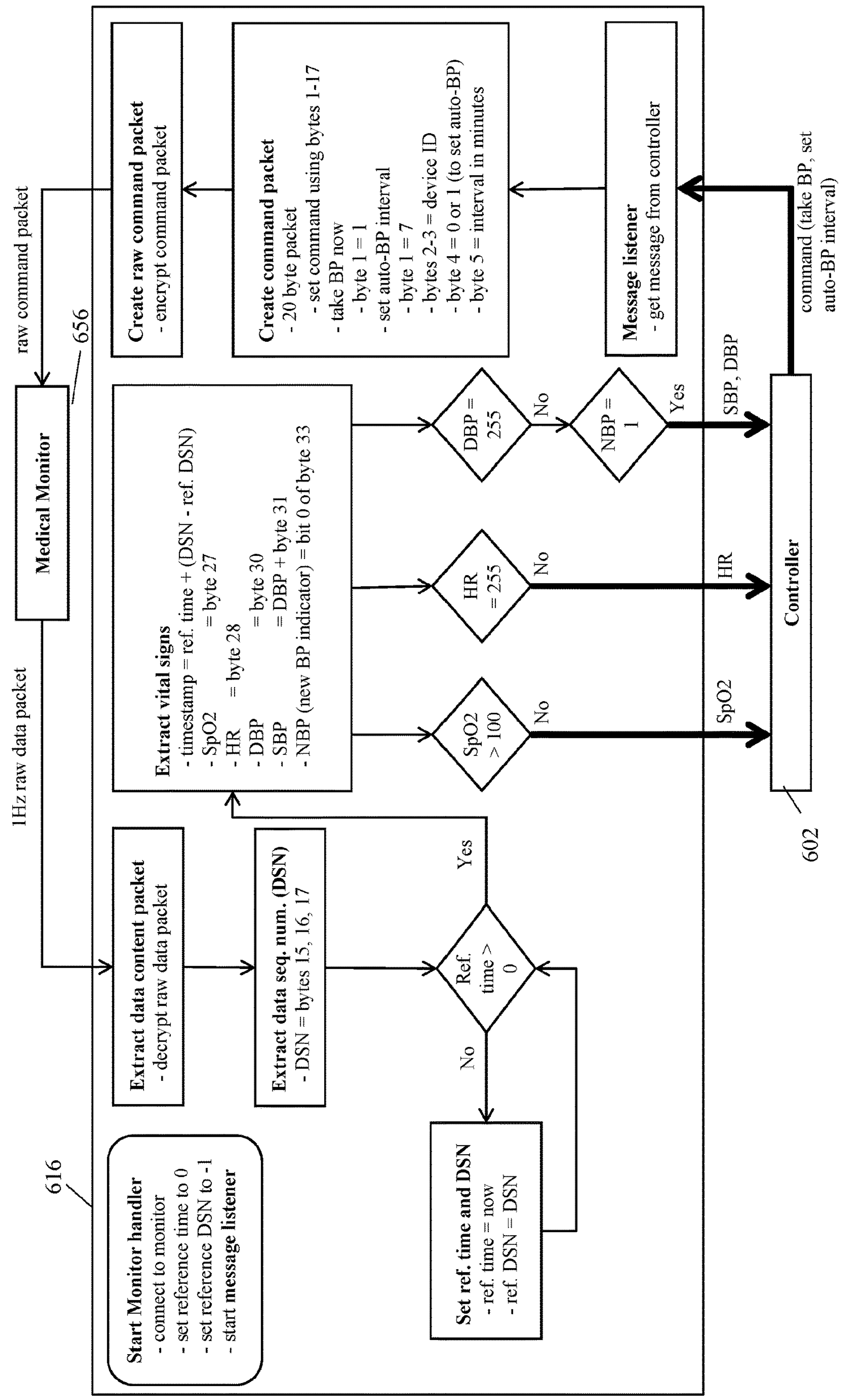
Figure 6D:
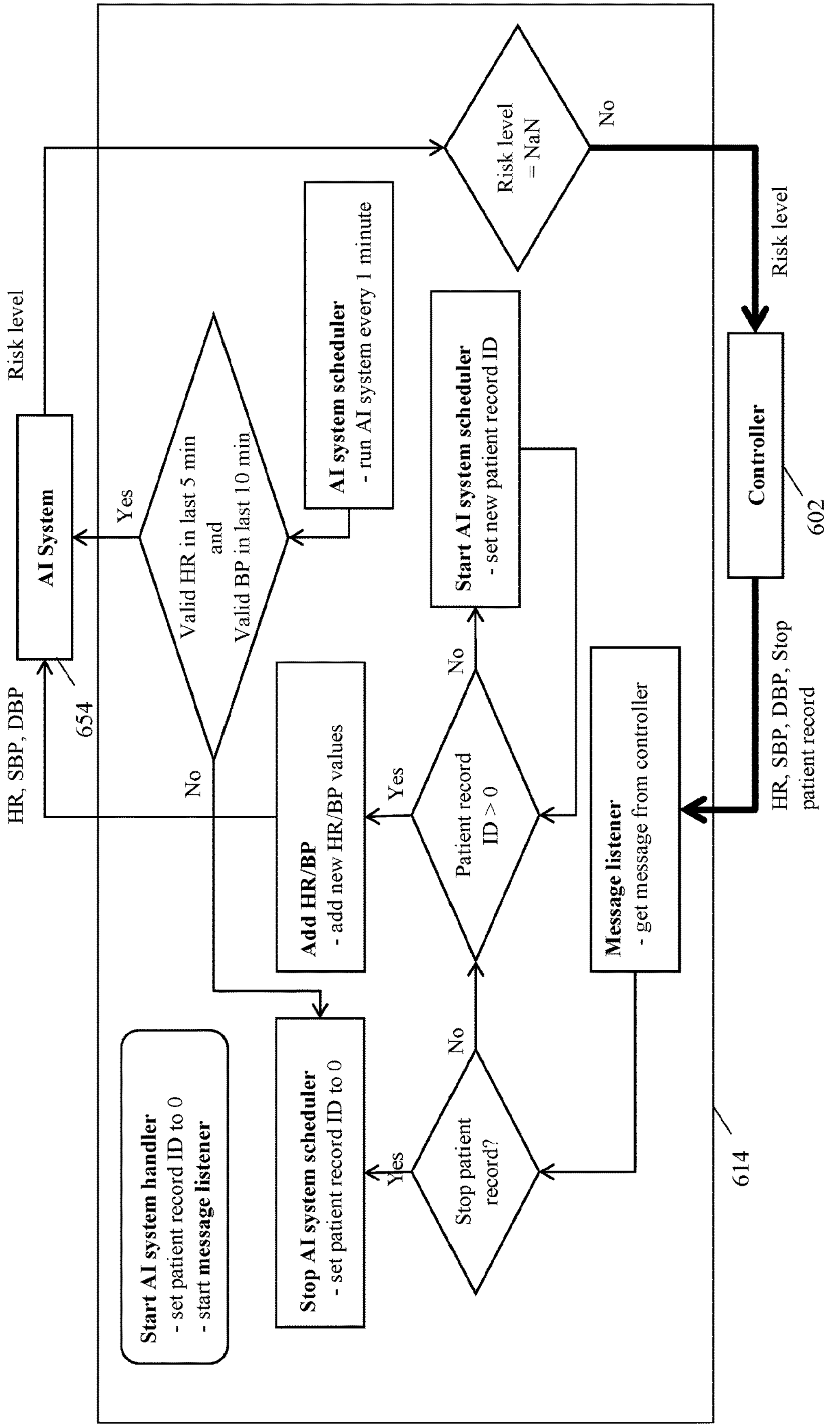
Figure 6E:
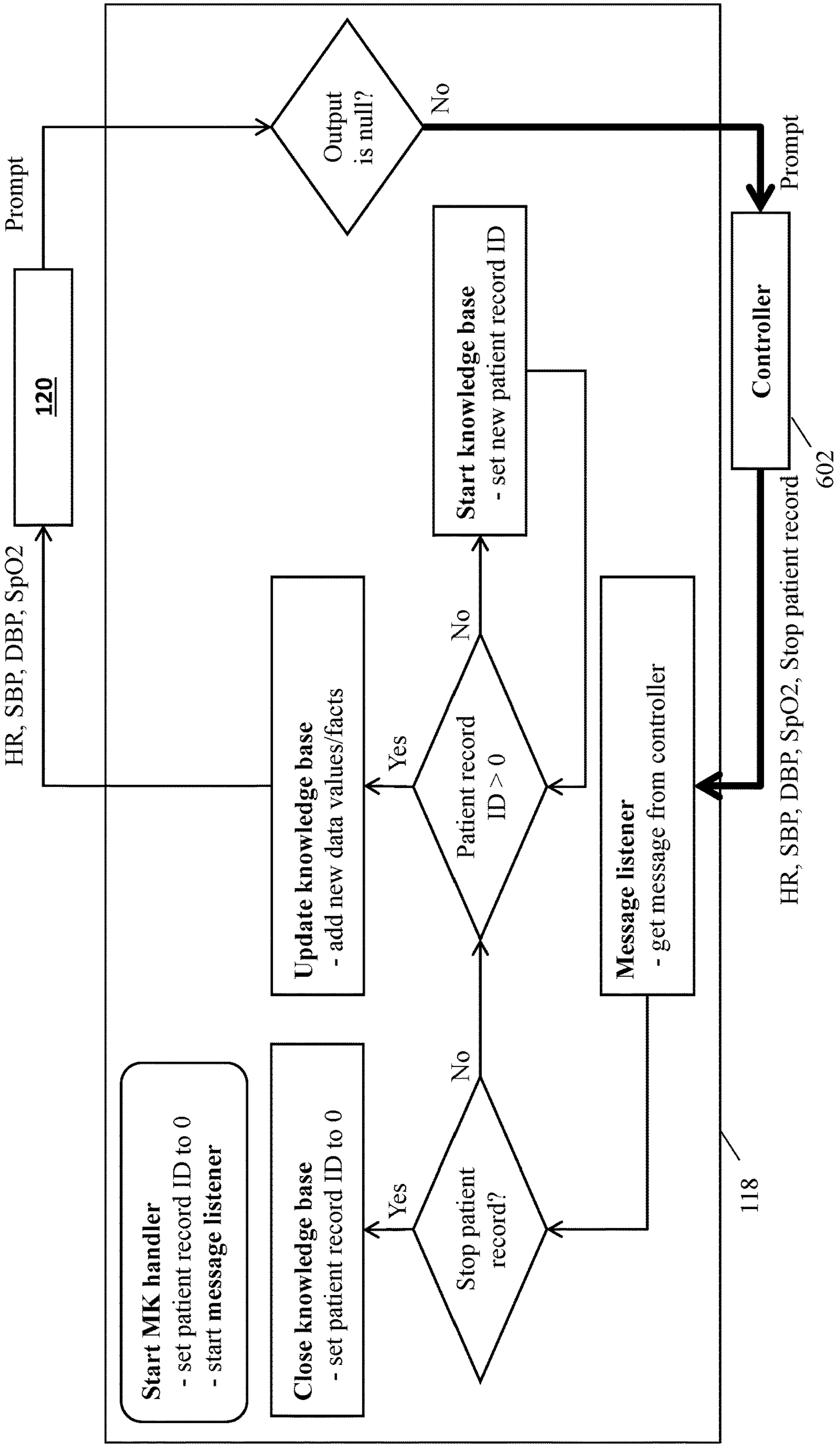

The medical knowledge library 120 is configured to receive the information from the medical knowledge handler 118 as facts to be used in analysis by the rules engine 124. FIG. 6E illustrates an example of how the medical knowledge library handler 118 could operate between the controller 102 and the medical knowledge library 120. The rules engine 124 uses the received facts to determine the patient state and what additional facts are needed to provide an assessment and a suggested treatment(s) for the casualty using a set of rules. In an alternative or further embodiment, the medical knowledge library 120 includes a buffer (or delay) to receive incoming messages and/or store facts prior to the facts being asserted to the rules engine 124 that the control module 122 releases to the rules engine 124 at predetermined intervals providing an advantage of avoiding hysteresis activity by the rules engine 124 in response to new facts that build on recent facts causing a change in suggested treatments.

In at least one embodiment, the existence of one fact X will imply the existence of another unknown fact Y when the user provides information to the main system 100 that fact X exists meaning that a prerequisite fact Y would exist. One approach to accomplish this is that if fact X is received by the rules engine and fact Y is unknown, then the rules engine will determine fact Y to be consistent with fact X. One example is if blood products have been provided to the casualty independent of a suggestion by the medical knowledge library 120, then the rules engine 124 would set a fact that an IV has been established. Another example of one fact leading to another fact is if a tourniquet is applied without the user informing the system that a hemorrhage exists, then the rules engine 124 will set a fact that a hemorrhage is present and proximate to the location of the tourniquet. Under either of these examples, the rules engine 124 will communicate to the controller 102 via the handler 118 of the fact that has been concluded for inclusion in the database 104 for the casualty and, in a further embodiment, store the fact in the facts repository. In a further embodiment, the user may correct the concluded fact Y in a situation where the base fact X resulted from an atypical situation and/or an off-label use of a medical supply.

In a further embodiment where the rules engine may not be an inference engine and periodically reassesses the casualty's status, for example in a situation where an inferred fact is based on a trend, based on the contents of the facts depository, which may include historical information, the rules engine will check to see if a particular fact to be obtained from an evaluation or a treatment exists already by, for example, checking the facts repository for the fact and/or requesting information from the system database 104 via the controller 102 (instead of requesting information the user interface). If the fact is present for the casualty, then the fact can be considered unless the fact relates to an evaluation or a treatment that may occur multiple times on a schedule and the fact is older than a predetermined time period (and thus is not temporally related), for example monitor SpO2 level is suggested every 5 minutes, but a new SpO2 value was just given 30 seconds ago would lead the rules engine to use the reading from 30 seconds ago. In a further embodiment, the predetermined time period is based on the fact such that some facts will have different predetermined time periods from other facts. In a further embodiment, when a rule requests an evaluation or treatment, the rules engine will confirm that the planned action is still necessary based on the casualty's state before having instructions sent to the user to perform that new evaluation or treatment.

In an embodiment where multiple casualties are being monitored with one medical knowledge library, the rules engine uses the location and/or casualty identification to differentiate between both casualties and injuries when accessing facts from the facts repository or the fact includes the location and/or casualty identification. In at least one embodiment when the rules engine 124 encounters a conflict between facts, the rules engine 124 will use the newer fact and disregard the earlier fact for this particular analysis unless the analysis is in part based on a trend, then the facts may not in reality conflict with each other, for example when they involve a vital-sign measurement. Another approach to resolve a conflict is a rule that fires when a new systolic blood pressure fact is sent and an old systolic blood pressure fact is present, the rules engine could use this rule and then retract the old systolic blood pressure fact:

```
(defrule sbp-retract
    (vitals (time ?time) (name sbp) (value ?sbpvalue))
    ?sbp <- (vitals (time ?oldtime) (name sbp) (value ?oldsbpvalue)
    (test (< ? oldtime ?time)) =>
  (retract ?sbp))
```

In an alternative embodiment, the old systolic blood pressure could be reclassified to the previous systolic blood pressure to facilitate the rules engine tracking a series of vital-sign readings for systolic blood pressure. These two concepts are applicable to other facts.

The First Example (present at the end of the disclosure) provides an example of part of a quasi-set of rules for the assessment of an airway injury. The "Question:" and "Intervention=" represent places where the rules engine 124 includes a rule when fired asserts a procedure fact to the control module 122. In response, the control module 122 retrieves all new procedure facts from the rules engine 124 to find a new procedure fact exists. The control module 122 then instructs the serial knowledge manager 127 to retrieve the relevant procedure object(s) and if the procedure object(s) exists, then the serial knowledge manager 127 sends it to the control module 122, which then sends it to the medical knowledge handler 118. In at least one embodiment, the procedure objects are created after the instance is started when the serial knowledge manager 127 retrieved assessments and/or intervention from the respective database 128, 128A, 128B. In an alternative embodiment, when the rules engine 124 outputs file name identifier, the file name identifier is used to retrieve the assessment/intervention from the respective database 128, 128A, 128B instead of the use of procedure objects. Rule 5 in section F is an example of how an additional fact can be inferentially determined. This quasi-set of rules also provides an example of how priority may be set using a numerical value. One implementation approach is to use C Language Integrated Production System (CLIPS) for the expert system contained within the rules engine 124. Another implementation approach is to use DROOLS, which is an open-source business rule management system. The Second Example (present at the end of the disclosure) provides an example of a subset of the massive hemorrhage rules in CLIPS. This construction of the rules engine 124 will allow for it to be readily updated or modified by swapping or initiating a different instance based on particular rule sets as methodologies change for evaluation and/or treatment without altering the underlying system architecture. As the rules engine 124 works through the rules, it utilizes the known facts, for example stored in the optional facts repository, to progress through the rules and to request additional information via the medical knowledge handler 118 to the user interface. As a new fact(s) is received by the medical knowledge module 120, the control module 122 asserts the fact to the rules engine 124 and initiates a run of the rules engine 124 to consider the new fact(s) in conjunction with known facts to either request additional fact(s) and/or select a suggested treatment.

In at least one further embodiment, the rules engine 124 will perform calculations and/or comparisons based on the facts as to dosages to recommend for administration to the casualty in response to the received facts. In at least one embodiment, the availability of a particular supply item is a fact to be considered by the rules engine 124 such that different treatment options may be provided to conserve that supply item. For example, when there are multiple casualties that the better treatment option is the use of the supply item in question and/or a longer time frame before external assistance may be available, then one way to accomplish this is for the rules engine 124 to project future supply usage to ration that supply item based on known casualty information or to use an inventor flag to trigger an alternative treatment to suggest if the alternative is effective enough. Another example of how limited supplies can be accounted for is to suggest a different treatment option for the casualty when the supply item(s) for a preferred treatment option is not available. In at least one multi-casualty embodiment, the medical knowledge library 120 includes one or more inventory facts which are used to track supply levels. In a further embodiment, the controller 102 will send a message to the database 104 that an intervention has been performed and to decrement, if applicable, the inventory for any supply item in response to receiving the complete message from the user interface module. The database 104 will send a new fact for the updated inventory level of the supply item to the controller to be passed to any currently running medical knowledge library 120 instances.

Examples of facts along with how the user interface may collect the information for the facts are as follows:

Completed (yes/no): The user interface may obtain information for this with a checkbox with no default or a prompt depending on how the user interface is implemented. See, e.g., FIGS. 3I, 4B-4D, and 5E. In at least one embodiment, the last step in the current instructions will be whether it is completed or, alternatively, when the last step is performed the medical knowledge library 120 will know that the treatment is completed, and, in at least one embodiment, the user selection of a complete button in the user interface will cause a message to be sent to the controller 102 that the treatment is complete or, alternatively, the controller 102 will act on the user interface complete message to update the database 104. In an alternative embodiment, the user interface will be configured to receive user input that an entire procedure and/or intervention is complete instead of having the user confirm completion of each sub-step. In at least one user interface implementation, nothing else will appear in this series of steps until after a selection has been made.

Conditions at start (yes/no): conscious, obstructed, torso trauma, blast, traumatic brain injury (tbi), verbal, oral medications, chest seal, shock, injury to chest, respiratory distress.

Conditions at start (value): pain; Alert, Voice, Pain, Unresponsive (avpu) scale or Glasgow Coma Score (GCS); total burn surface area (tbsa).

Conditions during (yes/no): still obstructed, radial pulse, hematoma, hissing, symptoms, success, bleeding stopped, distal pulse.

Conditions during (value): SpO2.

For the previous four conditions, a similar data collection approach for each of them may be taken with the user interface. In at least one embodiment, the user interface would include an input slot, selection menu such as a popup window or a pulldown window, or checkbox for this information. See, e.g., FIGS. 3E-3I and 4B-4D. Or alternatively, if a prompt is needed, the medical knowledge library 120 will request an evaluation while, in at least one embodiment, it will avoid asking temporally the same question for different evaluations/treatments. In at least one embodiment, if two different interventions are waiting for the response to a prompt, once it is answered, regardless of how, both interventions will be updated. Once the prompt is completed, the step-by-step instructions for the intervention will be displayed.

Choice during (yes/no): Proceed as if hemorrhage? Reassess now? Can you monitor? Another? Tourniquet needed? In at least one embodiment, the user interface may obtain information for this type of fact with a checkbox with no default or a prompt depending on the implementation of the user interface. See, e.g., FIG. 3K. In at least one embodiment, the last step in the current instructions will be whether it is completed or, alternatively, when the last step is performed the medical knowledge library 120 will know that the intervention is completed. In at least one user interface implementation, nothing else will appear in this series of steps until after a selection has been made.

Choice during (other): NPA or SGA? Which blood products? Which fluids? IV or IO? Location? IV IO IM ODT?

Hemostatic, xstat, or itclamp? Morphine or OTFC? In at least one embodiment, the user interface may obtain information for this type of fact with a checkbox with no default or a prompt depending on the implementation of the user interface. See, e.g., FIG. 5F. In at least one user interface implementation, nothing else will appear in this series of steps until after a selection has been made.

Timing questions: 3 hours? 6 hours? In at least one embodiment, the timers or setting of alarms will be handled by the control module 122 of the medical knowledge library 120.

The control module 122 acts in response to instructions received from the rules engine 124, which it then will query the appropriate information from the serial knowledge manager 127, which it then sends that information to the medical knowledge handler 118 for the controller 102 to route the information. An example of this is that the rules engine 124 will assert a procedures fact to the control module 122 causing it to query the serial knowledge manager 127 for the associated procedure objects created from the contents of the database 128 (e.g., html files) at initiation by the serial knowledge manager 127. The information (or procedure objects) may include information requests, commands to external systems, timer/alarm status information, information requests to the main system 100, prompts for the user interface such as assessments, step-by-step instructions, photos, and videos. In an alternative embodiment as illustrated in FIGS. 1E and 1F, the database 128, 128A, and/or 128B is a collection of files that can be passed to the user interface, for example XML and/or HTML files, image files, and video files that can be retrieved, for example based on a file name outputted (e.g., text) by the rules engine 124. In at least one embodiment, the database stores the procedure instructions (128B) separate from the lists of questions/assessments (128A) for retrieval by the serial knowledge manager 127. The Third Example (present at the end of the disclosure) provides examples of an airway assessment and intervention as an XML file. In at least one embodiment, the assessment and/or the intervention will include a conditional fact (as mentioned above) to be returned from the user interface based on a selection or an entry by the user. In the Third Example in procedure index 1, there is an example of question with two options for the user to select via the user interface for whether the airway is open or not.

```
<question>
  <questionText>Airway Open?</questionText>
    <options>
      <option value="Yes">(condition (time (time)) (name airway) (value
unobstructed))</option>
      <option value="No">(condition (time (time)) (name airway) (value
obstructed))</option>
    </options>
  <questionmoreinfo>
    <questionmoreinfoText>air moving freely from nose and/or
mouth</questionmoreinfoText>
  </questionmoreinfo>
</question>
```

Depending on the selection, a fact will be returned through the user interface (to optionally the user interface handler) to the controller 102 to be passed to the handler 118 based on the selection of the user of the condition being airway and the value as being unobstructed or obstructed. As illustrated in the Third Example in procedure index 3, the fact may contain multiple parts as occur in whether there is trauma to the neck or cervical spine. Depending on the user selection, the fact will include the injury as trauma, whether it is present or not (value of yes or no), and the location being cervical.

```
<question>
  <conditionQuestion>(find-fact ((?f injury)) (and (eq ?f:name trauma) (eq ?f:location
cervical)))</conditionQuestion>
  <questionText>Trauma to Cervical Spine?</question Text>
  <options>
    <option value="Yes">(injury (time (time)) (name trauma) (value yes) (location
cervical))</option>
    <option value="No">(injury (time (time)) (name trauma) (value no) (location
cervical))</option>
  </options>
</question>
```

In a further embodiment, the instructions can provide for expansion (or drilling down) in the user interface to match the skill and/or comfort level of the user with the images and videos providing a still further level of instruction. In the Third Example in procedure index 4, there is an example of how there can be a primary instruction for an intervention that is expandable into a list of sub-steps if the user needs more detailed instructions of how to perform the primary instruction. An example of this concept is having three levels of information that can be expanded by the user. This intervention example also illustrates how additional information may be made available to the user, for example through images such as "HEADTILT1.png". The illustrated structure provides three levels of explanation that can be used by the user depending on their comfort and/or skill level. The Fourth Example (present at the end of the disclosure) includes an example of how there could be three levels of instruction for a needle chest decompression intervention as represented by the highest level of the procedure name, the intermediate level by the numbered instructions, and the most detailed level by the letter instructions. Alternatively, there may be separate versions of the instructions based on the user's skill level, which would be a fact in this embodiment to be considered by the rules engine 124 when selecting the assessment/intervention or, in an alternative embodiment, the instance of the medical knowledge library 120 running will use rules for the user's level. In at least one further embodiment, each assessment and intervention will include a final entry for the user to confirm that it has been completed or to delay completion, which then will be converted into a fact for the rules engine 124 and stored in the local database 1044. At least one of these file structures provides some advantages including it being easier to add/modify the intervention instructions and assessments, potentially allows information to be presented to the user in a friendlier manner, and/or simplifies the ability to have different instructions and assessments for different skill levels and/or supplies.

In at least one embodiment, the control module 122 includes a timer module and/or an alarm module to provide timing information for any follow-up evaluations for the casualty based on a previous evaluation and/or treatment, the completion of that evaluation and/or treatment, and when a question is answered or fact is received. For example, an alarm could be set for two hours to check on an applied tourniquet by the user. One approach to accomplish this is for the rules engine 124 to assert a procedure fact with the name of the assessment/intervention, for example that checks on the applied tourniquet, that informs the control module 122 to query the serial knowledge manager for that assessment/intervention. When the control module 122 receives the assessment/intervention from the serial knowledge manager 127, it determines whether the assessment/intervention has a timer and when the assessment/intervention includes a timer the control module 122 starts a timer. When the timer triggers in the allotted time (e.g., two hours for a tourniquet) the control module 122 then checks any conditions that could prevent the assessment from being sent. If there are no conditions or the conditions are met then the assessment is sent to the medical knowledge handler 118. Info timer is present in the assessment/intervention, then the control module 122 sends the assessment to the medical knowledge handler 118.

Alternatively, the expiration of the timer or the alarm will cause a fact to be created for use by the rules engine 124, for example to cause a rule to fire starting a sequence of steps appropriate for that response if necessary. In an alternative embodiment, if the rules engine 124 receives a fact that the casualty has been evacuated or died, the set alarm is deactivated by the control module 122.

In at least one embodiment, when an intervention includes branches, the instructions will lead the user to the point where the branch happens to create a new fact for the rules engine 124 to act on before instructing the serial knowledge manager 127 to provide instructions for the relevant branch.

In at least one embodiment, where a delay is required, the control module 122 will start a timer for the delay period. When the delay is over, the control module 122 will send the information to the medical knowledge hander 118 to create a message to be sent to the controller 102. In some cases, a step may be an intervention that has a file in its own right. In those cases, the single step in the original file will be replaced by a call to open the other file. It is also possible that a series of steps may be different for the different skill levels of user. In those instances, there will be different files available. Which file should be opened will be indicated in the request from the medical knowledge handler.

In at least one embodiment, the rules engine 124 will determine if the fact has already been provided before issuing a new request. If the response is already available and is temporally close to the current time, the prompt step would be replaced by a completed. Depending on the implementation, temporally close may be a predetermined length of time or a percentage of the time between scheduled prompts that are uniform system wide or set based on the prompt or prompt-type. One approach to determining whether a fact already exists is to include within the assessment and/or the procedure an inquiry to confirm the fact does not exist. An example of this is in the Third Example in procedure index 1 where there is a conditional question regarding the airway:

<conditionQuestion>(find-fact ((?f condition)) (eq ?f:name airway))</conditionQuestion>.

In at least one embodiment, the "find-fact" will cause the rules engine to retrieve the fact from the current fact list, or, in an alternative embodiment, an inquiry to be sent to the local database 1404 through the controller 102 to retrieve data for this fact. If the fact exists, then the assessment when displayed on the user interface will reflect the status of the airway and not inquire with the user again as to whether the airway is open or not. In a further example, a new inquiry would be made if there is a change in other facts that would indicate that a change has occurred for this fact. In a further embodiment, the rules engine 124 may also request that a set of steps be updated to replace the prompt if the list was already sent before the response came in.

In an alternative embodiment for the database structure as illustrated in FIG. 1F, the individual databases 128A, 128B of the medical knowledge library 120 may be included as sub-databases of the reference database 128 of FIG. 1E. FIG. 1F also illustrates how the user interface (UI) handler 110A may be shared between the external user interface 158 and/or an API for connection to other systems such as the BATDOK or MEDHUB systems 150. The user interface is configured to display the patient information/status along with provide a point of interaction with the user. In an alternative embodiment as discussed previously, a user interface module 106 is included in the system as illustrated in FIGS. 1A-1C. In an alternative embodiment, a visual user interface is omitted or limited to displaying information. The API may also be configured to provide patient information/status along with recommendations, alerts, and alarms to the other system, which in at least one embodiment the user can use as the user interface. The previously discussed handlers for medical sensors, algorithms, and automated devices are also an option to display information when those external components are present. The previously discussed database 104 and controller 102 are included in this example embodiment.

In at least one embodiment, the user can use the main system 100 as a training tool to review procedures and watch any accompanying videos from the reference database 128, 128B to increase their skill and/or comfort level. In at least one embodiment, the receipt of a training request through the user interface will cause a message (or a fact) to be sent through the main system 100 to the controller 102 to begin a new instance of the medical knowledge library 120 configured to provide access to interventions. In an alternative embodiment, the training request will include a request to retrieve a selected intervention from the medical knowledge library 128, 128B.

In at least one embodiment, the initial assessment of a casualty follows MARCH, which is used by U.S. military medics for assessments, with related questions grouped together to allow the user an easier time for data entry and to organize the information into facts for use by the rules engine 124. In an alternative embodiment, the user is able to select where in the MARCH assessment the user would like to start an assessment. FIG. 3K illustrates an example of how MARCH could be utilized in the user interface as a series of assessment questions. In at least one embodiment as illustrated in FIG. 3K, the user interface includes a homunculus 242 and selection buttons 343 that can be used to enter the initial casualty information thus minimizing the questions that may be asked as part of the evaluation. In at least one homunculus embodiment, the user interface will return a selection as a region of the body instead of a specific location with an advantage being that a jittery selection will still provide a useful level of information and/or simplification to the logic of the rules engine. An example of this is if the user interface receives a selection of the front of the upper right arm, the whole area will be highlighted and region identified to the medical knowledge library 120 will be the front of the upper arm. In a further embodiment instead of a dot being shown, the entire region will be highlighted on the user interface. This figure also illustrates an example of a button 244 to rotate and, in a further embodiment, to enlarge the homunculus to tap on to locate identified injuries. FIG. 3M illustrates an example of how just the shoulder and head of the homunculus 343 are displayed during an airway and/or respiration assessment, although in an alternative embodiment this enlargement is not used. In at least one further embodiment, the questions are used in conjunction with the homunculus to provide location information for the injury. See, e.g., FIGS. 2A, 2B, 2E, and 2K. The gathered information provides the basis on which facts are generated to provide support for prolonged casualty care and can be supplemented by external systems such as a medical (or vital-sign) monitor. The gathered information may reduce the questions asked by the medical knowledge library 120 during the evaluation to avoid redundancy in the information gathering.

In an alternative embodiment, the selection of one MARCH icon will initiate an instance of the medical knowledge library 120 with a rules engine configured for that section (or part) of the assessment. In such an embodiment, the rules engine 124 may include rules to generate text outputs for conclusion(s) reached that are sent to the database 104, which would allow the database 104 to be a source of additional information for preliminary facts, if another section of the assessment is selected by the user. In a further embodiment, the controller 102 and/or database 104 will include fact parameters for selecting the information to be sent to a new medical knowledge library instance.

In at least one embodiment, treatment (or intervention) instructions are presented in a drill down format to allow the user to select the level of information that is required to perform the treatment successfully. For example, a top level is initially shown with the user able to expand the step into more detailed steps and/or request additional information, for example by selecting the "+" icon left of a particular step. See, e.g., FIGS. 3N, 3Y, and 4B-4D discussed in more detailed later. In at least one embodiment, the instructions allow the user to confirm performance/state in response to the instructions, with the lower level and more detailed version of the treatment instructions being marked as complete when the higher-level instruction is marked as complete, for example by selecting the checkmark for the step.

Figure 4A:
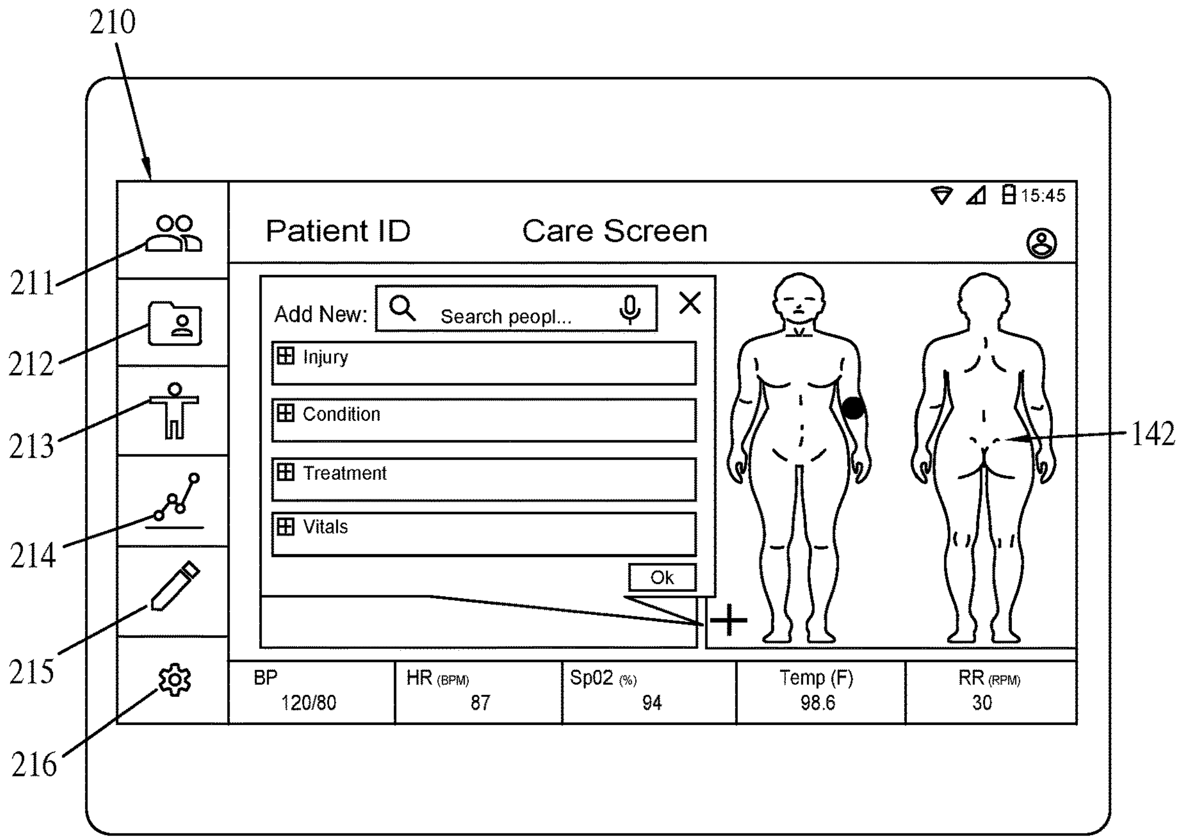
FIGS. 4A-4D illustrate a series of user interfaces according to another embodiment of the invention.
Figure 4B:
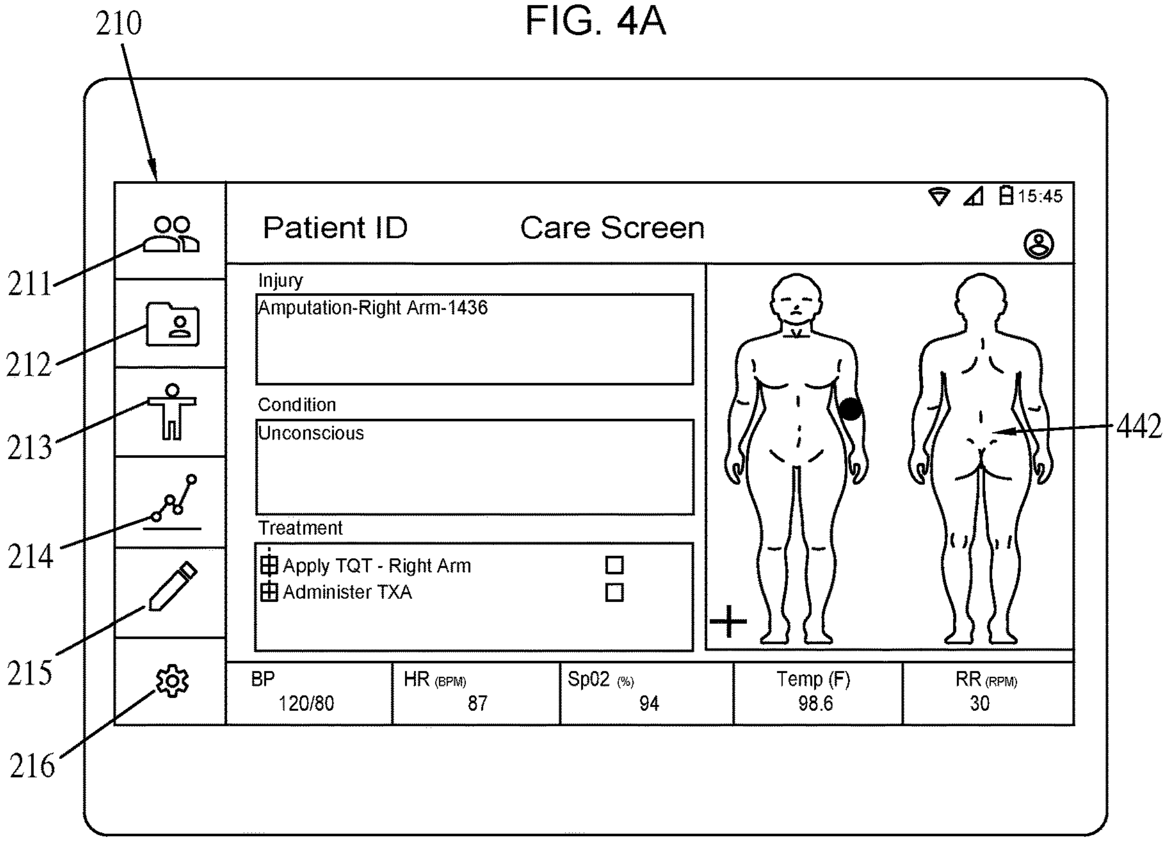
Figure 4C:
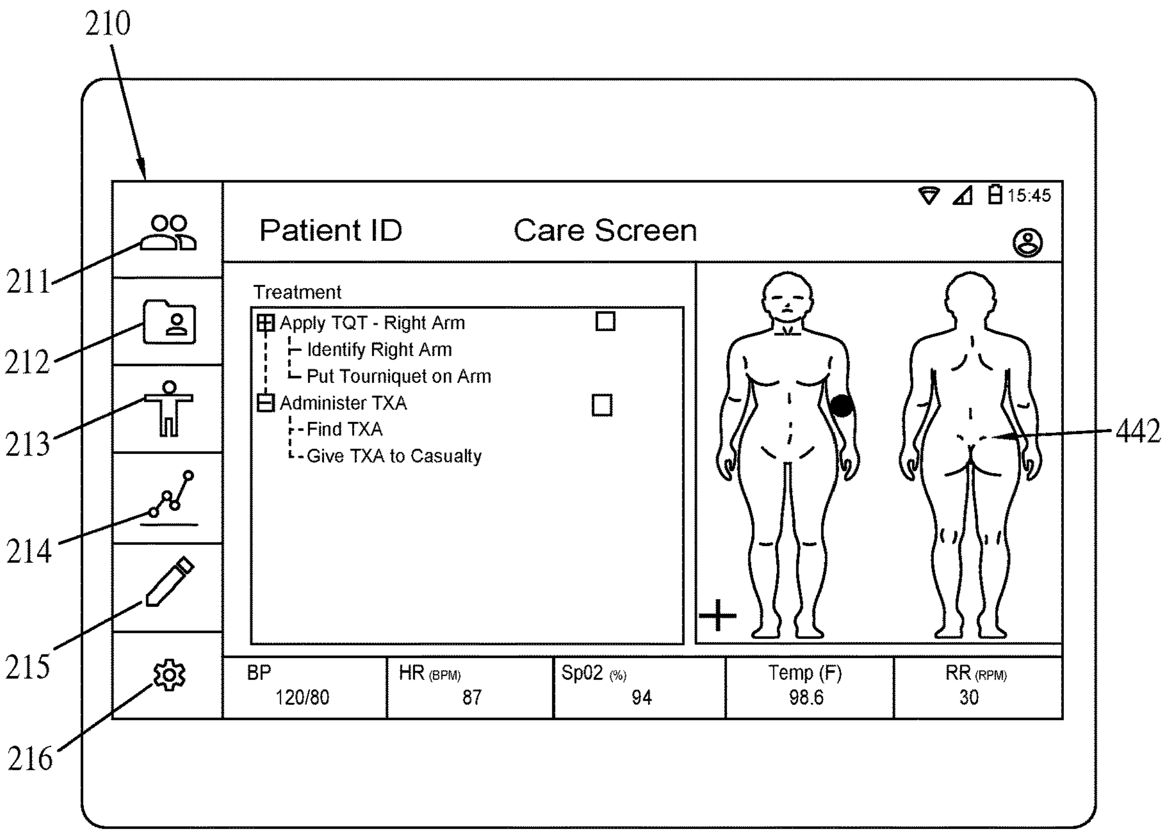
Figure 4D:
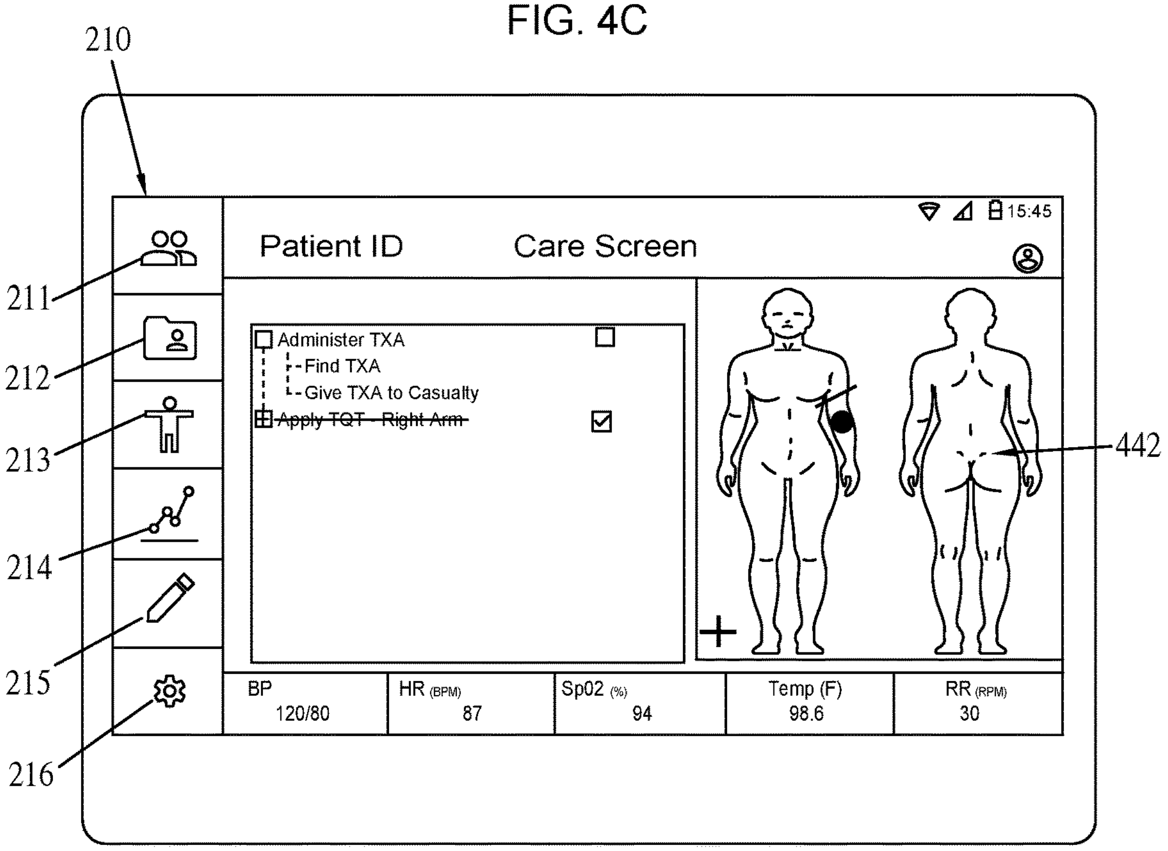
Figure 5A:
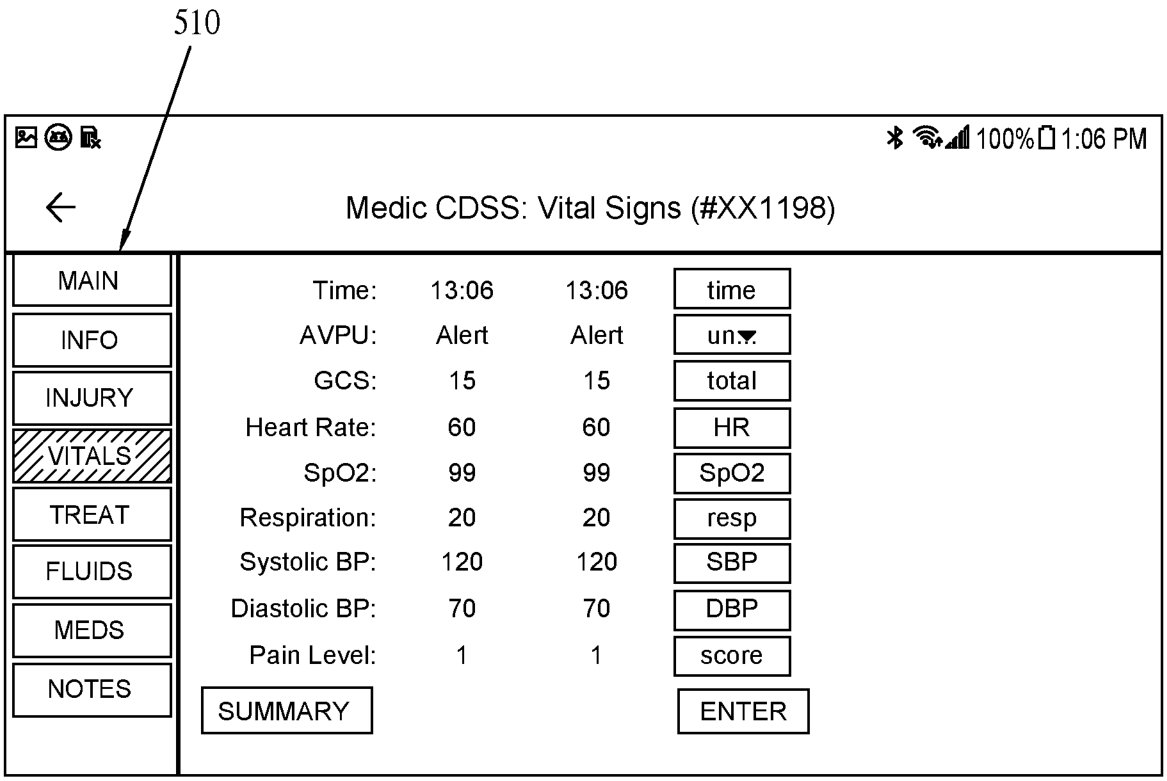
FIGS. 5A-5G illustrate a series of user interfaces according to another embodiment of the invention.
Figure 5B:
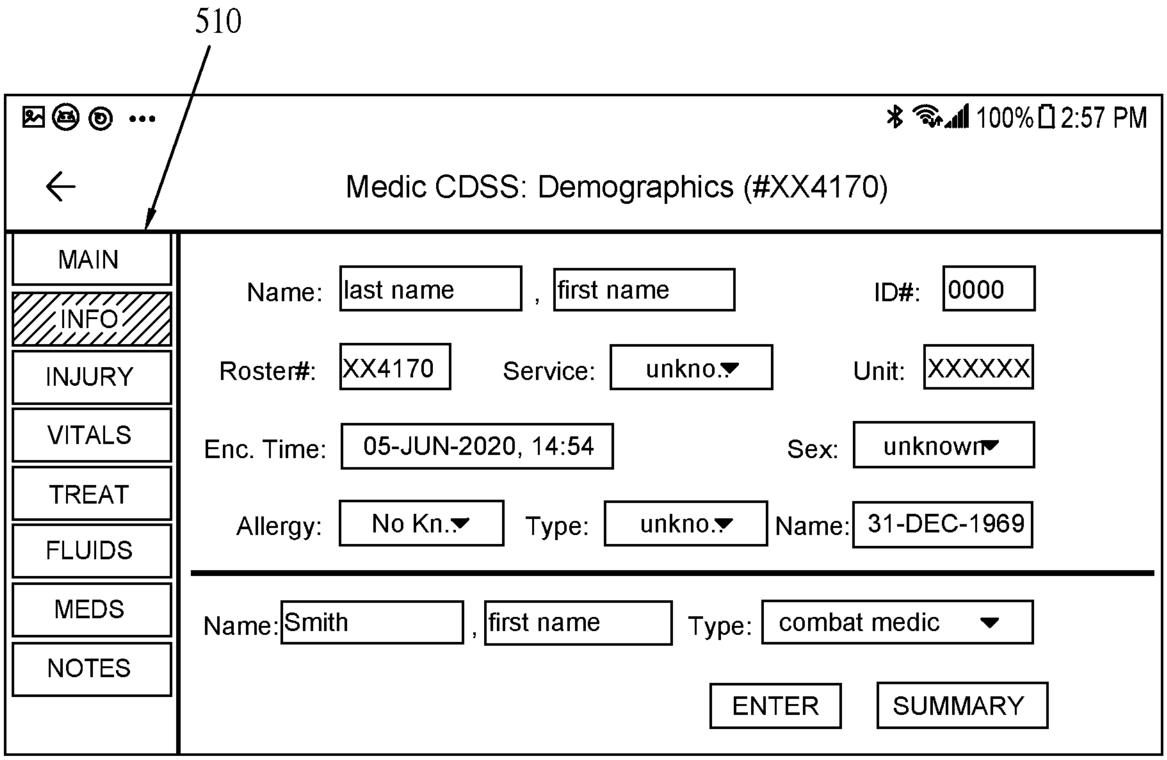
Figure 5C:
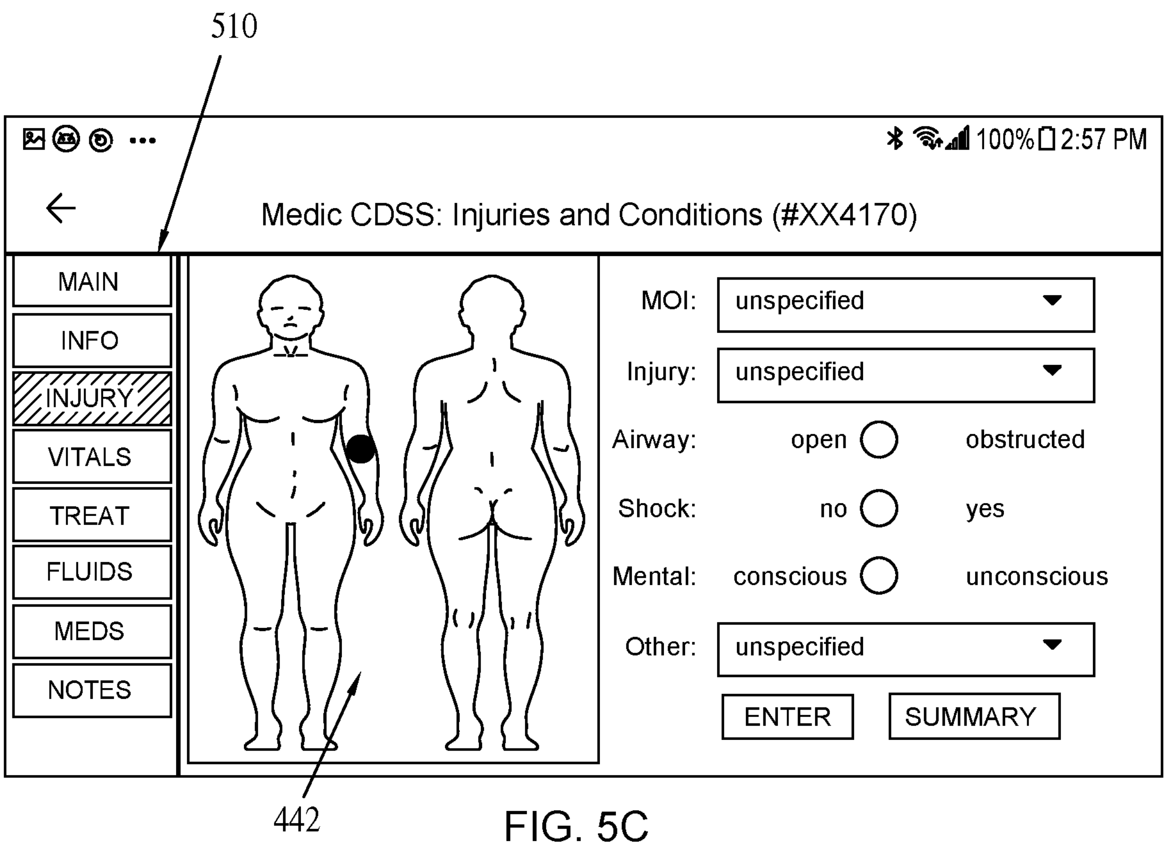
Figure 5D:
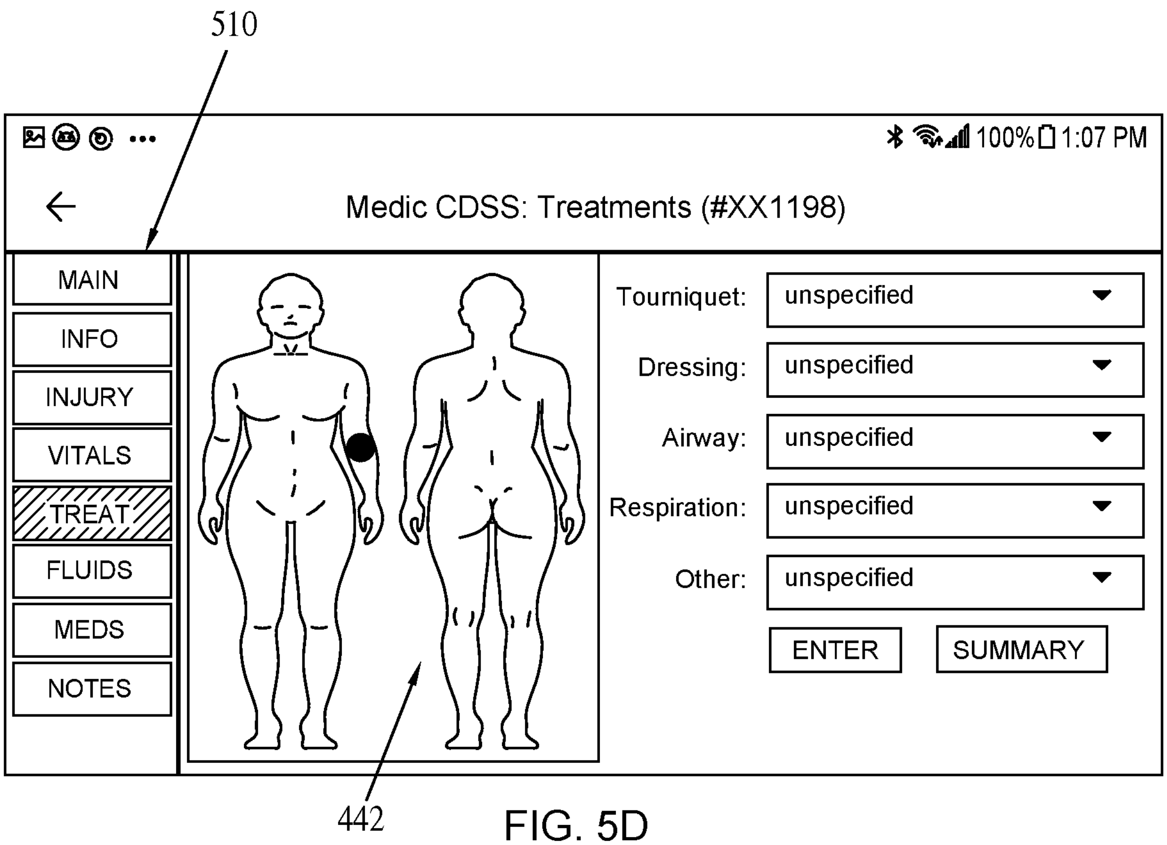
Figure 5E:
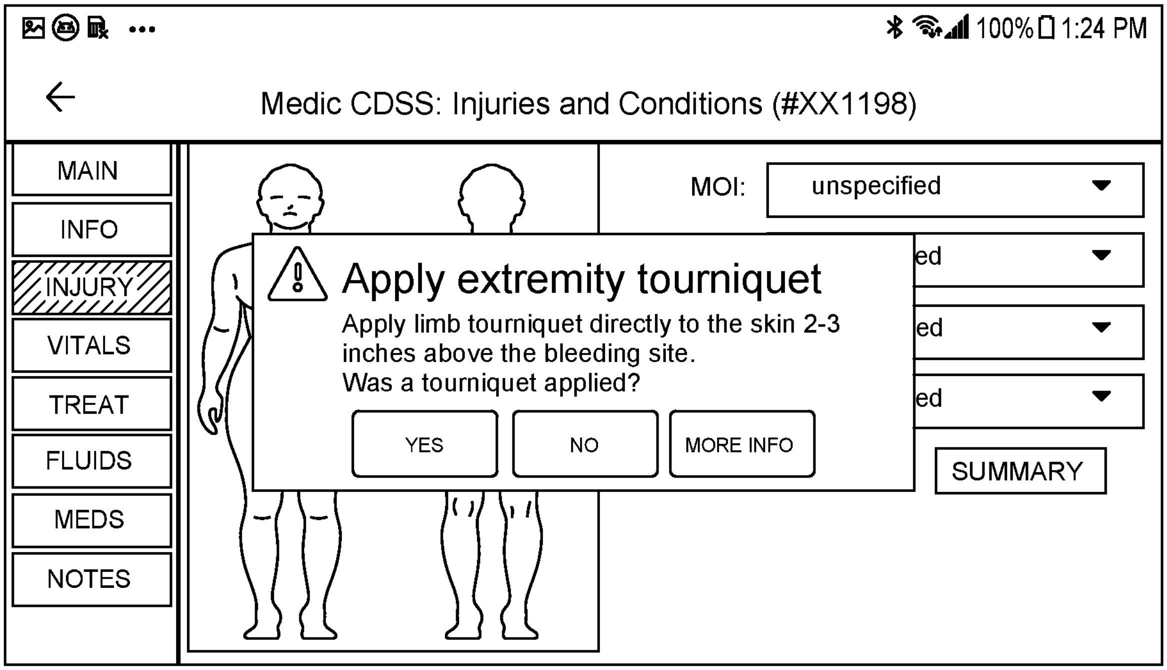
Figure 5F:
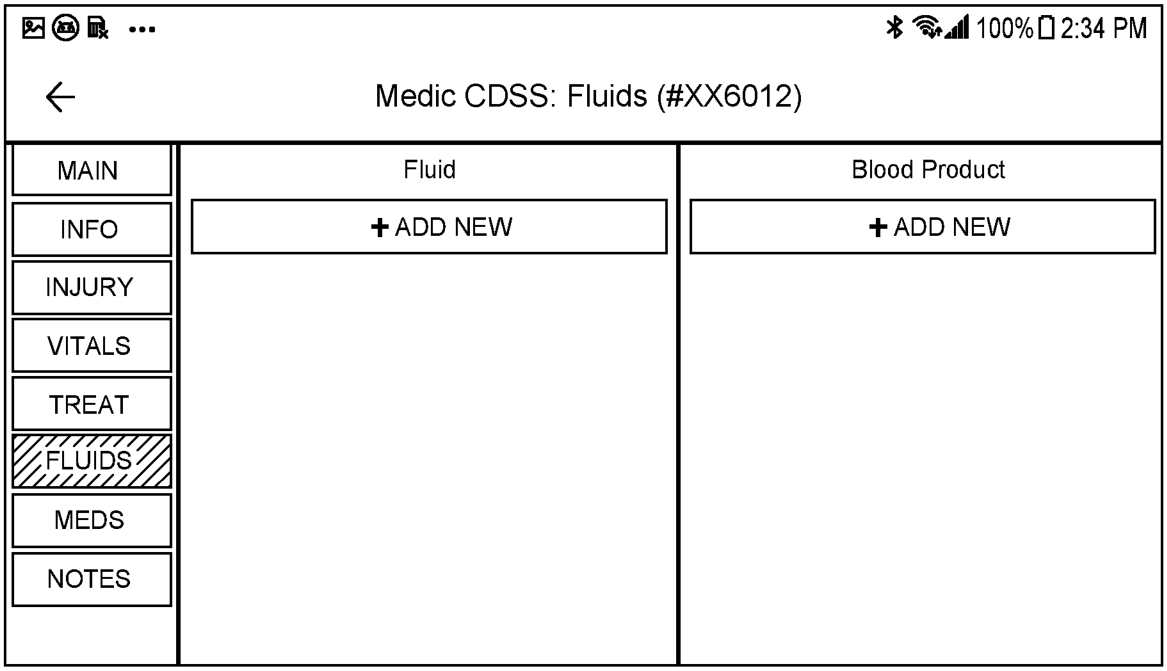

The user interface handler 110, 110A as illustrated, for example, in FIGS. 1D-1F is configured to communicate with an external interface system such as the BATDOK, the Medical Hands-free Unified Broadcast system (MEDHUB), the Integrated Visual Augmentation System (IVAS), a natural language processing system, and a text-to-speech system to facilitate communication with the user. FIG. 6F illustrates an example of how the user interface handler 110, 110A could operate, and, in an alternative embodiment, how the user interface module 106 may generally operate. In at least one embodiment, the external user interface is not present and the optional user interface module 106 of the system 100A-100C illustrated, for example, in FIGS. 1A-IC is used instead or in conjunction. Depending on the external interface system, those systems are configured to display patient information, patient status, treatment information; capture user input, for example through menus, checkboxes, and prompts; control the input/output to medical information systems, and/or communicate recommendations, alerts and/or alarms to the user and/or the front end system. FIGS. 2A-5G illustrate examples of how the user interface could be presented to the user through the external interface system or the user interface module 106. In at least one embodiment as illustrated in FIGS. 4B and 4C (e.g., with the color red for apply tourniquet and the color yellow for administer TXA), the user interface handler will prioritize procedures to be performed based on a rating system that conveys the medical urgency to perform a particular procedure such as an evaluation or a treatment based on the severity of the situation for the individuals being monitored. In an alternative embodiment, the user interface handler 110, 110A (and/or the controller 102) will prioritize any prompts based on priority and urgency (order of arrival) and sending them to the user interface. In an implementation in conjunction with the BATDOK or MEDHUB system 158, these respective interfaces may include a tab (or button) to access the front end system interfaces.

The input handler 112 illustrated, for example, in FIGS. 1A, 1E, and 1F is configured to communicate with external input systems 152, 154, 157, or 159 such as medical monitors, fitness monitors, AI and/or machine learning (ML) systems for example the APPRAISE system, a radio-frequency identification (RFID) reader, a global positioning system (GPS) device, a microphone such as present on the device running the system or helmet mounted, a vision detection system such as a camera for example on the device housing the system or helmet mounted, and/or a barcode reader, which may be software implemented in conjunction with the camera. In a further embodiment, the barcode reader includes a quick response (QR) code reader. FIG. 6C illustrates an example of how a medical (or input) monitor handler 112, 112I could operate. FIG. 6D illustrates an example of how an AI system handler 112I could operate. In an alternative embodiment, the input handler 112, 112I also relays to the controller 102 the information that the external system needs to operate. The input types include identifying the user and/or casualties, supply usage, vital signs, physical assessments, evaluations, injuries including type and/or mode, diagnoses, treatment, and/or actions. In a further embodiment, the treatment information may include suggestions, an amount of completion, and/or whether it was successful. The medical monitor, the APRAISE system, and the AI/ML system are examples of external systems 152-156 that can provide one or more vital-signs, assessment scores such as a numerical representation of the casualty's state and/or risk for adverse outcome, the casualty condition, and the injury for the casualty. The handler(s) 112 for the APPRAISE system and/or the AI/ML system would provide medical data including vital-sign measurements and scores to these systems so that recommendations including treatments and actions and/or derived medical data for the casualty could be prepared, for example to assist with the decision-making process of the medical knowledge library 120. In a further embodiment, the output of the APPRAISE system and/or the AI/ML system is provided as a fact to the medical knowledge library 120, which may include a conditional rule that uses the output if applicable. The visual detection system may provide a facial and/or fingerprint capture of the user and/or casualty(ies), a scan of medical supplies used such as an image of the medical supply used or capture of a barcode from the packaging, and/or a capture of the applied treatment or performance of the treatment/action. The captured and scanned information can be used by the controller 102 in conjunction with the database 104 and the medical knowledge library 120 to select the casualty and/or user from the database 104 based on the facial and/or fingerprint identification, name tag, or other type of identification for the individual; to augment the casualty/patient record; and/or to begin the starting of any timers or setting of any alarms, for example if a tourniquet was applied by the user to the casualty.

The device handler 112D as illustrated, for example, in FIGS. 1A, 1E and 1F is configured to communicate with an external device 152, 154 such as a remote-controlled or autonomous device such as a ventilator, an automated tourniquet, a robot, and a drone. The external devices 152, 154 will accept messages requesting that they execute some action, and in many implementations, when the action has been taken, the external device will respond. Examples of actions include adjust settings, start/stop treatment, adjust treatment, etc. The configuration will include how to formulate and structure the correct input for the external device 152, 154 based on the instructions (or a message(s)) sent by the controller 102. In at least one implementation, the device handler 112, 112D would relay instructions and confirmation of completion, success, or failure as appropriate of those instructions including, for example, adjust settings, perform an action, and start/stop a treatment. In the case of an evacuation drone, the instructions may include location information for the casualty, and in a further embodiment, identifying information for the casualty. For example, if a robot can apply the tourniquet, there should be a file that includes a message to the robot as one of the steps instead of a prompt to the user. In a further or alternative embodiment, parameters may also be handled and stored by the device handler 112, 112D for use when communicating with the external device 152, 154. In at least one embodiment, the device handler 112, 112D will be responsible for telling the controller 102 what the external device 152, 154 is capable of and which information it requires. In a further or alternative embodiment, the serial knowledge library 127 will have specific files for how these external devices 152, 154 fit into the work flow. In an alternative embodiment, the external handlers 112, 112D are omitted or not used by the system when not applicable.

FIGS. 1B-1D illustrate the overall system with the front end main system 100 having a first handler 114 and a second handler 116 connected to a first external device 154 and a second external device 156, respectively. These handlers 114, 116 are representative of input and/or device handlers 112, 112I, 112D discussed in connection with FIGS. 1E and 1F with the external devices 154, 156 being the corresponding external device 152-159. Based on this disclosure, a person having ordinary skill in the art should appreciate the number of handler and external device combinations may vary from those illustrated in FIGS. 1A-1F in any particular use of the system.

Figure 2A:
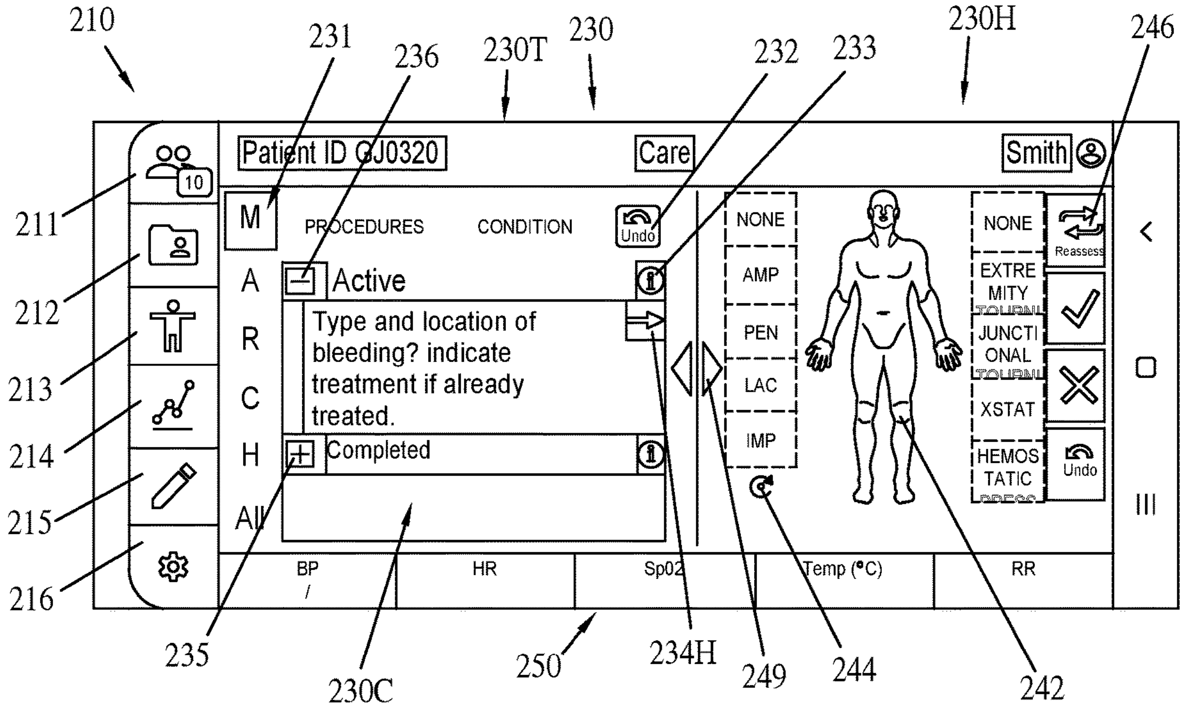
FIGS. 2A-2L illustrate a series of user interfaces according to at least one embodiment of the invention.
Figure 2B:
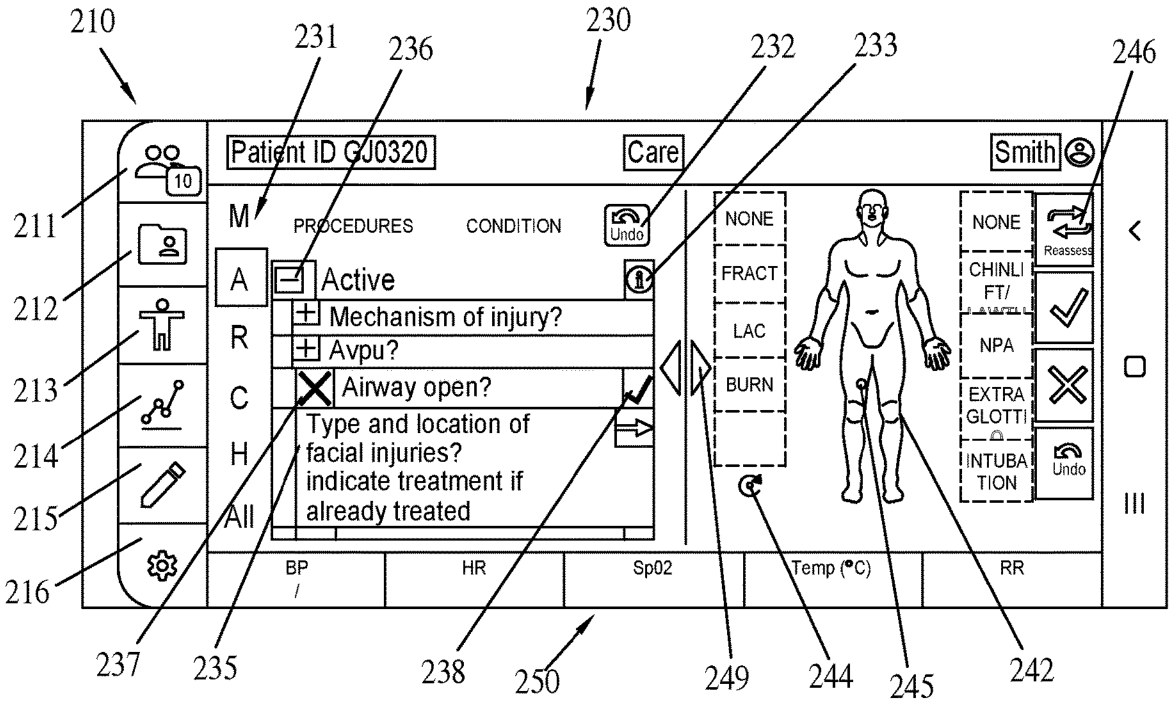
Figure 2C:
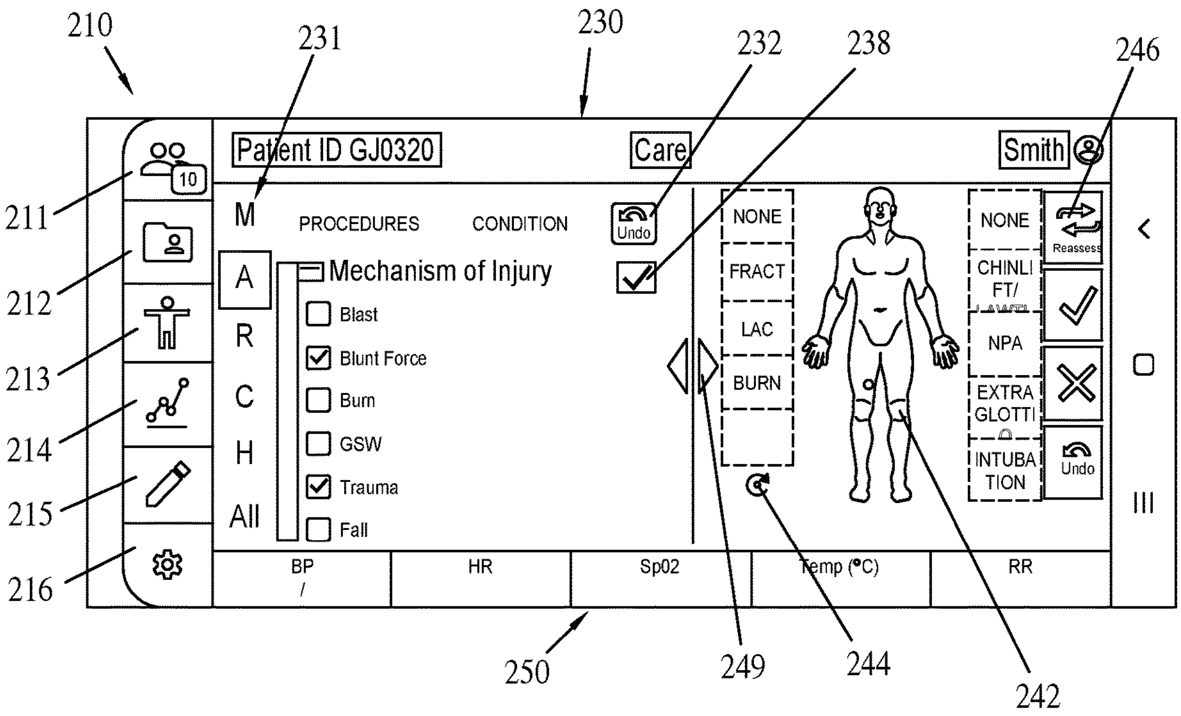
Figure 2D:
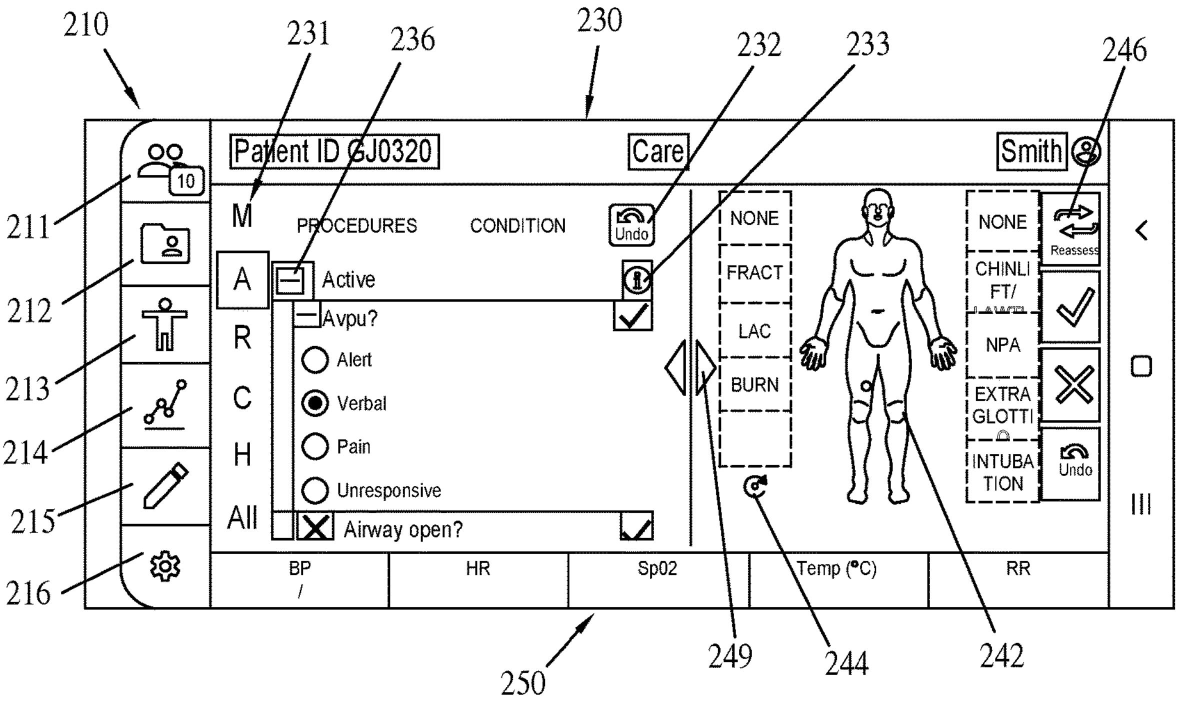
Figure 2E:
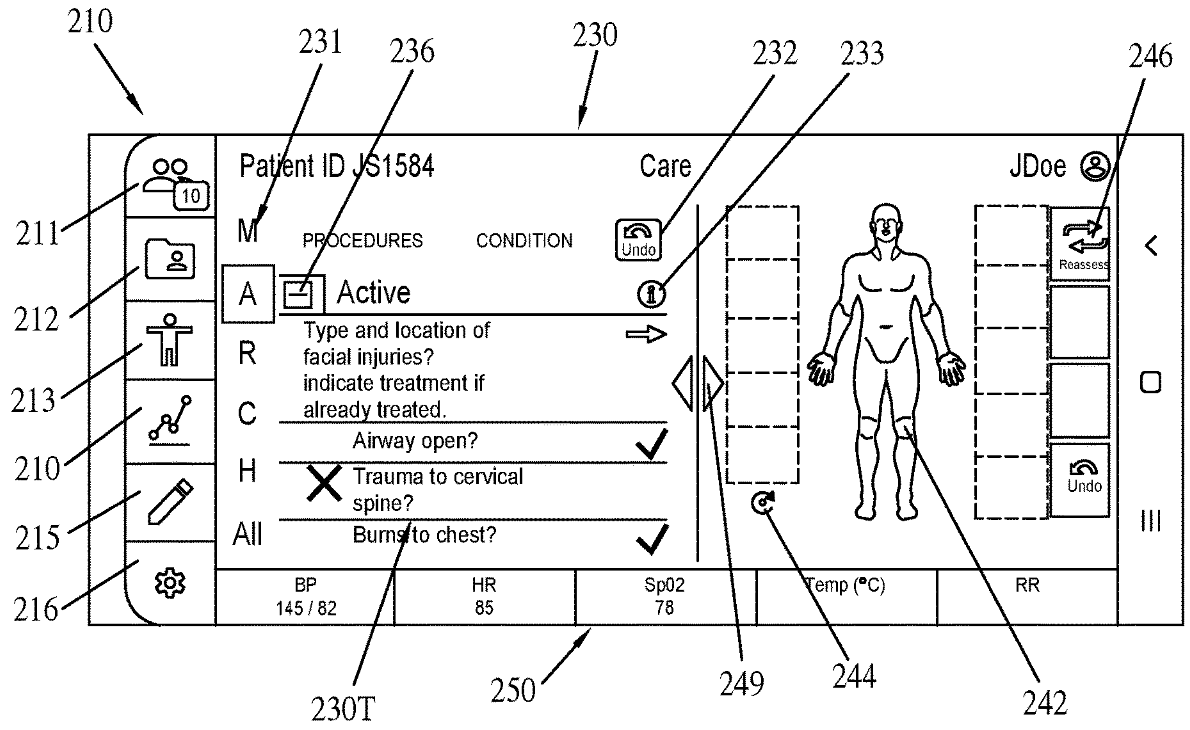
Figure 2F:
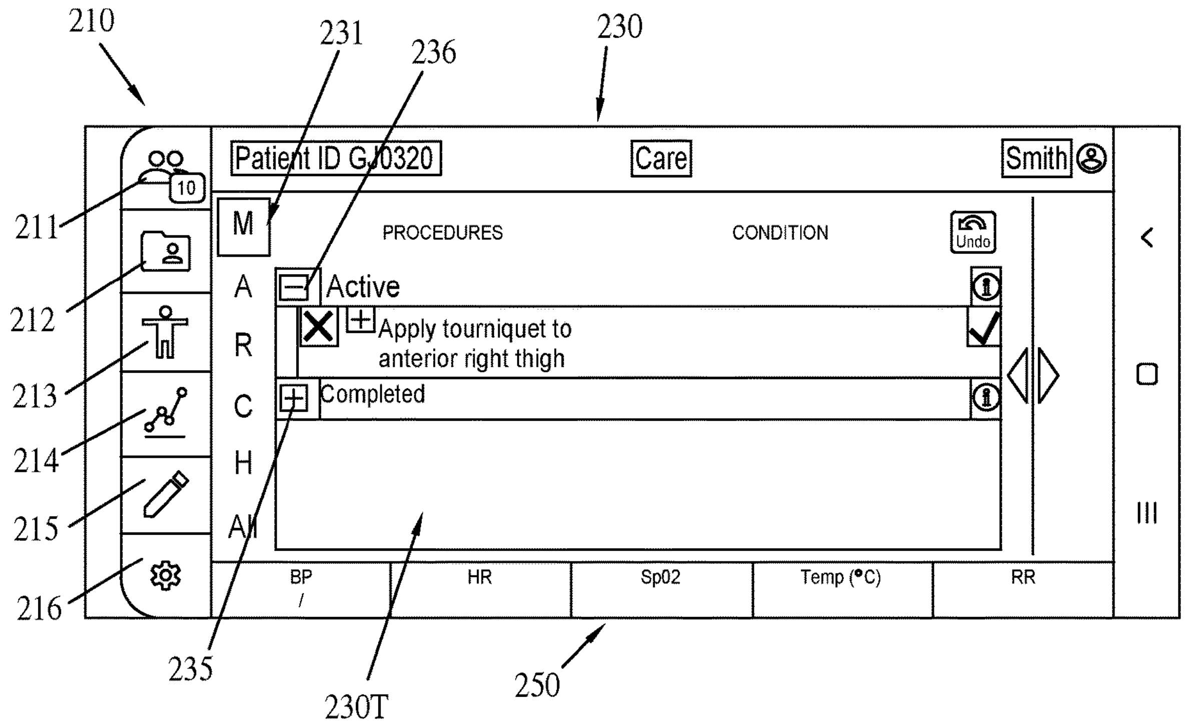

FIGS. 2A-2J illustrate example interfaces for performing assessments and interventions according to at least one embodiment of the invention. FIGS. 2A-2D illustrate how an assessment could be based on the MARCH assessment approach, which as discussed in other parts of this disclosure could be replaced by other assessment approaches, and how different levels of the information may be expanded or minimized by using "+" buttons 125 and "–" buttons 236. FIGS. 2A and 2B illustrate the use of an arrow 234H to direct the user to use a homunculus 244 to indicate the type and location of the injury and the possibility to rotate the homunculus to place the injury, for example on the back side of the homunculus. Each of these figures illustrate the ability for the user interface to expand or reduce the size of the textual section 230T while adjusting the size of the homunculus section 230H using a drawer arrowhead icon 249. FIG. 2B illustrates how the location of a hemorrhage could be indicated on the homunculus with a red (or other color) dot 245, or, in an alternative embodiment, the region of the leg could be highlighted or otherwise colored different than the rest of the homunculus and in a further embodiment, the highlight/color could be indicative of the type of injury. FIG. 2C illustrates how the "Mechanism of injury?" may be expanded to enter multiple selections 233 while FIG. 2D illustrates a multichoice response that provides for selection of one selection 234. In an alternative embodiment, the multichoice response may instead be a pop-up window like that illustrated in FIG. 2L. FIG. 2E illustrates how the user interface displays previously entered yes and no responses in the Completed section of the care window 230, which also illustrates the ability for the user interface to receive a request from the user to undo a completed response/intervention by selecting the undo button 232. FIG. 2E also provides an illustration of how the vital-signs for the particular casualty may be displayed along the bottom of the window in a footer 250 where colors can be used to provide a quick visual cue to the user, for example grey/black for acceptable or stale, green for acceptable if grey/black represents stale, yellow for cautionary, and red for unacceptable or dangerous condition.

Figure 2G:
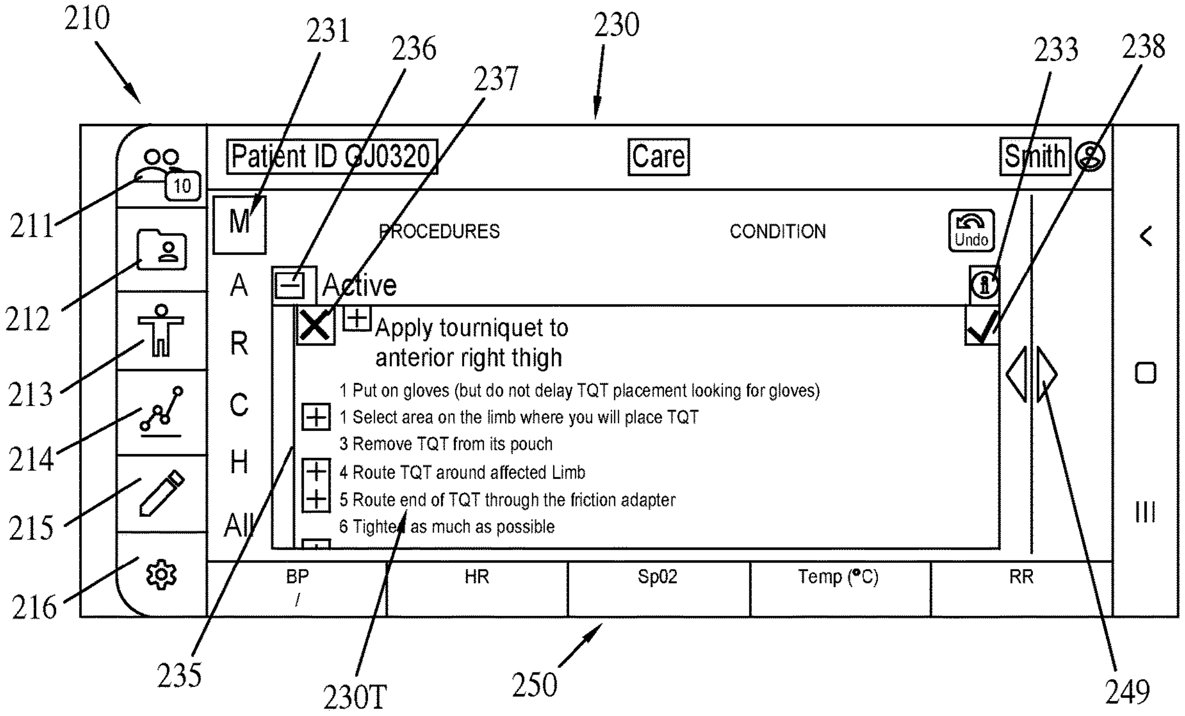
Figure 2H:
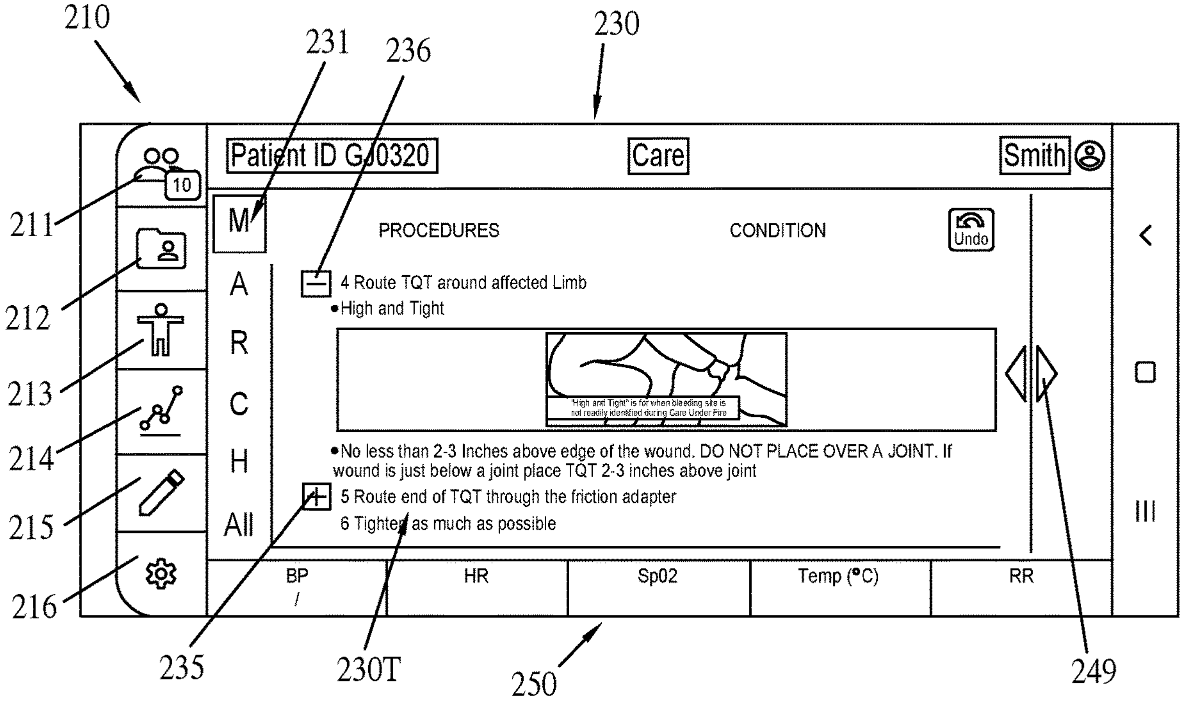
Figure 2I:
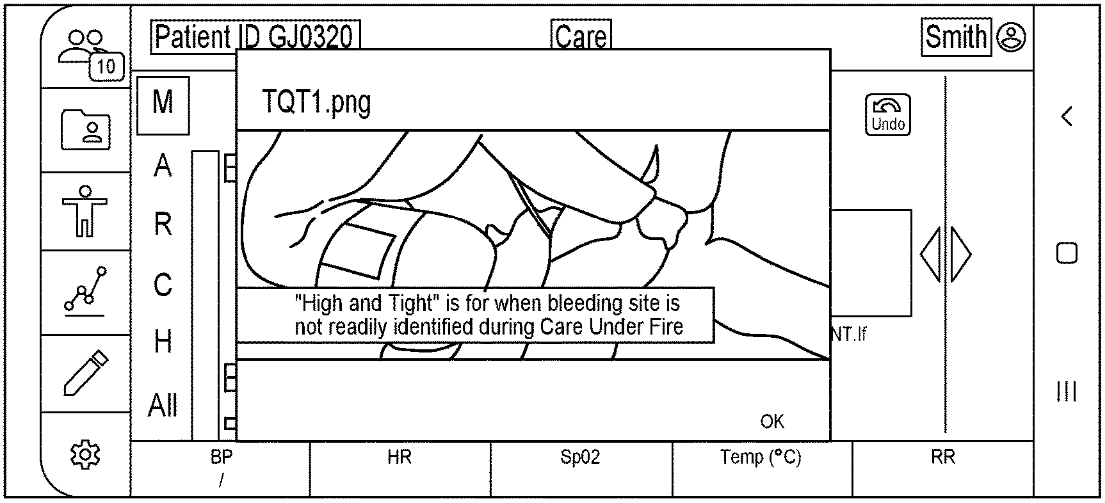

FIGS. 2F-2I illustrate how the suggested treatment would be displayed with the textual section 230T maximized and how three levels of instructions may be provided with the use of "+" 235 to expand the step lists (and a "–" 236 to reduce the list) and how the user can select the red "X" 237 or the green checkmark 238 to inform the system that the intervention has been performed, which in the illustrated interface is placing a tourniquet on the right leg. The three levels allow for a starting level (e.g., one line identifier that may be in a larger font), a second or intermediary level that provides shorter sub-steps, and a third or more detail level that includes more detail and may further include images and/or videos to illustrate different aspects. As interventions are performed and marked as complete, they can be greyed out and moved to the Completed section 230C of the care window 230. FIG. 2G illustrates a second level of instructions being displayed that also allow the user to expand further some of the sub-steps if additional information is needed as illustrated in FIG. 2H where step 4 is expanded and includes an image illustrating placement of the tourniquet. In at least one embodiment as illustrated in FIG. 2I, the user interface will provide an enlarged view of the image. In a further or alternative embodiment, the images may be instead videos of how to perform the step or some combination of images and videos. An example of where a video could be used is an intubation procedure.

Figure 2J:
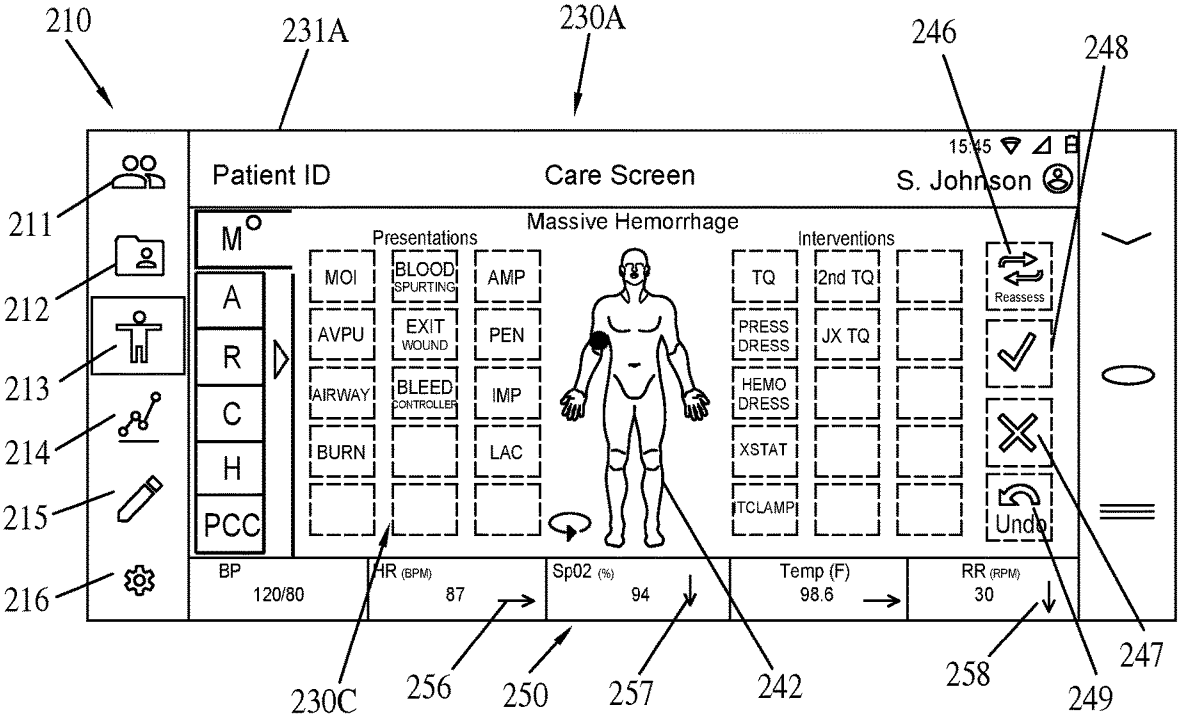
Figure 2K:
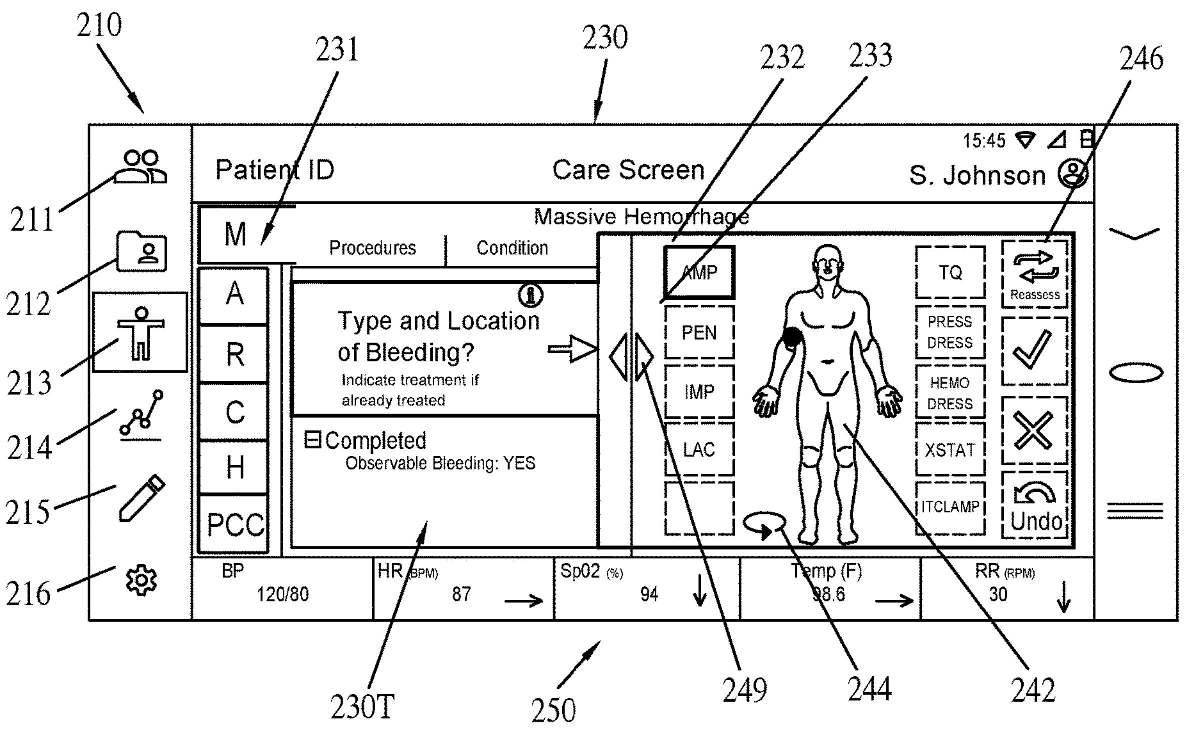
Figure 2L:
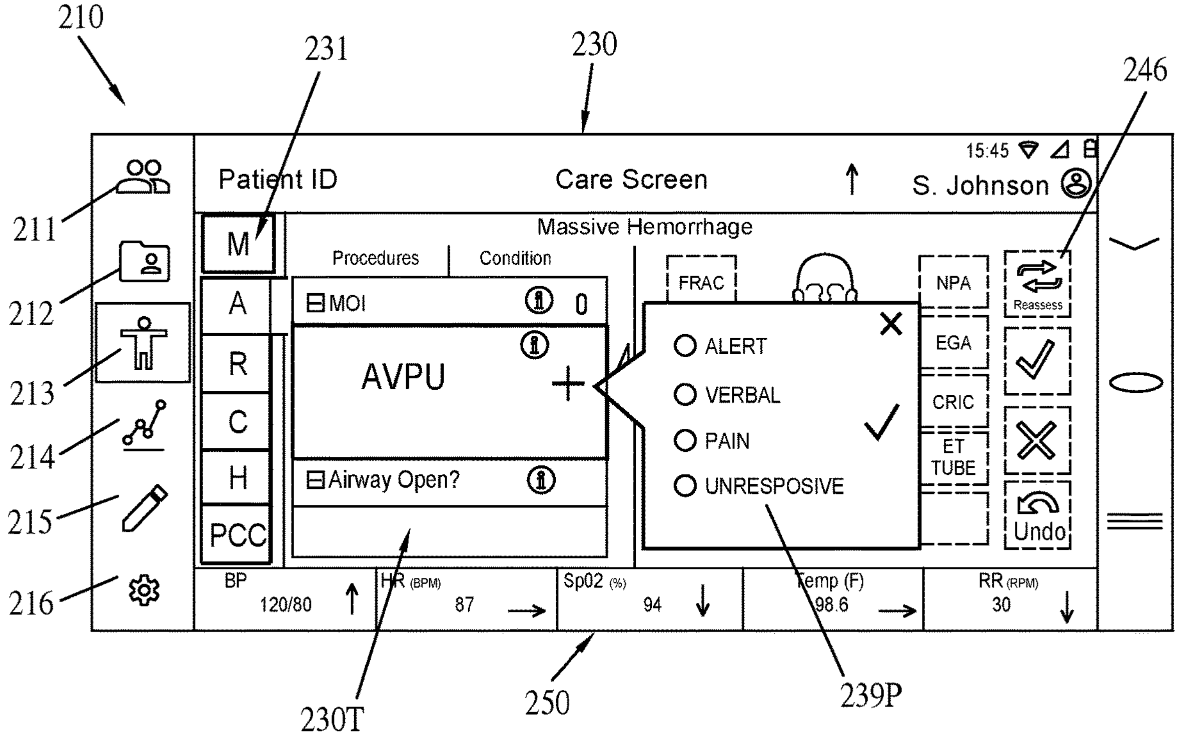

FIG. 2J-2L illustrate a slightly different interface designed for a user that has more experiences and allows quicker access to different parts of the assessments and interventions. As with FIGS. 2A-2I, there are a series of MARCH icons 231A (or tabs) along the left side of the care window 230A. In at least one embodiment, this set of icons (or other icons to reflect the particular assessment approach implemented) will be resident as the user interacts with different assessments. FIG. 2J illustrates an array of options for use in assessing the casualty and an array of options for interventions over a series of six columns (from left to right). In at least one embodiment, the selection of a MARCH icon 231, 231A will cause a message to be sent through the controller 102 to the medical knowledge handler 118 to create a fact of the selection, which results in the rules engine 124 to start an assessment.

In FIG. 2J, the first column includes a series of buttons that reflect typical presentations and will remain the same independent of the assessment tab selected. In an alternative embodiment, when the user selects one of these buttons, the medical knowledge library will send a question to the care window M tab asking the use where the bleeding is located while providing the option of selecting an existing location or identifying a new location. FIG. 2K illustrates how the question may be presented and the selection of a hemorrhage location on the homunculus figure. FIG. 2L illustrates how the medical knowledge library could use the user interface to solicit further information regarding the AVPU state of the casualty using a pop-up menu.

In FIG. 2J, the second and third columns include injuries that typically will be associated with a location flag that the user choose a location on the homunculus 242, and, in at least one embodiment, the selection of a button in the second column will impact the buttons illustrated in the third column. In at least one embodiment, the user interface will allow the user to add additional locations to the homunculus after having already submitted a response. In a further embodiment, if more than one question for an assessment tab requires a location, the options for the highest priority question will be displayed first. As illustrated in FIG. 2J, when there is more than one question requiring a location, each of the questions that require location will appear as a button in the second column.

In an alternative embodiment for when questions do not require a location, these questions will either appear in the second or third columns or be omitted. In at least one embodiment, the buttons will remain on that tab even if they have already been answered, and will reappear if the user leaves the tab and comes back. The medical knowledge library 120 will include a flag or other indicator in the assessments/procedures databases 128, 128A, 128B to indicate which column should display the question. In an alternative embodiment, this flag may also indicate that the question should be displayed in the sixth column. In a further embodiment when there is a question to be displayed on the normal care window 230A, but not on this button screen, that question could use a flag or other indicator indicating, for example, the zero column, which is not displayed in the interface example of FIG. 2J. An example of the flag or other indicator is the number of the column, for example questions that are already part of the first column will have a 1.

In FIG. 2J, the fourth and fifth columns are illustrated as including buttons for the treatments field in the procedure. In at least one embodiment, the order of interventions starts at the top of the fourth column through the bottom before going to the top of the fifth column and are selected based on the part of the assessment selected in the MARCH icons 231A. In an alternative embodiment, the intervention procedures provide a ranking or order of the interventions to be displayed. As with the other buttons, these buttons are toggleable, going from unknown, to completed, to not completed, and then toggling between completed and not completed.

FIG. 2J provides an example of how a user could inform the system that a tourniquet (TQ) was applied and its location on the homunculus without receiving a suggested treatment to take that action from the medical knowledge library 120. In an alternative embodiment, when a button is selected or long pressed in the fourth and fifth columns, the medical knowledge library 120 will retrieve the selected intervention steps and provide information for the user interface to display a menu asking if the user wants yes, no, or instructions on how to do the procedure. In an alternative embodiment, the user interface may include a button that will cause a list of the possible treatments under that tab to be retrieved from the medical knowledge library 120 such that if the user selects one treatment, the instructions for that treatment will be provided. In at least one embodiment, the instructions will be displayed in a normal care window 230 (for example, like that discussed in FIGS. 2F-2I or FIGS. 2K and 2L) and not on the interface illustrated in FIG. 2J. In at least one embodiment, this information tab is different than the 'i' buttons 233 discussed in other parts of this disclosure because it may display the more information section of each procedure (question or set of instructions).

In FIG. 2J illustrates an alternative or optional embodiment, the sixth and right most column is configured to display the negative and positive response for the most important question for the tab. These options should be in the conditions field in the procedures already. If there are more than two responses (radial pulse) there should be a pop out.

FIG. 2J also illustrates buttons that allow for the user to perform a reassessment button 246, also included in other user interface examples, for the casualty, for example when there has been a change in the casualty's condition; submit (e.g., green check mark 248) and cancel (e.g., red "X" 247) buttons; and an undo button 249 to request the last input be undone.

FIGS. 3A-3X illustrate an example of possible user interfaces that also assist in explaining the operation of the main system 100 and the medical knowledge library 120.

FIG. 3A illustrates an example of how the login screen might look for the system with FIG. 3B providing an example of the user interface for a user to change their password. FIG. 3C illustrates an alternative interface that requires entry of the password twice by the user before the user can log into the system.

Figure 3D:
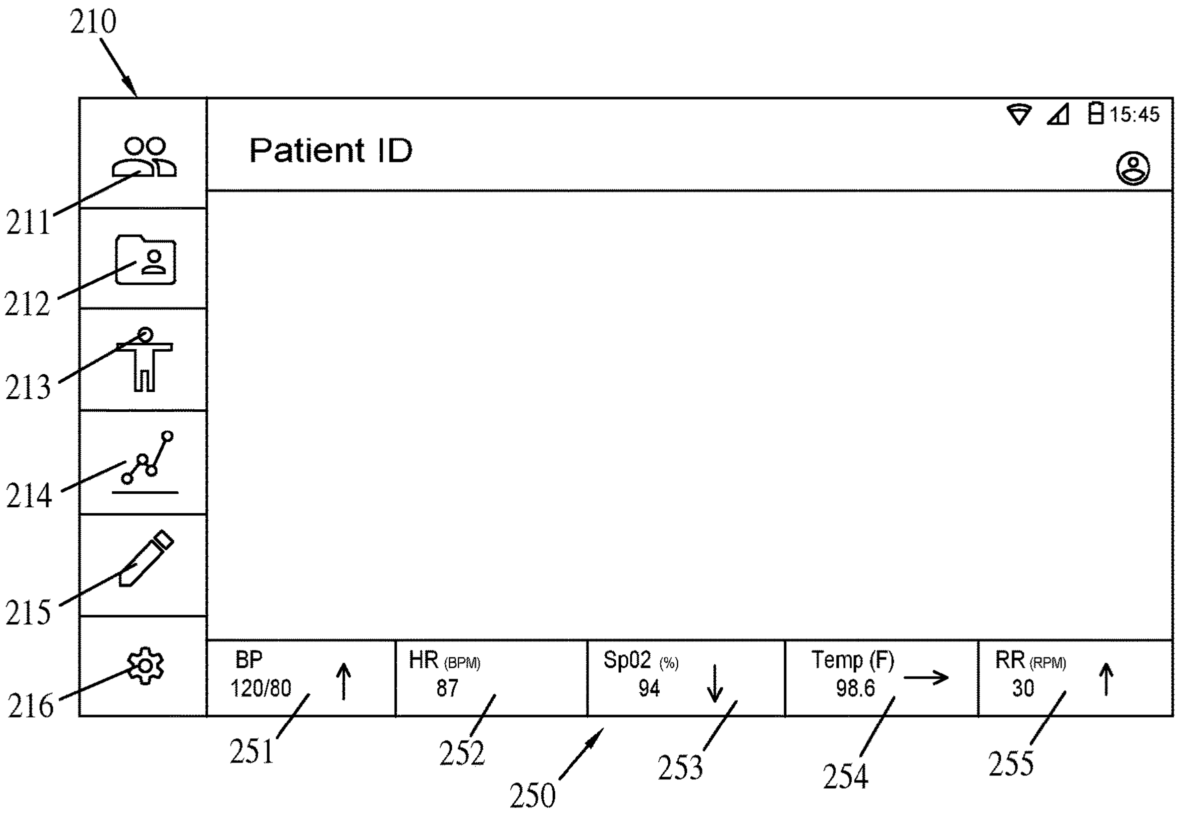

FIG. 3D illustrates a static icon menu 210 that includes a virtual ward icon 211, a casualty demographics icon 212, a care window icon 213, a vital-signs icon 214, a notes icon 215, and a settings icon 216. See, e.g., FIGS. 2A-2L and 4A-4D. The virtual ward icon 211 causes a retrieval of a list of the current individuals being treated (or patients) and, optionally, the ability to preload individuals into the system. In an alternative embodiment, the virtual ward icon 211 causes a retrieval of a list of all individuals in the database or in a further alternative, there is a roster icon to bring up that list of individuals like that illustrated in FIGS. 3E and 3F. Based on this disclosure, a similar virtual ward is included with the example user interfaces of FIGS. 2A-2L and 4A-4D.

Figure 3E:
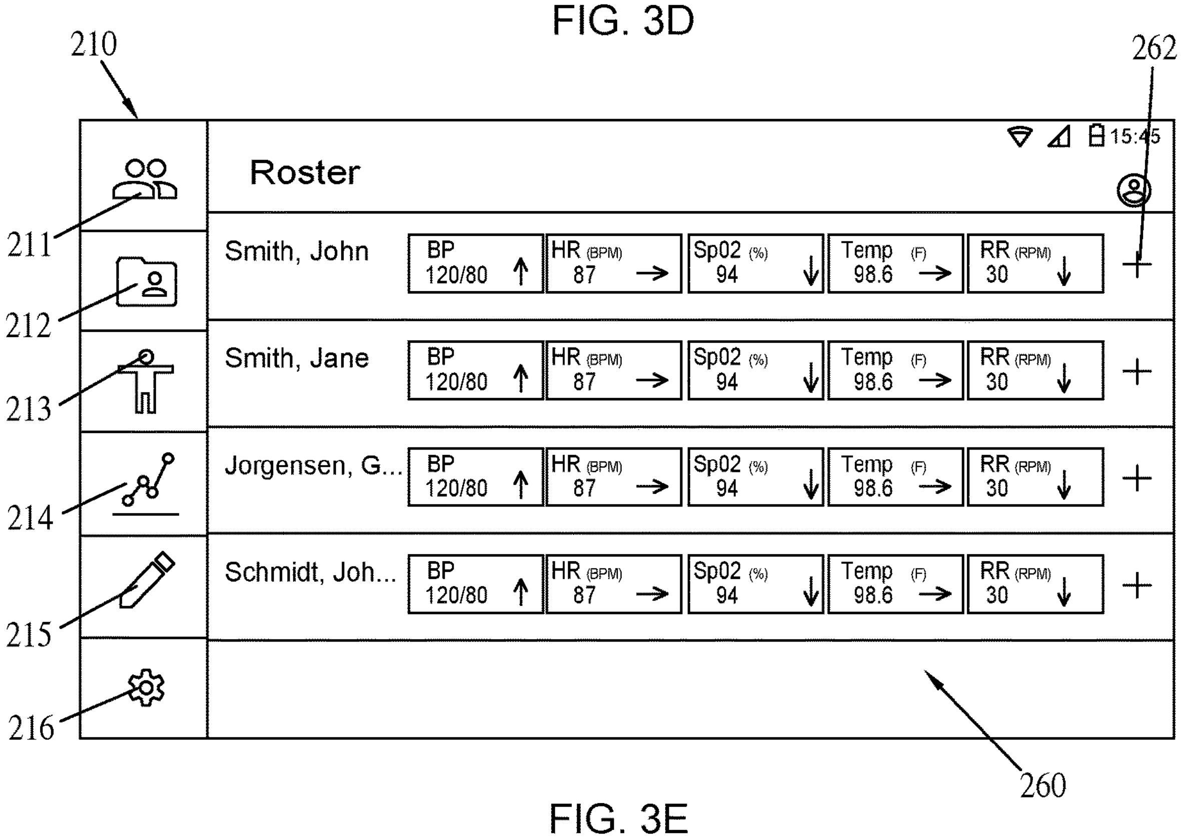
Figure 3F:
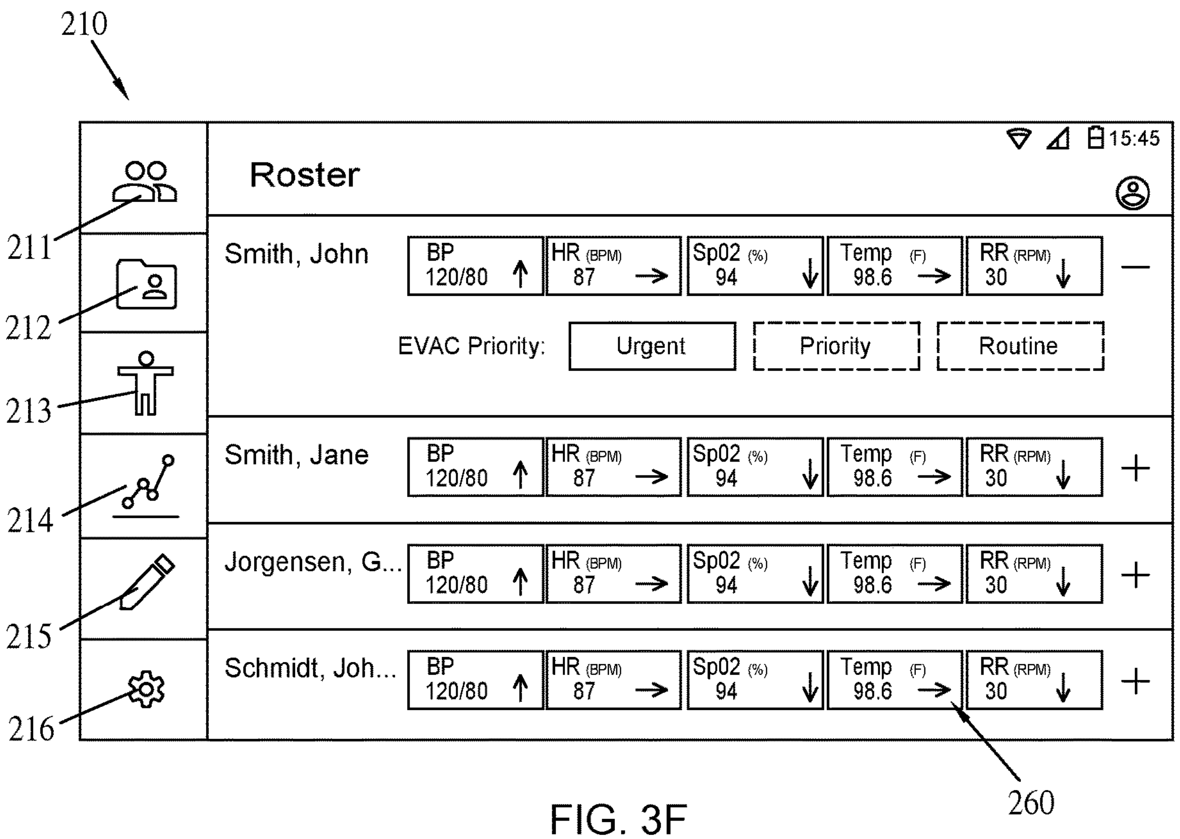

FIGS. 3E and 3F illustrate how the virtual ward may look and how the use of the "+" button 261 for an individual will expand the description to display additional information, which in FIG. 3F includes evacuation priority. Based on FIGS. 3E and 3F, a person having ordinary skill in the art should appreciate that different information may be displayed regarding the individual when expanded, for example a list of injuries and/or applied treatments. In at least one embodiment when the user selects an individual's name (or other identifier), the care window (e.g., FIGS. 2A-2L and 3I-3N) will become available to display particular information regarding the individual. FIGS. 3E and 3F also illustrates the use of color (e.g., red, yellow, and green) to provide a visual indication of the individual's state (e.g., providing a color frame around the casualty and/or color arrow to indicate any trend for a particular vital sign) and a user interface to request evacuation and at what priority.

Figure 3G:
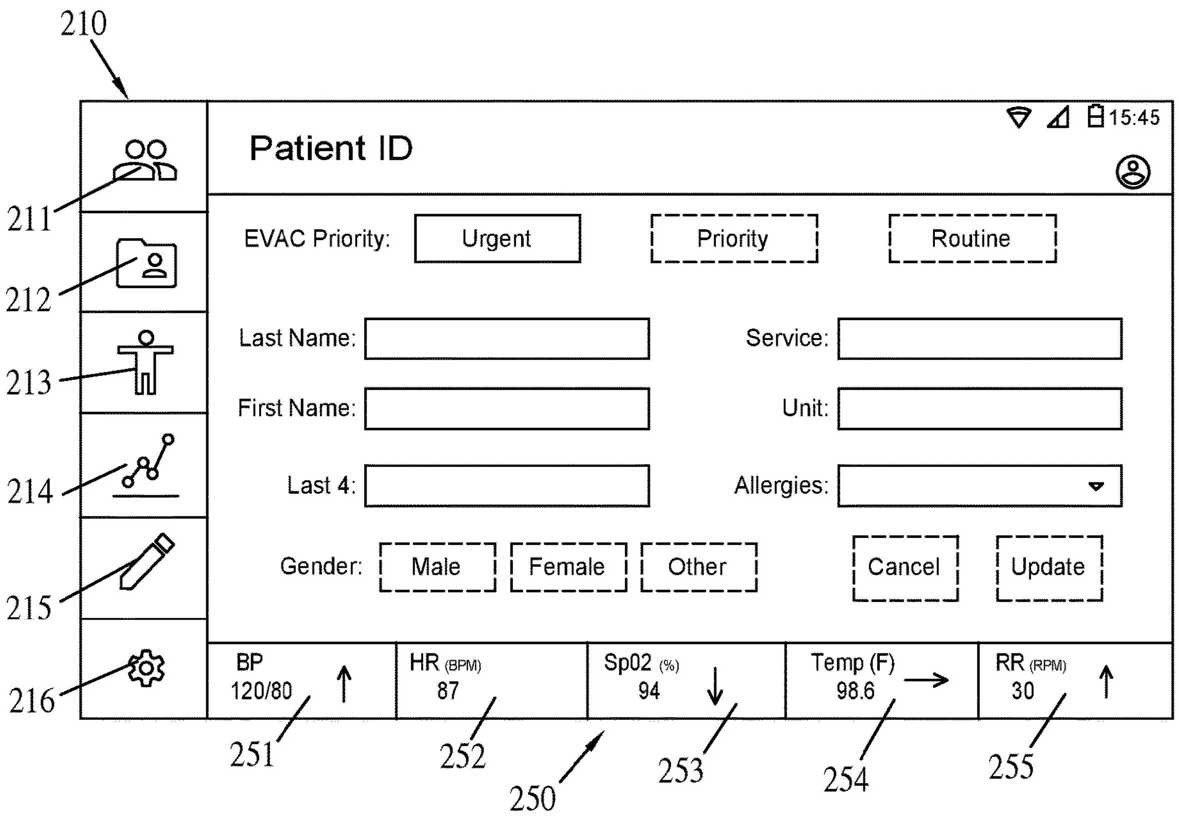
Figure 3H:
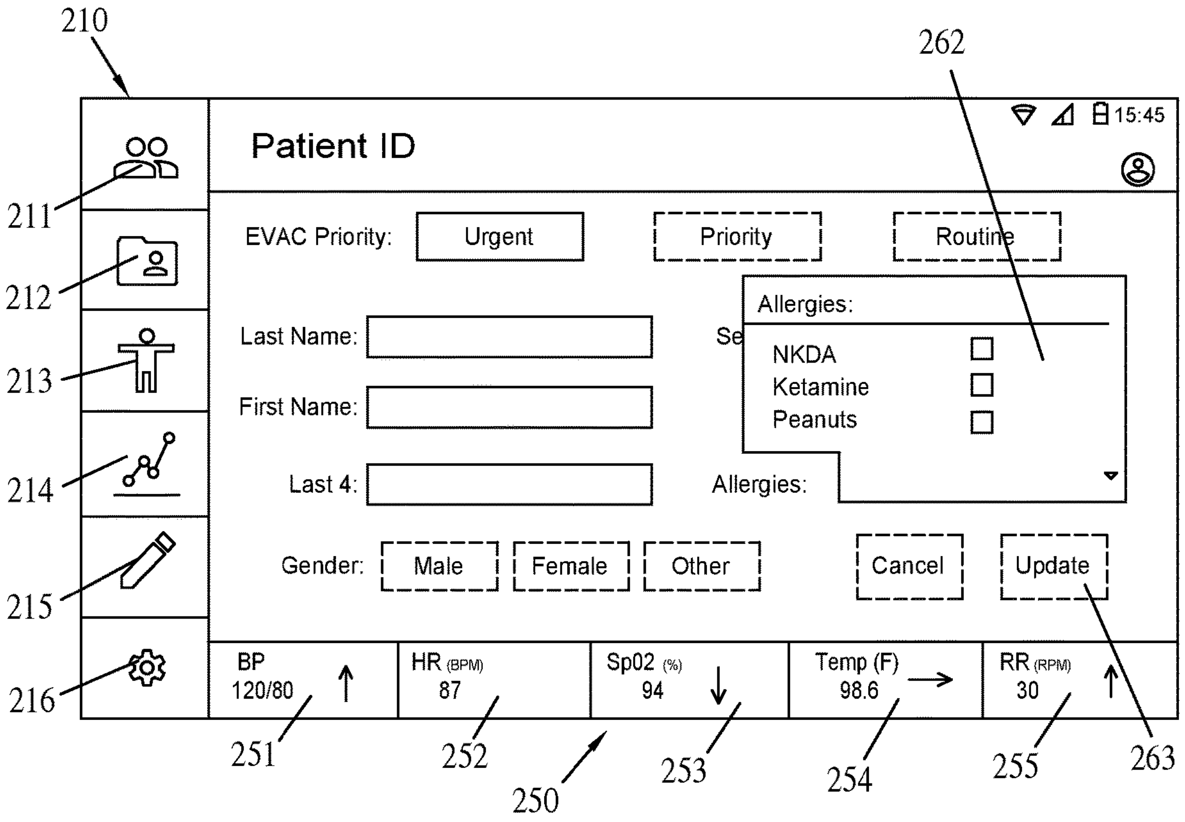

In at least one embodiment as illustrated in FIGS. 3G and 3H, the casualty demographics icon will bring up basic information for any casualties and may be populated based on the individuals in the virtual ward. These figures illustrate how the Patient ID screen could look to enter information regarding the casualty when the individual is not already present in the system. The illustrated user interface also provides another way for the user to select the evacuation priority of the individual, which in at least one embodiment may also or instead be set by the rules engine. Although "Last 4", "Service" and "Unit" fields are illustrated, a person having ordinary skill in the art should appreciate that these fields could be for other information (e.g., address or location information) or not included depending on the particular implementation. FIG. 3H also illustrates a user interface for the user to identify allergies for the individual, if known, through a pop-up window 262. The identification of allergies allow for the creation of a fact(s) regarding the particular allergy(ies) selected for the casualty and may impact proposed interventions. As illustrated by the "Update" button 263, the system can be configured to allow for the user to update the individual's information after entry, for example as time permits and/or new information is learned regarding the casualty.

FIGS. 2A-2L, 3I-3N, 3Y, 4A-4D, and 5C-5F illustrate different examples of the interface that may be brought up when the care window icon 213 is selected. The selection of the care window icon 213 opens a user interface to enter treatment/injury/conditions for the individual, select areas on a homunculus 242, and provide summary information regarding the individual. The vital-signs icon 214 will bring up an interface to view vital-sign measurements over time, and, alternatively, this data is presented as waveform data to provide a visual presentation as opposed to numbers. See, e.g., FIG. 5A. In a further embodiment, the user is able to select a point along the waveform to see the numerical value(s) for the vital-sign measurement(s). These illustrated interfaces include a drawer arrowhead icon 249 that when selected with cause the sections of the care window to expand or shrink the textual screen 230T.

Figure 3I:
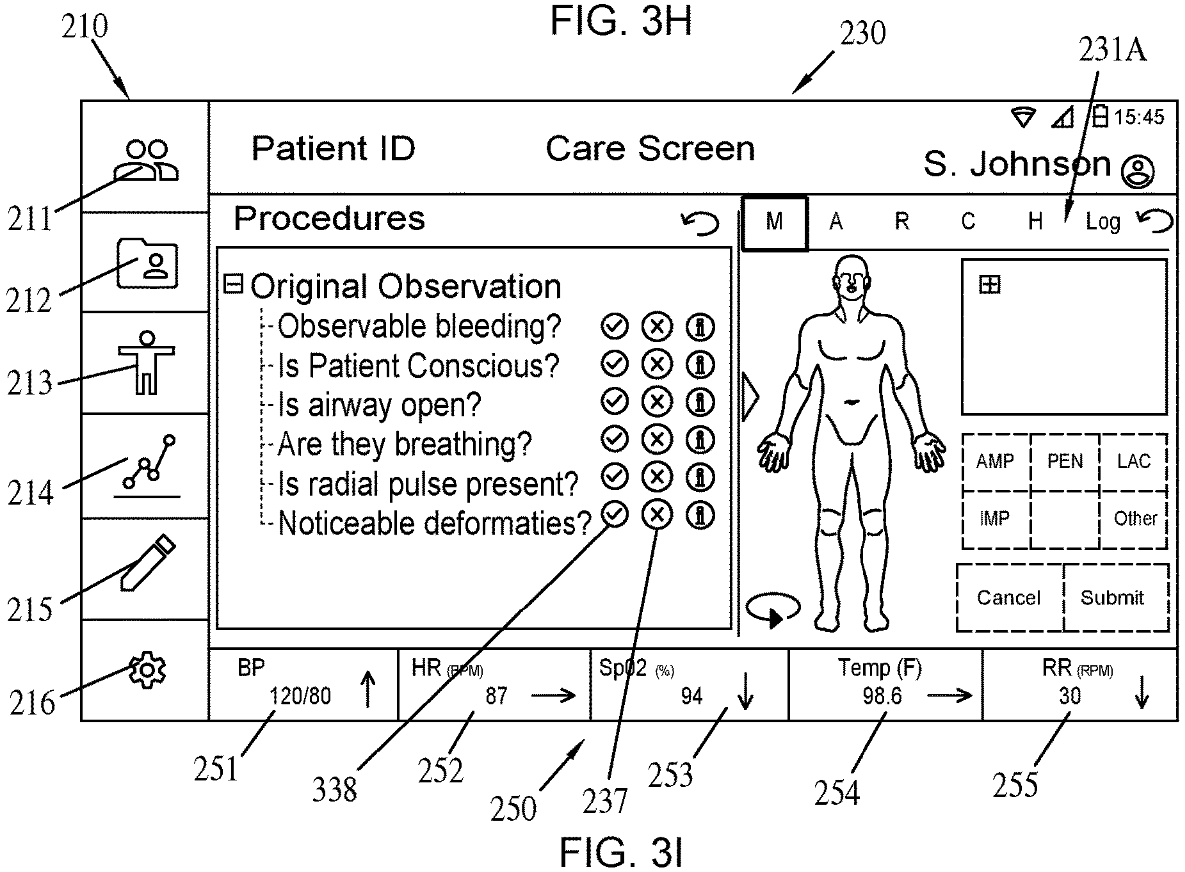
Figure 3J:
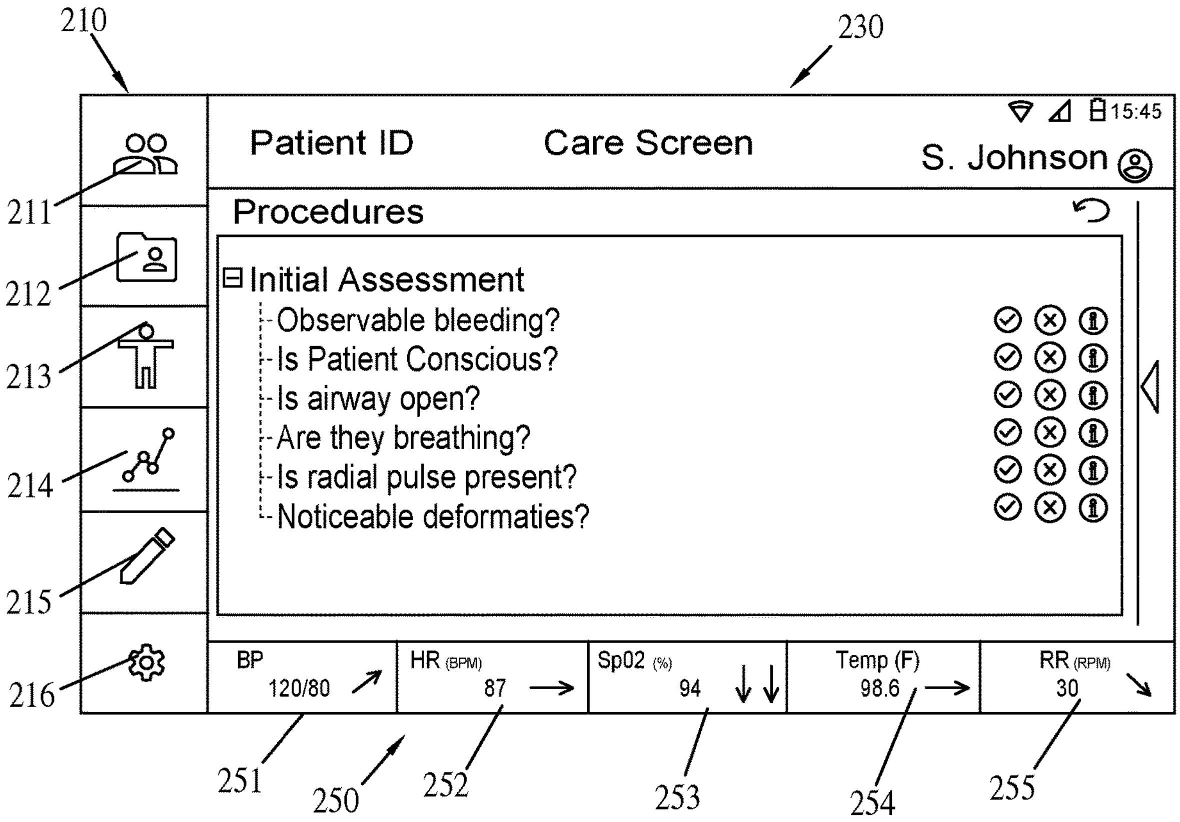
Figure 3K:
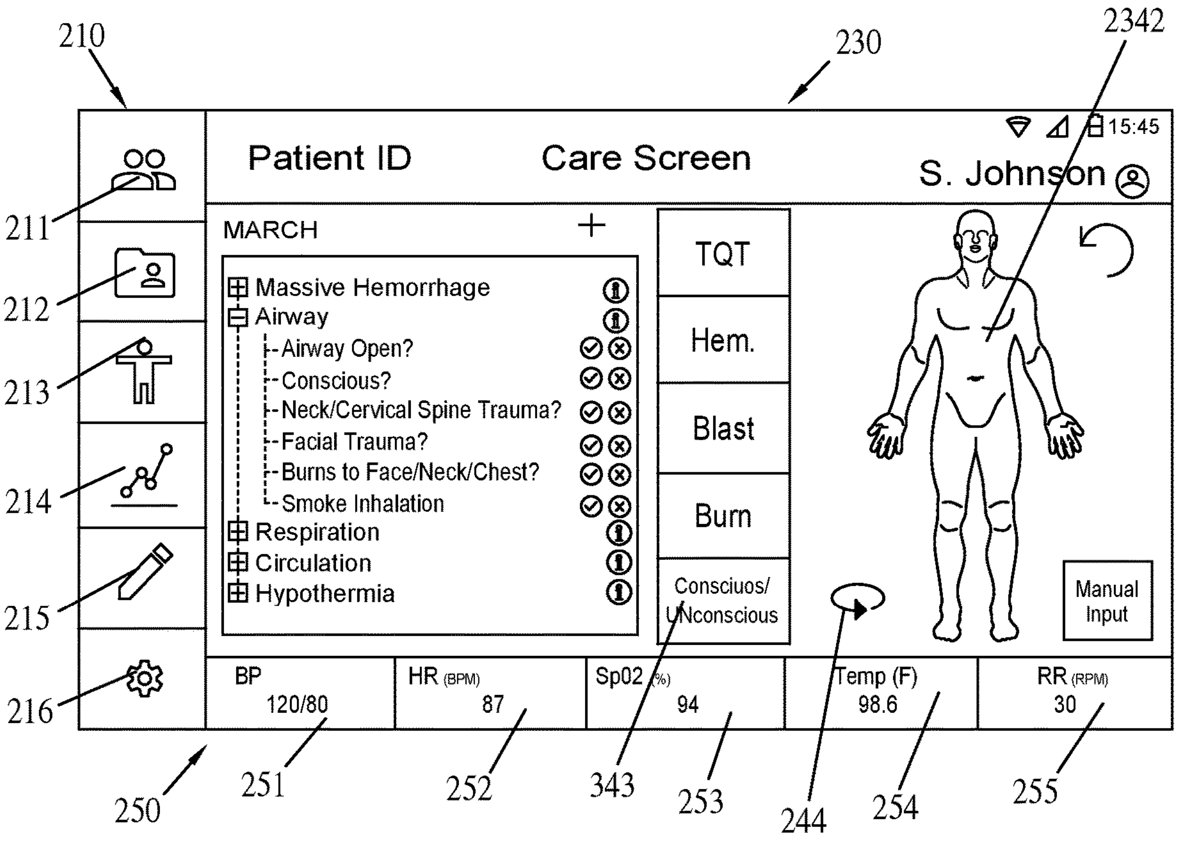
Figure 3L:
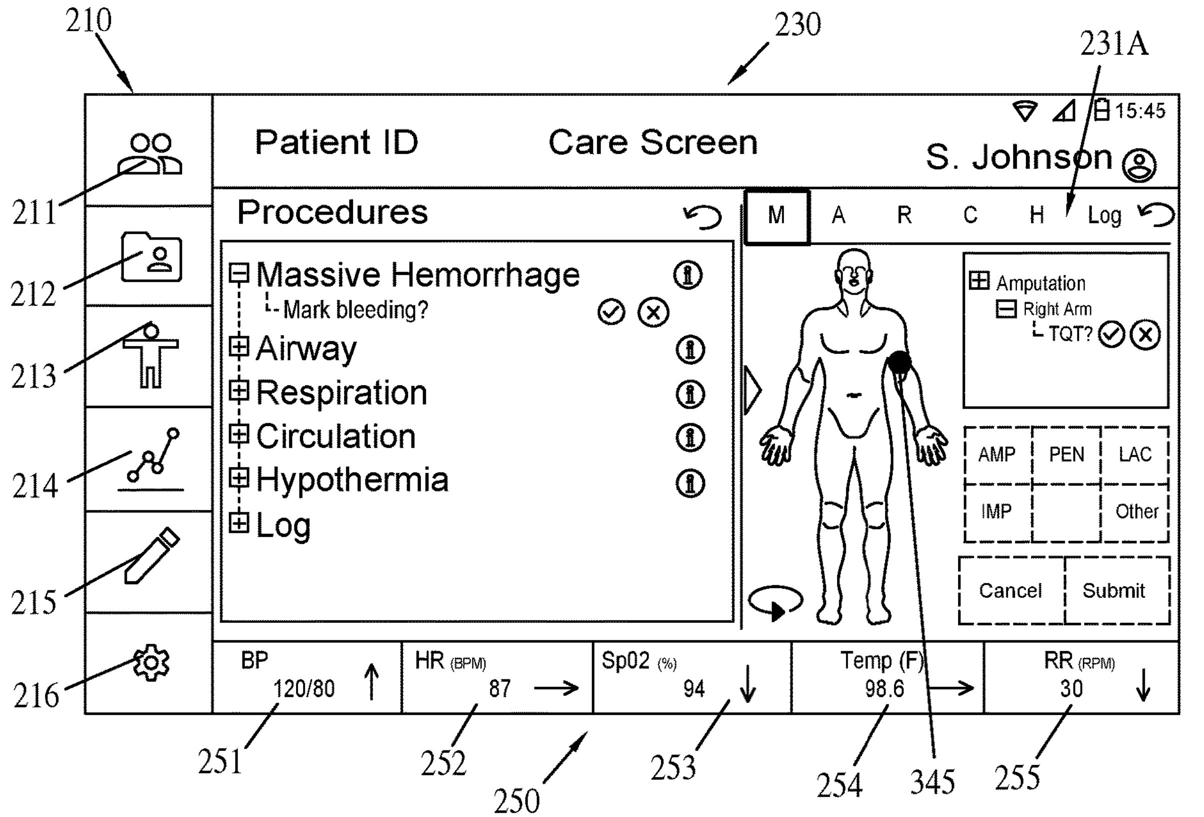
Figure 3M:
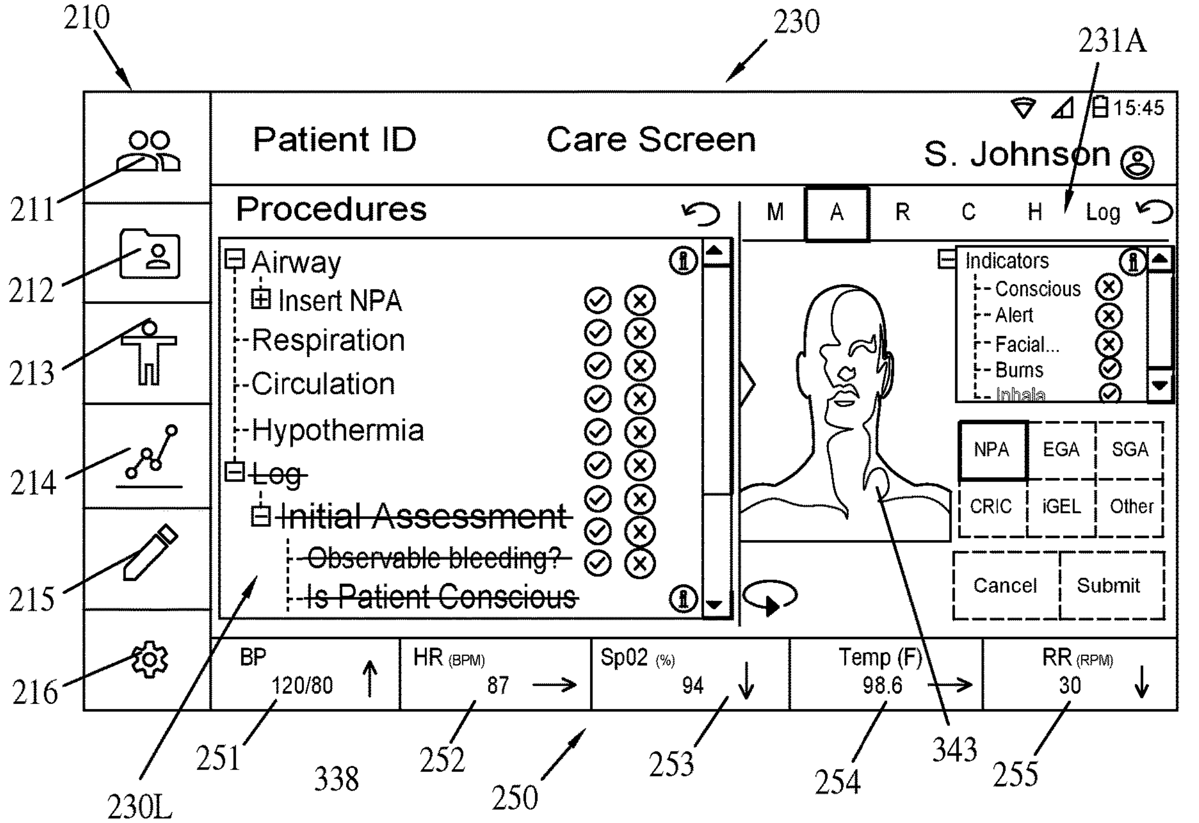
Figure 3N:
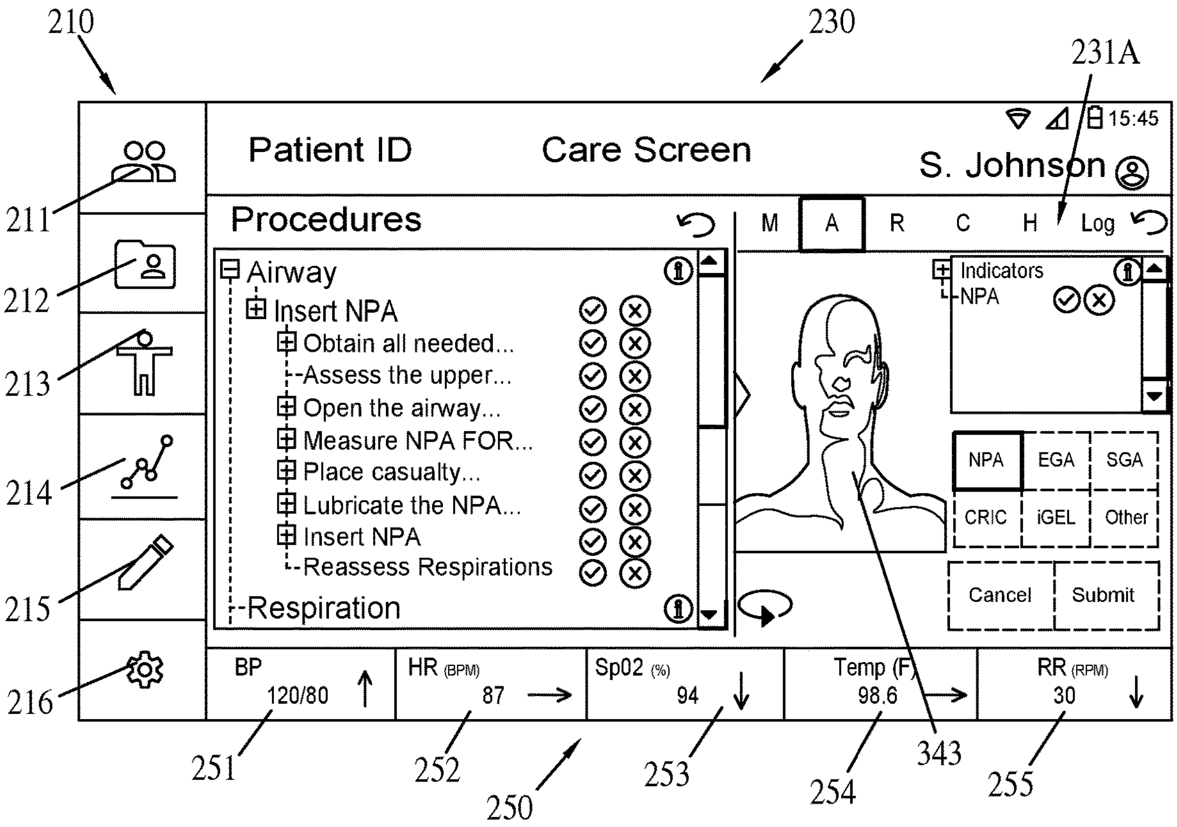

FIGS. 3I-3N illustrate examples of alternative care windows for using a MARCH assessment approach (FIGS. 3I-3K), the massive hemorrhage (M) observations (FIG. 3L), and the airway (A) observations (FIGS. 3M and 3N). Based on these screens, a person having ordinary skill in the art should appreciate that similar user interfaces could be used for respiration (R), circulation (C), and head injury/hypothermia (H) of a MARCH assessment or other approaches. As discussed above, the circled checkmark 338 and the circled "X" 337 will lead to a fact being sent when selected, and similarly the selection of a location on the homunculus 242 and injury type will lead to a fact being sent to the medical knowledge handler 118. In a further embodiment, color may be used for the checkmarks, "X", and "i", for example green, red, and another color, respectively. These four figures illustrate an alternative placement of the MARCH acronym 231A along the top right of the care window (as opposed to along the left side as illustrated in FIGS. 2A-2L) to assist the user through the evaluation of the casualty and collection of information to lead to the generation of facts. In at least one embodiment, each letter of the MARCH acronym 231A will be a tab that upon selection will bring up an appropriate screen to assist the user through the assessment and the injury and/or treatment options with the homunculus 242. As mentioned before, an experienced medic may log this information after performing the assessment and even after performing the initial treatment(s) while taking advantage of the PCC capabilities of the front end main system 100 or does not require the decision support at least at the initial stage. In a further embodiment, the system allows the user in such a circumstance to associate an earlier time with the event for the timestamp. In at least one embodiment, each assessment inquiry will be useful to the system for PCC and thus have facts that are dependent upon their entry to provide better treatment options.

FIGS. 3I and 3J illustrate an interface to enter initial assessments with a difference between them being that FIG. 3I illustrates a split interface between the textual section 230T and a homunculus section 240 while FIG. 3J illustrates an expanded textual section 230T that provides additional area in which to provide textual information. FIGS. 3I and 3J illustrate how the drawer arrowhead icon 249 can be used to expand the window that is displaying the procedures for the assessment and/or the treatment while minimizing an area that includes the homunculus 242. FIGS. 3I and 3K-3N illustrate a split interface while FIG. 3J illustrates a maximum view of the textual section 230T. FIG. 3K illustrates an alternative interface for entering initial assessments using the MARCH assessment approach by selecting each letter of MARCH to move through the evaluation for massive hemorrhage, airway, respiration, circulation, and hypothermia injury(ies). In at least one embodiment, as the user progresses through the MARCH assessment, the system will provide recommended treatments based on the ongoing medical information being provided.

Both FIGS. 3I and 3K illustrate how the homunculus 242 may be used to enter the type of injury and the location of the injury on the casualty being examined by selecting the spot on the figure as to the location. In at least one embodiment, the interface allows the user to rotate the figure (244) to another viewing angle, or, in an alternative embodiment, front and rear views of the homunculus 442 are displayed as illustrated in these figures and FIGS. 4A-4D. In an alternative embodiment, instead of or in addition to an injury being entered, the type of treatment performed is entered such as use of a tourniquet, a bandage, an IV, and/or an airway/chest tube. FIG. 3I illustrates amputation (AMP), penetration (PEN), laceration (LAC), impalement (IMP), and other; while FIG. 3K also illustrates a selection menu 343 with a tourniquet (TQT), hemorrhage (Hem.), blast and/or shrapnel (Blast), burn (Burn), and consciousness state (Conscious/UNconscious). In the illustrated interface, the consciousness state is a toggle between conscious and unconscious as illustrated by FIG. 3K instead of a drop down or pop-up window 239P with A, V, P, or U as illustrated, for example, by FIG. 2L. Alternatively, different treatments/conditions may be identified and be options for interacting with the homunculus. Although both of these illustrated interfaces use the MARCH assessment approach, other evaluation approaches could be used. In at least one embodiment, if the medical knowledge library 120 has information regarding an information inquiry, then it will mark that inquiry based on that information, and in a further embodiment, this will be subject to confirmation by the user.

FIGS. 3L-3N illustrate how a higher level can be expanded to list sub-steps for the user based on their skill and/or comfort level by the selection of the expansion "+" icon 235 and likewise selection of the "−" icon 236 will minimize the particular list. As discussed above in at least one embodiment, there are three levels of information. FIG. 3L illustrates a selection by the user of the amputation injury (AMP) and a location on the arm 345 where the amputation has occurred resulting in the injury being identified and an inquiry as to whether the treatment has been performed, which in this example is the application of a tourniquet.

FIGS. 3M and 3N illustrate a user interface for entry of information regarding the casualty's airway and includes the head and neck region 343 (as opposed to the entire homunculus) to make it easier to identify the location of an injury(ies) and/or a treatment(s). The adjustment as to how much of the homunculus is displayed is an example of how the user interface can be adapted to present more relevant information to the user based on the selection(s) made by the user. In the upper right corner of FIG. 3M, the identification of the casualty's state is presented, which in this circumstance includes the intervention to insert an airway in the textual window 230T. FIG. 3N illustrates how the sub-steps for performing a particular treatment may be listed out, which in this illustration is the insertion of an NPA. FIG. 3M also illustrates an example of expansion of a log 230L for the casualty showing the steps performed already with strike-throughs and grayed out, but in at least one alternative embodiment, this provides a way for the user to adjust a previously entered assessment in the situation where there has been a change in addition to using the injury/treatment entry side of the care window. Based on this disclosure, a person having ordinary skill in the art should appreciate the previously discussed "complete" section 230C is analogous to the illustrated "log" section 230L, which is an alternative approach.

Figure 3O:
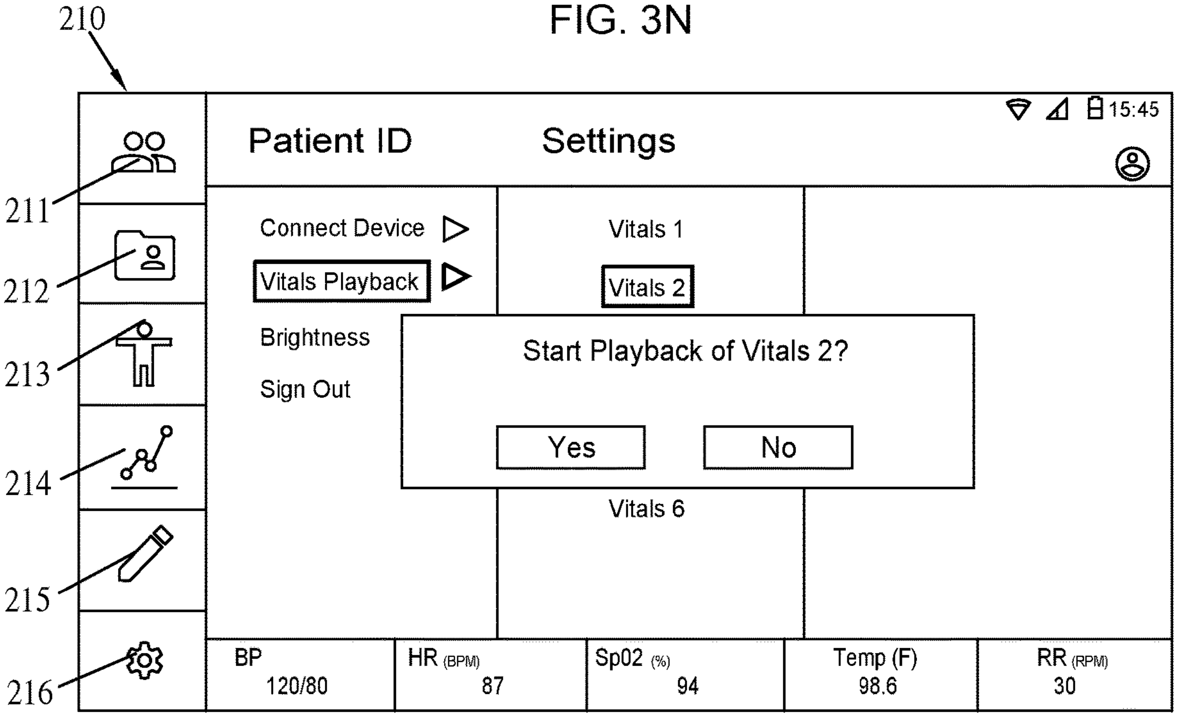

FIG. 3O illustrates an alternative embodiment where previously recorded vital-signs may be replayed to test and/or debug the system performance.

Figure 3P:
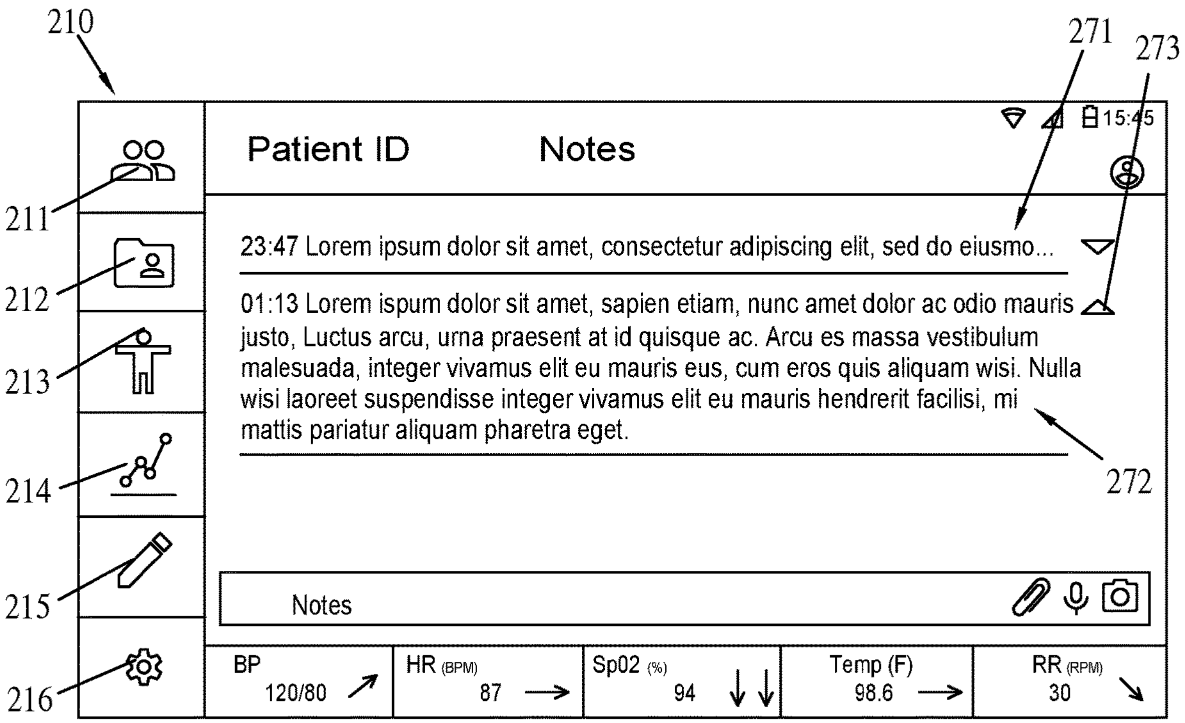
Figure 3Q:
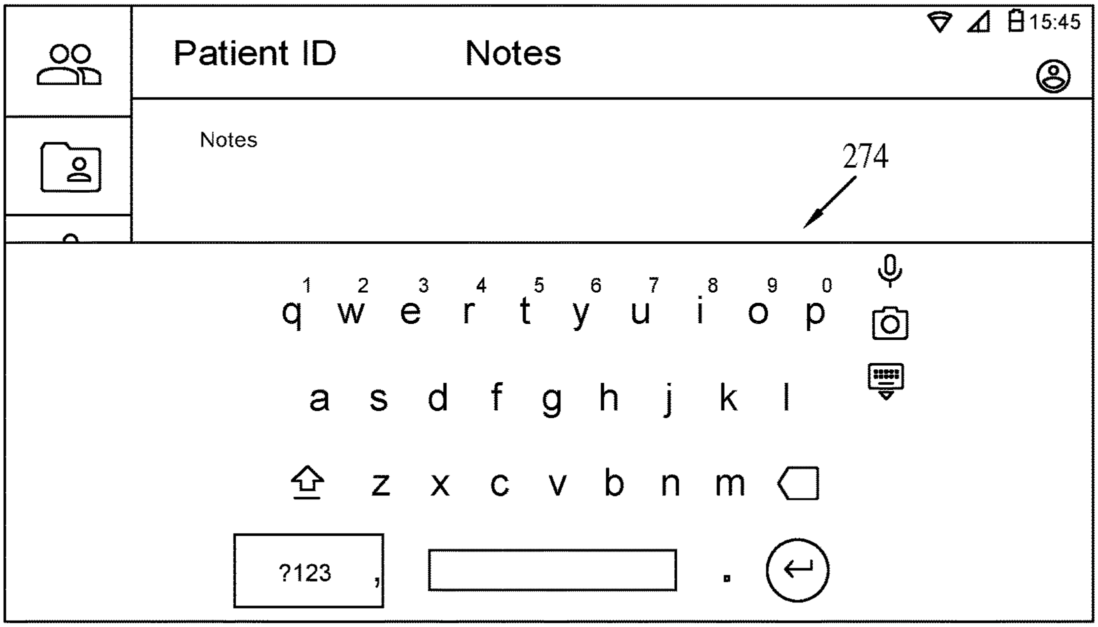
Figure 5G:
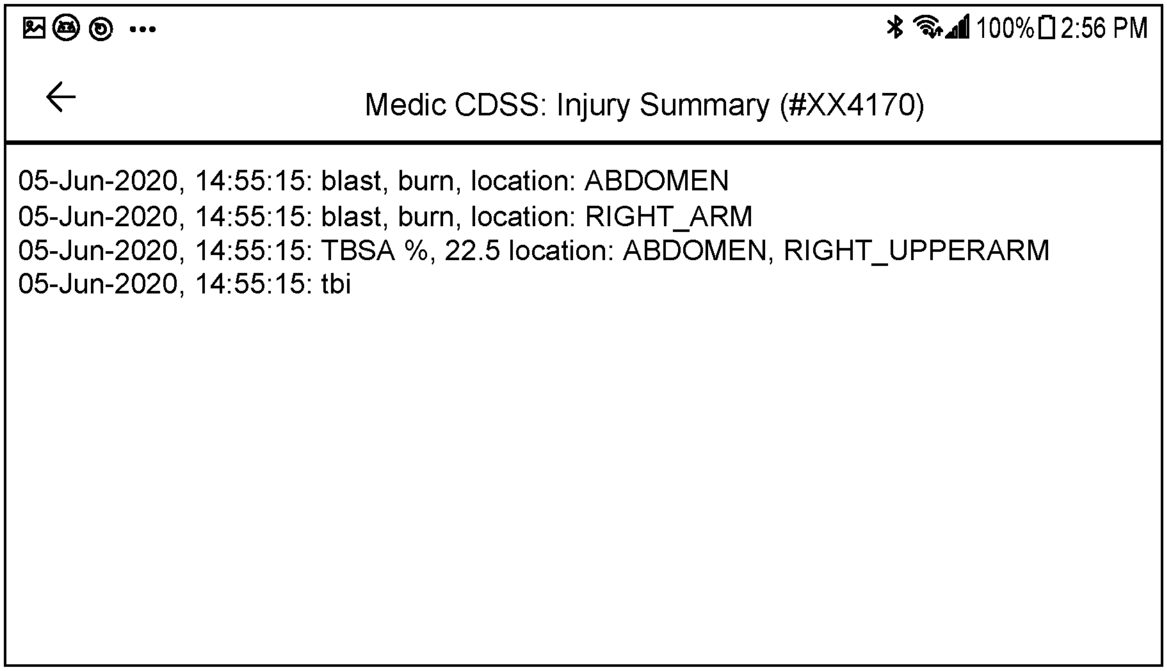
Figure 6F:
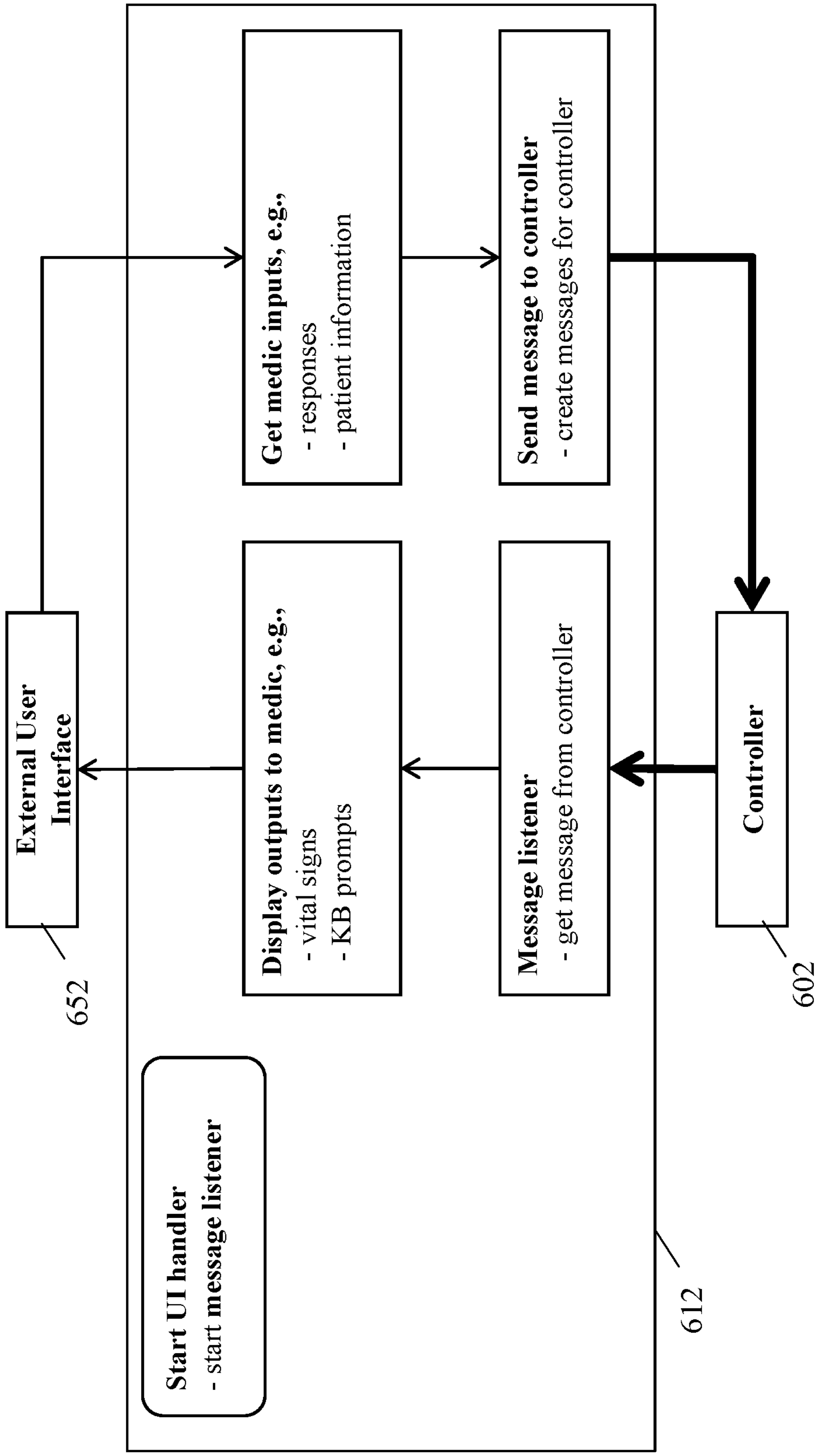

Selection of the notes icon 215 will retrieve an interface, for example one like that illustrated in FIGS. 3P and 5G to allow for entry of free text and/or upload files and/or images about the individual. FIG. 3P also illustrates an example of how previous notes may be displayed using a 1 line preview 271 (the note at 23:47), which may be a file name or an image name, that can be expanded to show the entire note 272 (the note at 01:13) using an expansion arrow icon 273, which could be replaced with "+" and "−" icons. In at least one embodiment, the notes are sorted in chronological order. In an alternative embodiment, the notes are searchable by the user. In a further embodiment, the free text will be mined by the system (e.g., the controller or a mining module) for key terms using, for example, natural language processing to populate and otherwise provide medical information to the local database 1404 and/or the medical knowledge library 120. In a further embodiment, the mining would occur when the system was in a quiet state or offline. FIG. 3Q illustrates an example interface for entry of a note using a virtual keyboard 274.

Figure 3R:
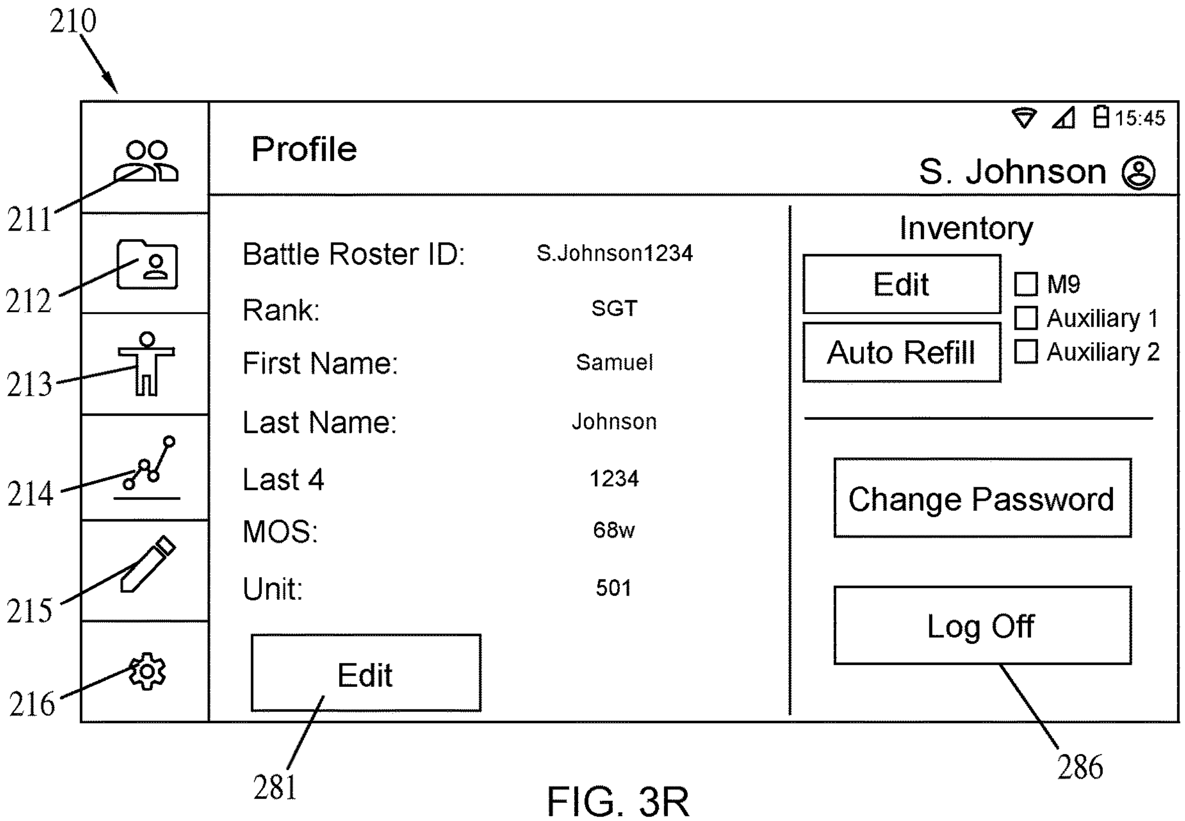
Figure 3S:
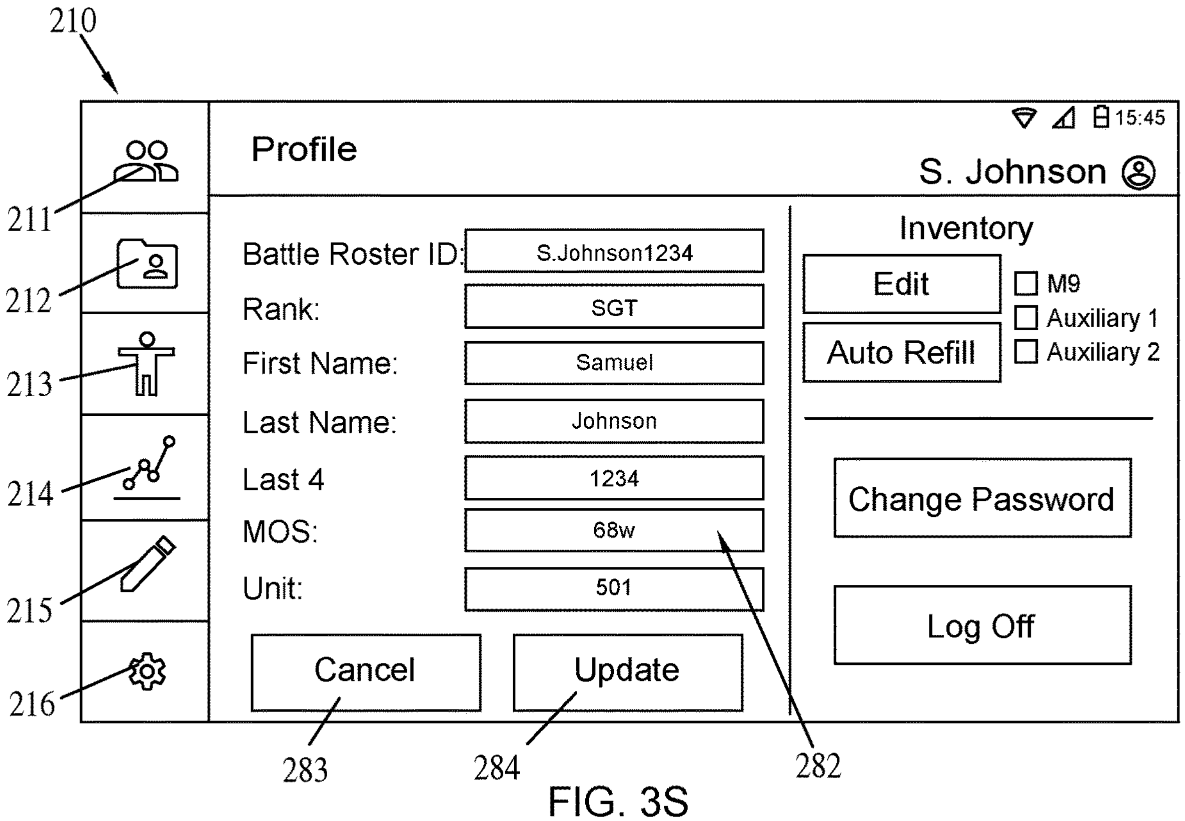
Figure 3T:
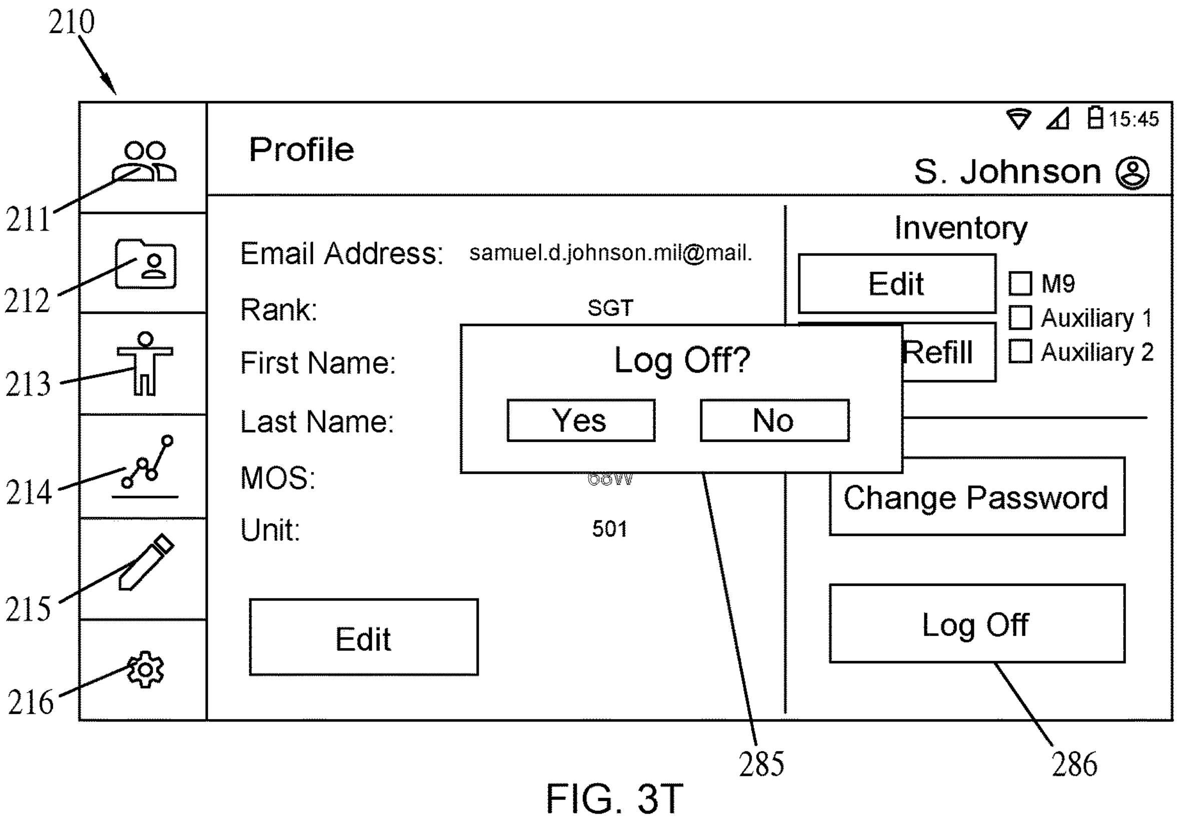

FIGS. 3R-3T illustrate the settings interface for a particular user profile. FIG. 3R illustrates an example of the initial interface displayed in response to the settings icon 216 being selected that includes a profile of the user, which is editable by selection of the edit button 281 to bring up the user interface illustrated in FIG. 3S with editable fields 282 and cancel and update buttons 283, 284; inventory section, a change password option, and a log off option 285 accessed through the log off button 286 that leads to FIG. 3T. It should be understood by a person of ordinary skill in the art that the profile may include different fields and information types. In at least one embodiment, the Military Occupational Specialty (MOS), which may be replaced by a civilian equivalent, provides a fact to be used by the rules engine when determining treatment options because it will be indicative of the skill level of the user. As a person of ordinary skill in the art will appreciate based on this disclosure, there are several medical treatments that require an advance skill set to be able to successfully perform beyond sheer luck, and as such the rules engine may exclude from consideration treatment options beyond the skill level of the MOS. In a further embodiment, there may be a field to indicate the experience level of the user beyond that of the MOS as this made increase the accuracy of any limitations as to treatments. In an alternative embodiment, the system will allow this to be overridden by the user.

Figure 3U:
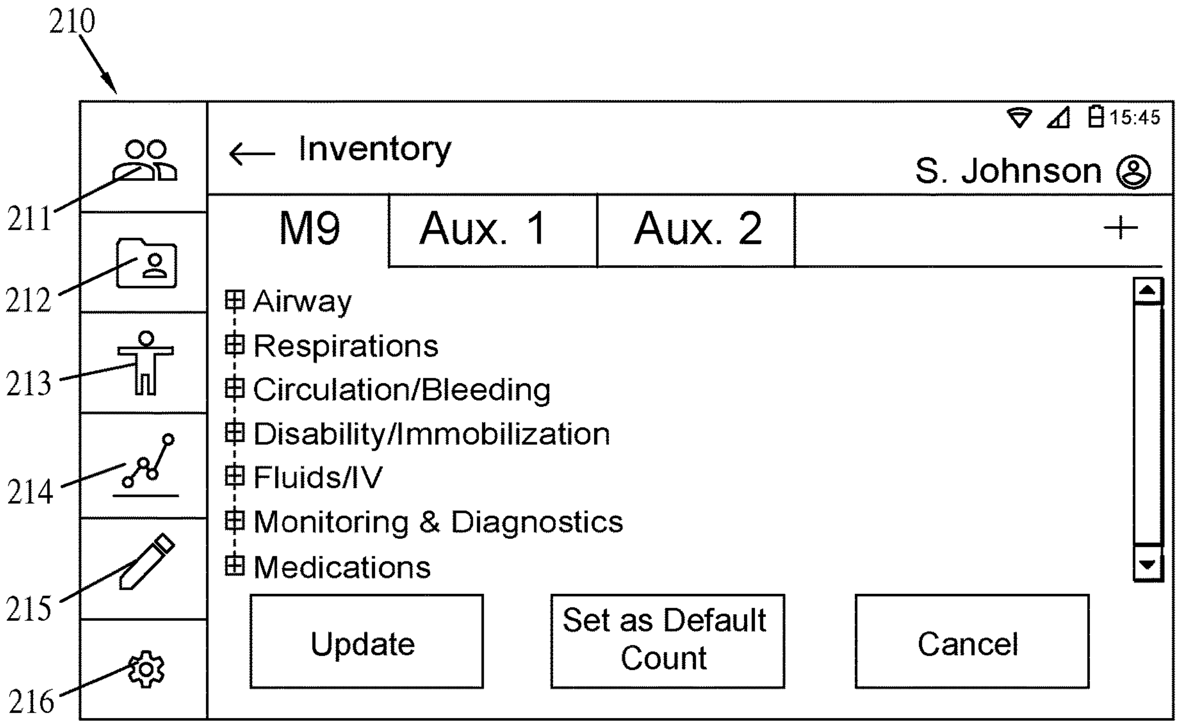
Figure 3V:
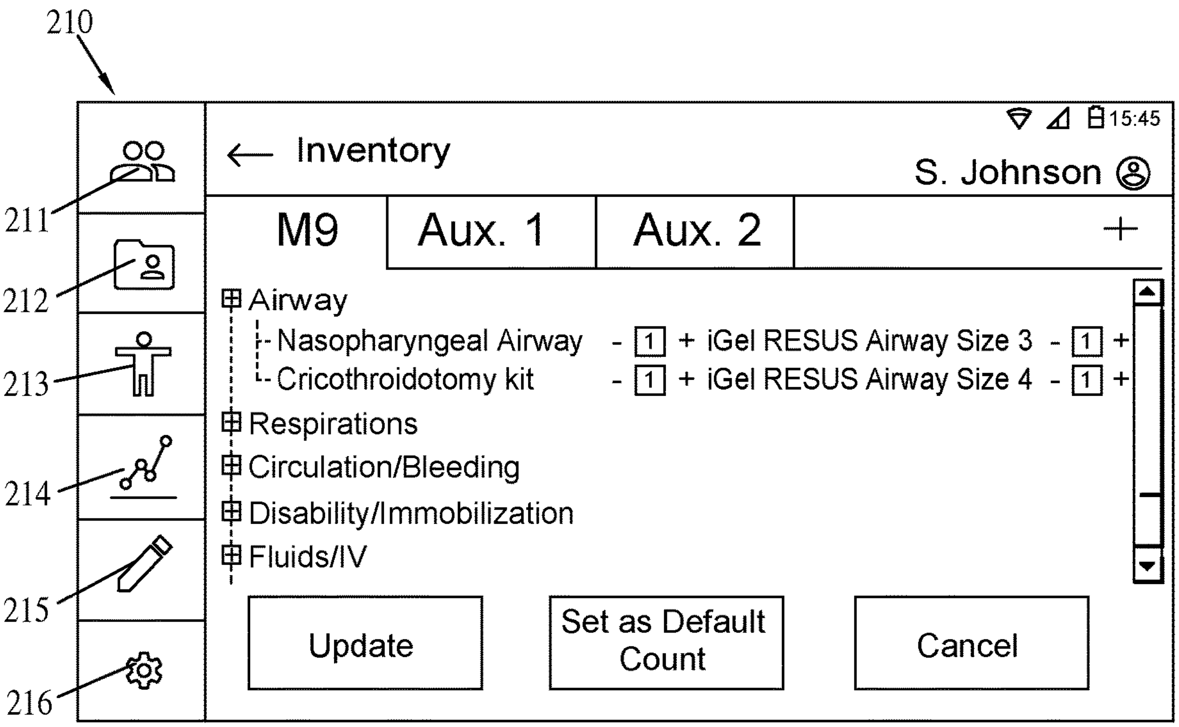
Figure 3W:
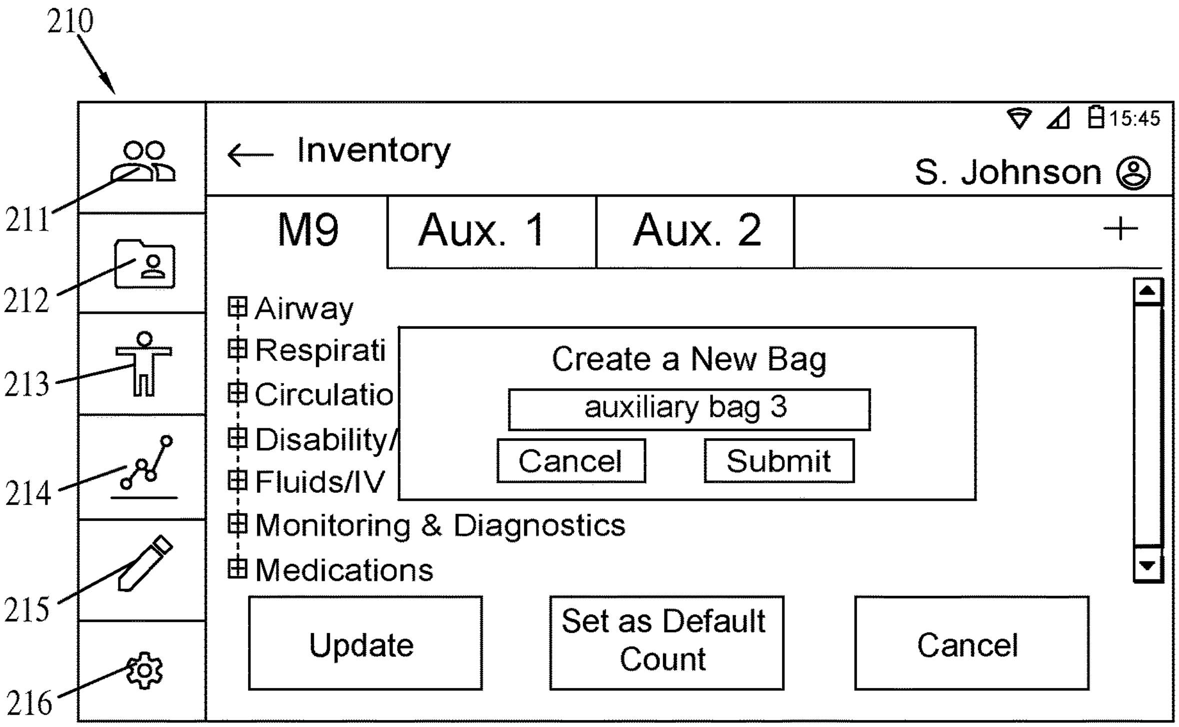

FIGS. 3U-3W illustrate examples of interfaces for handling inventory of medical supplies for the user. In a further embodiment, the main system 100 allows the user to adjust the inventory in the situation where medical supplies have been lost, damaged, or destroyed in the user's current environment. These figures illustrate the presence of three collections of medical supplies: a M9 medic bag, a first auxiliary bag, and a second auxiliary bag. It should be readily apparent to a person of ordinary skill in the art that other medic bag configurations could be preloaded into the system in addition to the creation of a medic (or first responder) specific bag as illustrated in FIG. 3W. FIG. 3V illustrates how the inventory may be viewed based on category where the medical supplies (or items) are categorized by use, for example airway (which has been expanded to show the airway medical supplies), respirations, circulation/bleeding, disability/immobilization, and fluids/IV.

In at least one embodiment, selection of the circle "i" icon 233 will retrieve additional information like that illustrated in FIG. 3X.

In at least one embodiment, as the user switches between interface screens the identified patient remains the same unless a new individual is selected from the virtual ward or, alternatively, by tapping on the patient id to bring up a selection list and/or other selection interface.

FIGS. 2A-2H, 2J-2L, 3G-3J and FIGS. 4A-4D illustrate examples of a vital-signs footer 250 along the bottom of the interface. The illustrated vital-signs footer includes blood pressure (BP) 251, heart rate (HR (BPM)) 252, blood oxygen levels (SPO2(%)) 253, temperature (Temp (F)) 254, and respiratory rate (RR (RPM)) 255. If a particular vital-sign is not available, then that vital-sign can be left blank or the most recent reading provided, or, alternatively, omitted from the display. In at least one embodiment, the controller provides the vital-sign measurements to the interface based on vital-sign measurements from medical monitors; however, in at least one embodiment, the vital-sign measurement may be manually entered by the user, for example by selecting the vital-sign to open a window to entered the manual vital-sign measurement. Based on this disclosure, a person of ordinary skill in the art should appreciate a different mix of vital-sign measurements may be displayed and/or alternatively the order of the vital-sign measurements may be adjusted, for example with the sensor derived vital-sign measurements being grouped together and the manually entered vita-sign measurements being grouped together. In at least one alternative embodiment, a trend for the vital-sign measurement is provided with an arrowed line 256-258 (e.g., FIG. 2J), which optionally may be color coded (e.g., red (257), yellow (258), green (256)) to indicate whether a trend is such that closer monitoring is required and/or troubling independently or in conjunction with other facts being processed by the medical knowledge library or, alternatively, an external AI system. FIG. 5A illustrates an alternative approach for displaying the vital-sign measurements. In at least one embodiment, the vital-signs are the last reading provided by an external system(s). In alternative embodiments, the displayed vital-signs may be provided by the facts repository or, alternatively, retrieved from the system database 104 by the controller 102 in response to a message from the medical knowledge library 120. In a further embodiment to the medical knowledge library 120 providing the vital-signs, the medical knowledge library 120 will provide a trend based on multiple or a series of facts for each vital-sign, if available. If the vital-signs are retrieved from the database 104, any trends may be determined by the controller 102, for example based on a comparison of two or more readings for each vital-sign.

FIG. 3Y illustrates an example of how a course of treatment and an injury/condition may be presented together to the user allowing for expansion of any step by the user and/or the ability to request additional information regarding the particular treatment step or, alternatively, during a training session. Similar to the other interfaces, the check selection icon 238 can be a yes and selection of "X" icon 237 can be a no.

In at least one embodiment, the treatments are color corded based on priority, for example using the stop light coloring of red, yellow, and green, and/or alternatively there is a visual identifier or symbol used to identify priority, for example when the user is color blind. In at least one embodiment, as the treatment is performed, it is marked as being completed, for example by crossing it out or changing its color, and/or relocated in the list of treatments as illustrated in FIG. 4D when compared to FIG. 4C. In at least one embodiment, where there are multiple injury/condition types, they can be presented in a nested structure. In a further embodiment, the interface allows the user to undo an entry in case of a data entry error, for example using the undo button 232.

FIGS. 4A-4D illustrate an alternative interface approach. The illustrated interfaces were implemented using Kotlin language for resilience purposes. These figures illustrated an alternative way to display the homunculus by showing front and rear views.

FIGS. 5A-5G illustrate another alternative interface approach that includes a different side menu 510 that includes icons/buttons for MAIN, INFO, INJURY, VITALS, TREAT, FLUIDS, MEDS, and NOTES. The interface illustrated in FIGS. 5C and 5D are examples of how the user interface could be implemented to allow the user to enter the injuries and treatments and use the front end main system 100 more as a documentation system and/or a long term casualty care system.

FIG. 5A illustrates a system user interface that displays vital-sign data (e.g., SpO2, heart rate, and blood pressure) provided by a vital-signs monitor or through the user interface accessible through the VITALS menu button. FIG. 5B illustrates a user interface for display and entry of patient information, which is accessible via the INFO menu button. FIG. 5C illustrates an example of the user interface reached by selecting the INJURY menu button to enter the type and location of the injury or injuries for the casualty. FIG. 5C also illustrates an example of the use of a switch for the selection of a variable for the airway being open or obstructed and the casualty being in shock or not. FIG. 5D illustrates the user interface reached via the TREAT menu button to display potential treatments that have been applied. FIG. 5E illustrates a pop-up menu with how to apply a tourniquet, for example in response to entry of a hemorrhage injury in the interface illustrated in FIG. 5C or selection of a tourniquet in the treatment interface of FIG. 5D. FIG. 5F illustrates the user interface reached via the FLUIDS menu button to allow for entry of provided fluids and blood products including the type and amount. In an alternative embodiment, what medications were administered could be entered through a similar interface to FIG. 5F by selecting the MEDS menu button. FIG. 5G illustrates an interface reached via the NOTES menu button for entry of free text about the casualty.

In at least one embodiment, the controller 102, the medical knowledge handler 118, and the medical knowledge library 120 (while in other embodiments, it is the medical knowledge handler 118 and the medical knowledge library 120) utilize a messaging structure to support the facts used by the rules engine 124. Examples of a messaging structure by class are as follows:

| Template (Class) | Structure |
|---|---|
| Vital Sign | name, patientid, value, time, previous list, trend |
| Mode of injury | name, patientid, location, value, time |
| Injury | name, patientid, location, state, time, previous list |
| Condition | name, patientid, location, state, time, previous list, trend |
| Evaluations | name, patientid, location, priority, value, time, supplies, medic level, previous list |
| Treatment | name, patientid, location, priority, value, time, supplies, medic level, previous list |
| Medication | name, patientid, priority, value, time, dose number, dose, unit, method, supplies, medic level, previous list |
| Fluids | name, patientid, priority, value, time, unit number, type, amount, method, supplies, medic level, previous list |
| Request | class, name, patientid, location, priority, time |
| Update | class, name, patientid, location, value, time |
| Response | class, name, patientid, location, priority, state, time, value |

The name would identify what type of item is being referred to by the message (e.g., heart rate, tourniquet, saline, hemorrhage, etc.). The patient id would identify the casualty for which the message relates. The location would identify the location of the item. The value, time, and amount would relate to characteristics of the class. In an alternative embodiment, evaluations and treatments can have multiple steps and the value in the template may refer to the current step in the process. If along the way, the casualty needs another treatment as part of a larger treatment, the system can set the relevant value to the next step and request that treatment. There can then be a rule that will fire if the value is that next step and the treatment is done. If the treatment is a one-time action and has already been done (or alternatively for repeated treatments was previously done temporally to the current time), the rule will fire immediately and the logic for the treatment will recognize that it has already been done and not start over, for example setting up an IV or administrating fluid resuscitation. In at least one embodiment, the response to a prompt can be a response fact with the value being the button that was selected.

In an alternative embodiment, the message format would be message type followed by a data object.

In a further alternative embodiment, the information received from the external vital-sign monitor is a data stream having discrete segment that include segments to identify the monitor, a timing parameter, and/or a vital sign measurement(s). The handler will be configured to work with a particular segment syntax and convert that to the structure discussed in connection with the table above.

FIGS. 6A-6F illustrate example data flows between an external user interface 652 (which may be replaced by the user interface module 106 and the display 108), an external AI system 654, and an external medical monitor 656 that communicate with the controller 602 through a message listener 6022, which also communicates with the medical knowledge library 120 and its (MK) handler 118. The information flows illustrate the type of information that may flow around and through the system 600. FIG. 6A illustrates a high-level view of the information flows with FIGS. 6B-6F illustrating more detailed information flows for particular components with the controller connected to a system database.

In FIGS. 6A-6F, the illustrated system 600 includes the controller 602, a GUI handler 612, an AI handler 614, a medical knowledge handler 118, and a medical monitor handler 616. These handlers may be the previously discussed handlers. See, e.g., FIGS. 1A-1F. Based on this disclosure, a person having ordinary skill in the art will appreciate that the AI handler 614 may be omitted or multiple ones may be present or at least available to be in communication with external AI systems 654 and, likewise, the medical monitor handler 616 may be omitted or multiple ones may be present or at least available to be in communication with external medical monitors 656. FIG. 6A illustrates the controller 602 as having a message listener 6022, a patient handler 6042, and a patient state 6044, and should be appreciated from this disclosure, the controller 602 may rely on the presence of the database controller 1042 and the local database 1044 of FIGS. 1E and 1F (or the database of FIGS. 1A-1D and 6B) in terms of the patient handler 6042 and patient state 6044. The message listener 6022 receives messages from all of the handlers 118, 612-616 and, in at least one embodiment, communicates with the handlers 118, 612-616 per a routing table 6024 (e.g., FIG. 6B). As illustrated in FIG. 6A, the patient handler 6042 is configured to start a new patient record (if one does not already exist), initialize and update the patient state, and close the patient record once care has finished by the user or alternatively when the user has switched to treating a different patient. The patient handler 6042 acts as the interface between the message listener 6022 and the record as reflected by the patient state 6044. FIG. 6A illustrates an example of a patient state 6044 (or record) that includes a patient record ID; whether the patient has a hemorrhage, an airway obstruction, and/or a tension pneumothorax, and vital signs. In at least one alternative embodiment with a non-inference engine, the facts repository may have a similar data structure to that of the illustrated patient state 6044.

FIGS. 6B-6F illustrate how the information is routed for one patient, but based on this disclosure, a person having ordinary skill in the art should appreciate that multiple patients (or casualties) may be monitored at once. FIG. 6B illustrates how information comes into the controller 602 including an example of a message routing table 6024 based on message type. As discussed previously, the system 600 may have multiple instances of the medical knowledge library 120 running like that illustrated in FIG. 1G, which results in a modified processing of the information by the controller 602 that omits stopping and modifies starting to trigger starting another instance of the medical knowledge library 120 and/or adding a new casualty/individual to the database 104. When multiple instances of the medical knowledge library 120 are running, the controller 102 will track which casualty is being handled by which medical knowledge library instance. In at least one embodiment, when an instance of the medical knowledge library 120 begins, the medical knowledge library 120 requests through the controller 602 a set of information from the system database 104 to provide initial facts for the casualty or the controller 602 as part of the initiation of the medical knowledge library 120 instance retrieves relevant information from the system database 104 to establish initial facts for the casualty, which in the facts repository embodiments provides the starting facts. In a further embodiment, the controller 602 also retrieves current inventory levels from the database 104 to set an inventory fact for each supply item, which can be updated with a new fact as supply items are used in suggested treatments from different medical knowledge libraries 120. FIG. 6C illustrates how the medical monitor handler may interact with the external medical monitor and the controller. Although there are multiple vital-signs being illustrated as being monitored, based on this disclosure, a person of ordinary skill in the art should appreciate a different mix or a subset of vital-signs could be provided by any one medical monitor including multiple medical monitors being attached or, alternatively, omitted with the system receiving the information from the user interface. FIG. 6D illustrates how the AI system handler may interact with the external AI system, which is illustrated as being a risk system such as the APPRAISE system, and the controller. In an alternative embodiment, the AI handler or the medical knowledge library (prior to sending message to the AI handler will request updated heart rate and/or blood pressure if those vital signs are too old. FIG. 6E illustrate how the medical knowledge handler 118 may interact with the medical knowledge library and the controller 602. FIG. 6F illustrates how the UI handler 110, 110A could interact with the external user interface and the controller 602.

FIGS. 7A-8I illustrate a pair of additional examples for how information may flow through the system illustrated, for example, in FIG. 6A taken at different points in time to illustrate how information would flow through the system where the sequence of steps is illustrated by the numbered circles for each time mark and are accompanied by the information moving in that sequence step. The illustrated information flows are also illustrative as to how information may flow through the systems 100 illustrated in FIGS. 1A-1F. As illustrated by the information flows, there may be parallel information flows happening at the same time (as represented by multiples of certain sequence step numbers in particular figures) into and out of the message listener 6202 of the controller 602, which could be part of the decision support (or front end) systems 100A-100C illustrated in FIGS. 1A-1C. Both of these examples are an illustrative use of the described systems with an external user interface, a medical monitor 656 such as an Athena wireless vital-signs monitor, and the APPRAISE system, which provides the hemorrhage risk level, attached as external systems and respective handlers 612, 616, 714. As these are illustrative information flows, these flows may not be medically accurate but are offered to show how information may flow through the system. As time progresses in these examples, the patient state is updated and further instructions are generated by the rules engine 124 of the medical knowledge library 120 in response to new information (i.e., facts). See, e.g., sequence step 5 in FIGS. 7B, 7C, 7E, 8B-8D, 8F; sequence step 9 in FIGS. 7D, 7F, 8G-8I.

Figure 7B:
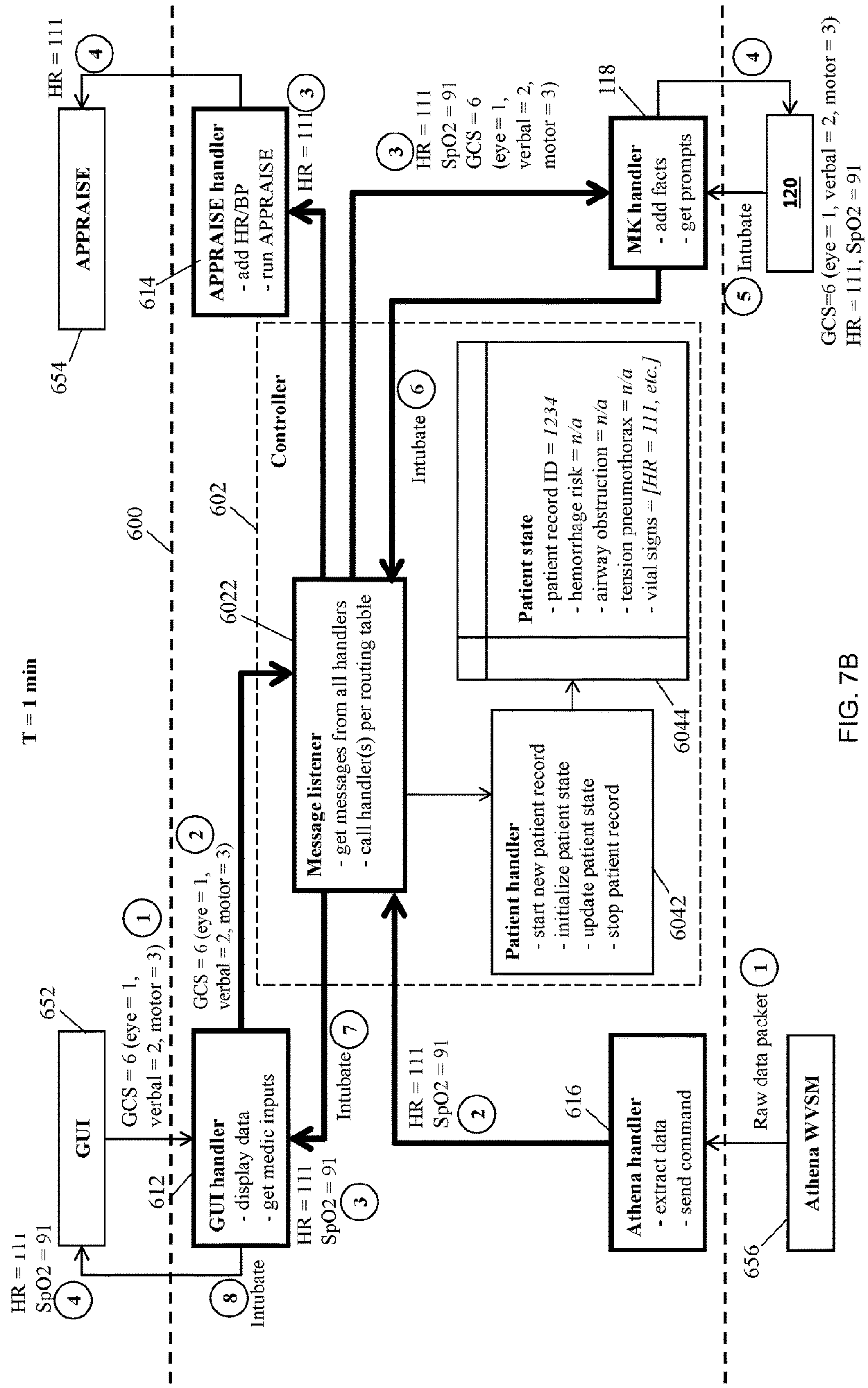
FIG. 7A shows a table with information for a first use case to provide context for data flow diagrams illustrated in FIGS. 7B-7G.
Figure 7C:
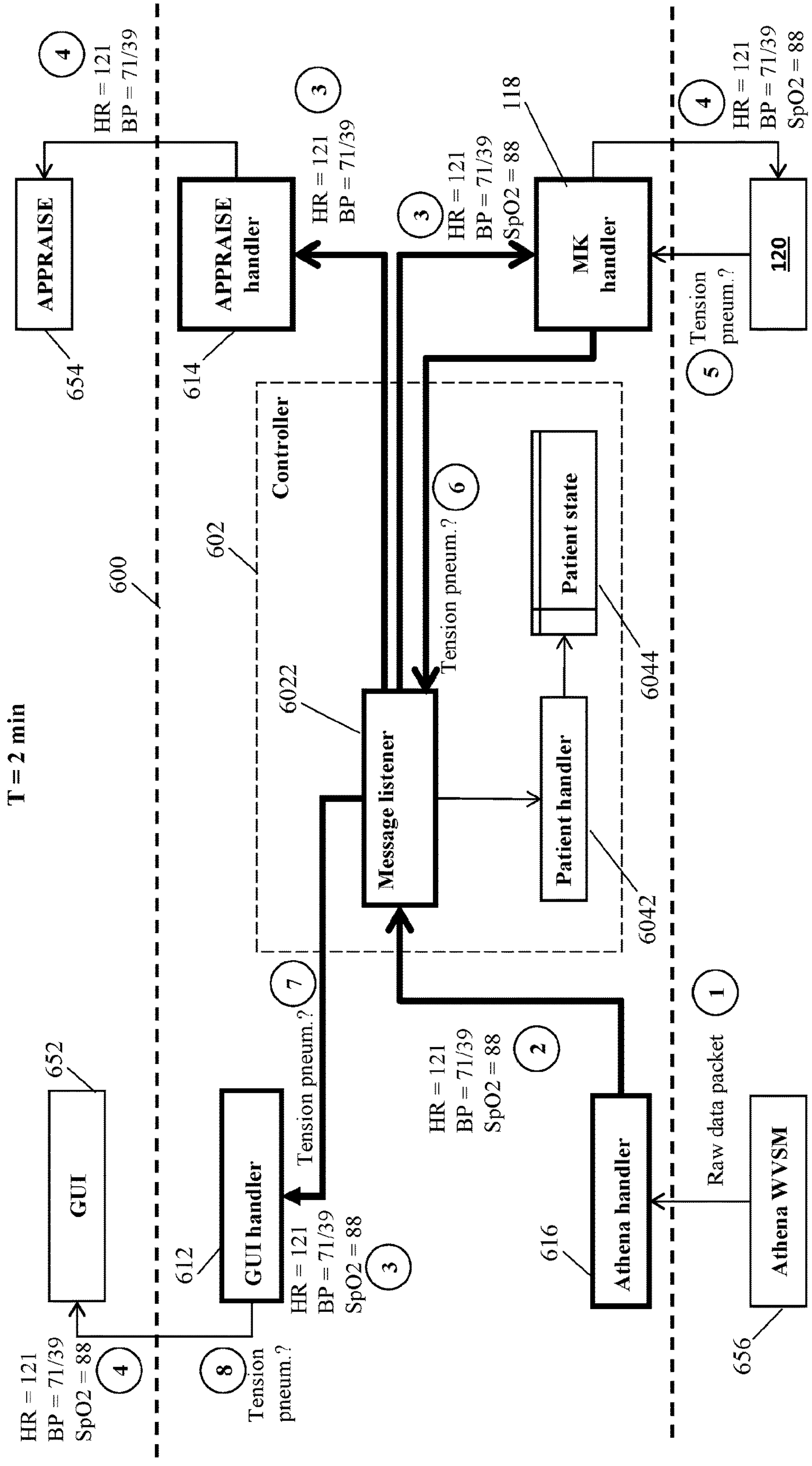
Figure 7D:
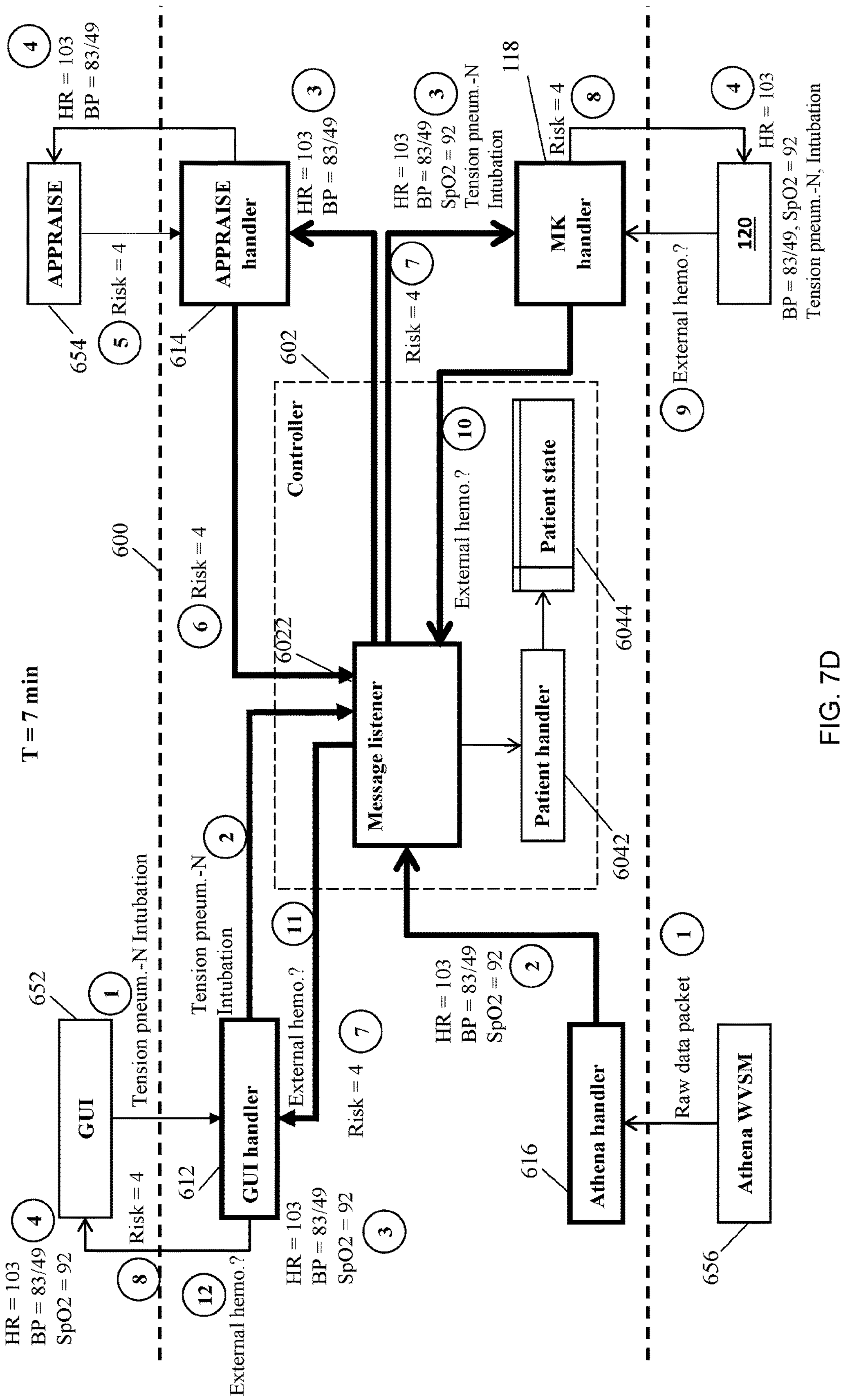
Figure 7E:
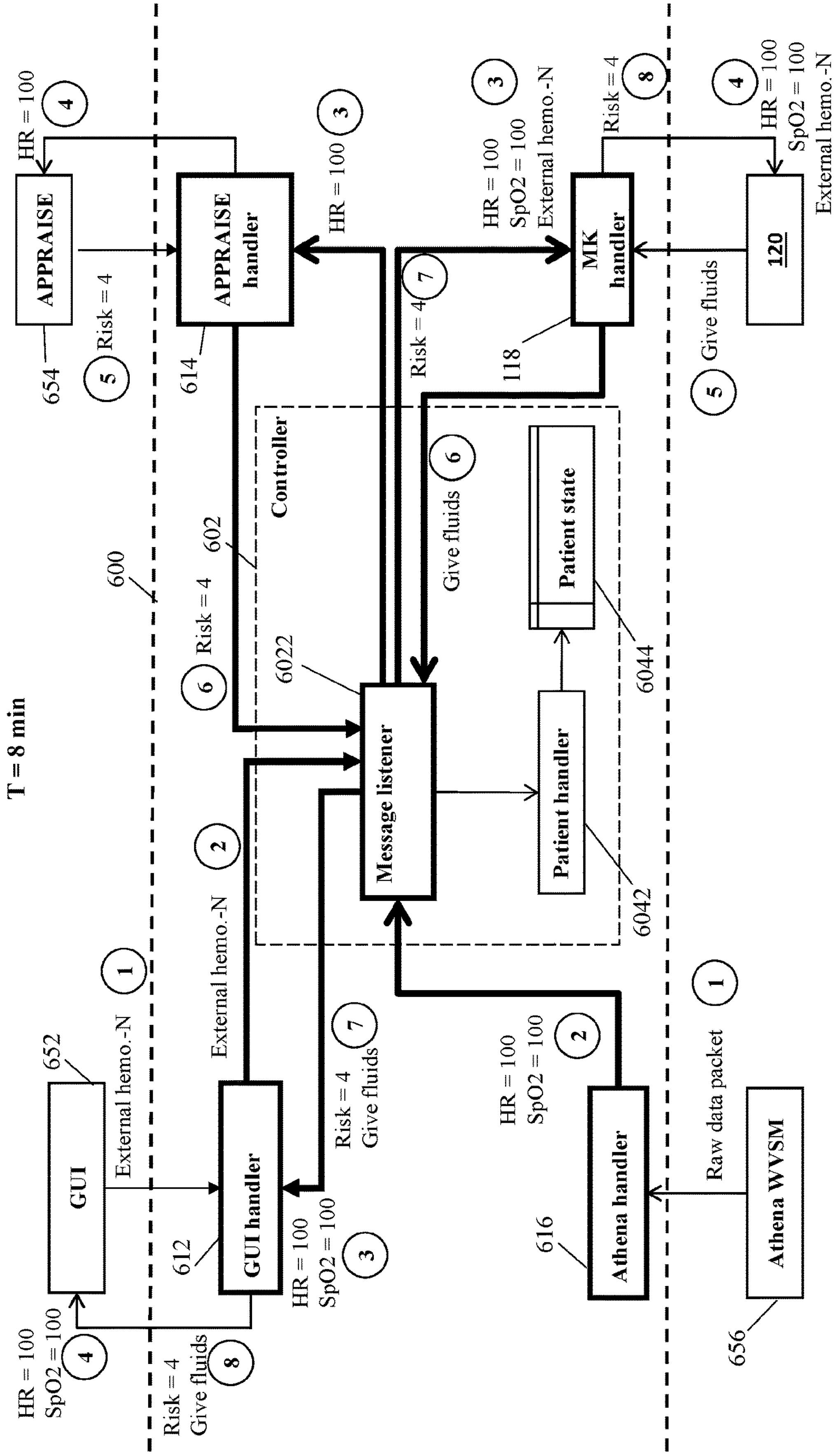
Figure 7F:
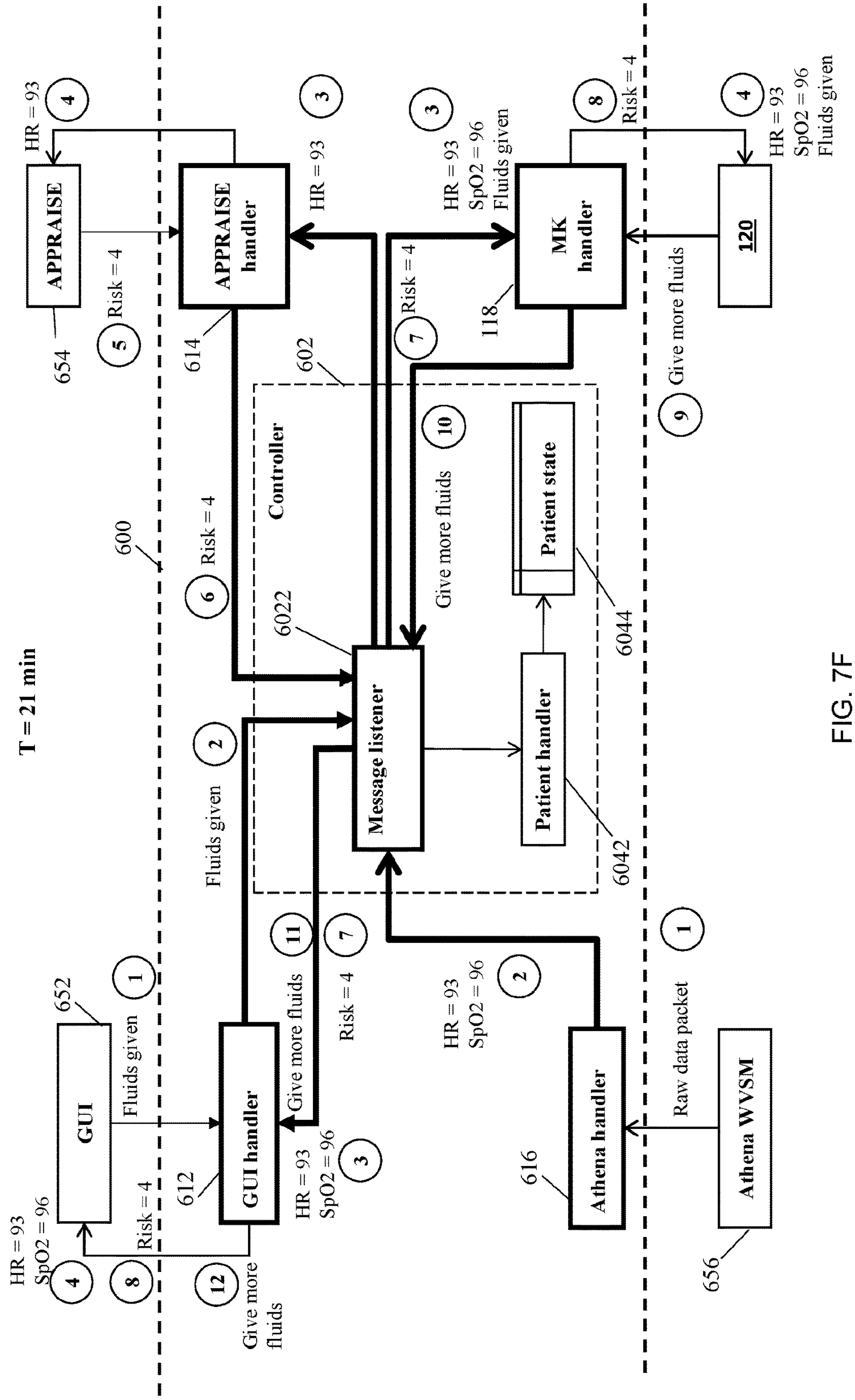
Figure 7G:
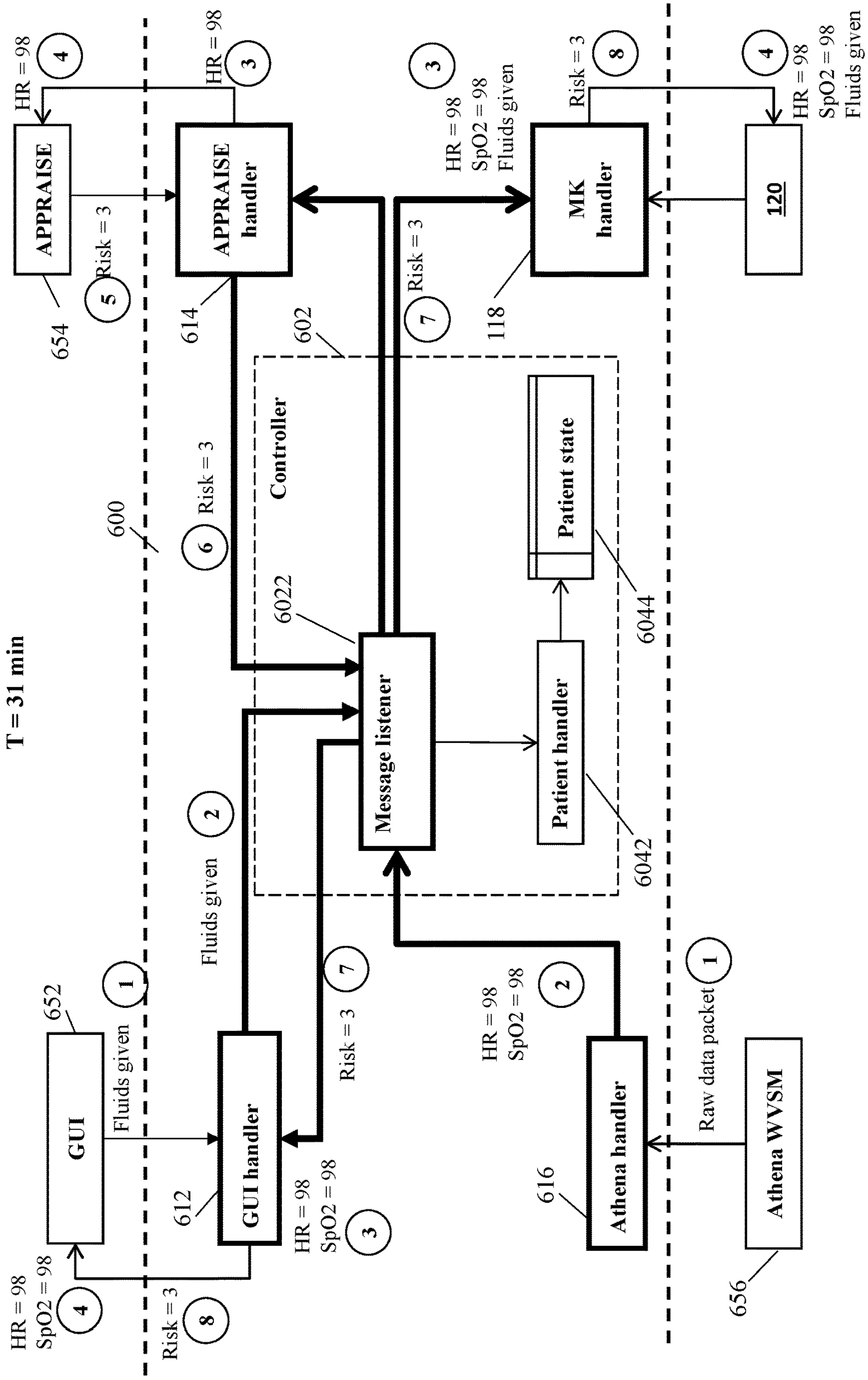

The first illustrative example is a 27 years old, unconscious female. Her Glasgow Coma Scale (GCS) score was a 6 (eye—1, verbal—2, and motor—3). Her internal injuries were sustained from a motor vehicle rollover resulting in a renal laceration grade III and internal injury to unspecified organs without any mention of an open wound into the cavity. Prior to arrival at the hospital, she was intubated and received 1300 cc of Crystalloids. The table shown in FIG. 7A describes the sequence of events with each row showing the events happening and the data flowing at around the time shown in the first column with a vital sign monitor being attached at time 0. The medic response columns include airway obstruction, tension pneumothorax, external hemorrhage, and treatment. The output columns include hemorrhage risk level and rules engine prompt(s). Each of the FIGS. 7B-7G correspond to a respective point in time in the table in FIG. 7A to illustrate how information may be distributed through the system. FIGS. 7B, 7C, 7E, and 7G include information flows with eight sequence steps. FIGS. 7D and 7F include information flows with twelve sequency steps.

Figure 8B:
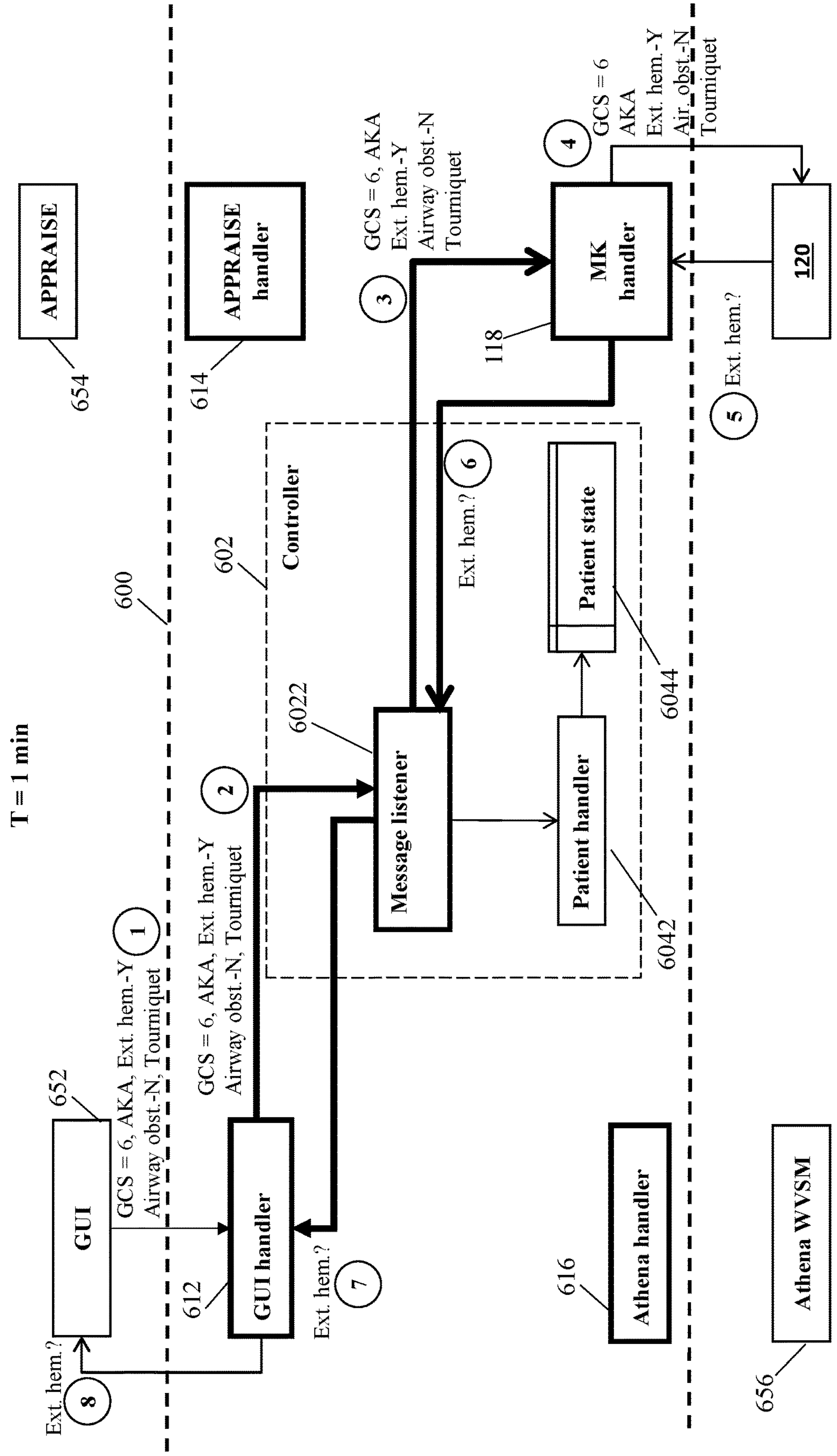
FIG. 8A shows a table with information for a second use case to provide context for data flow diagrams illustrated in FIGS. 8B-8I.
Figure 8C:
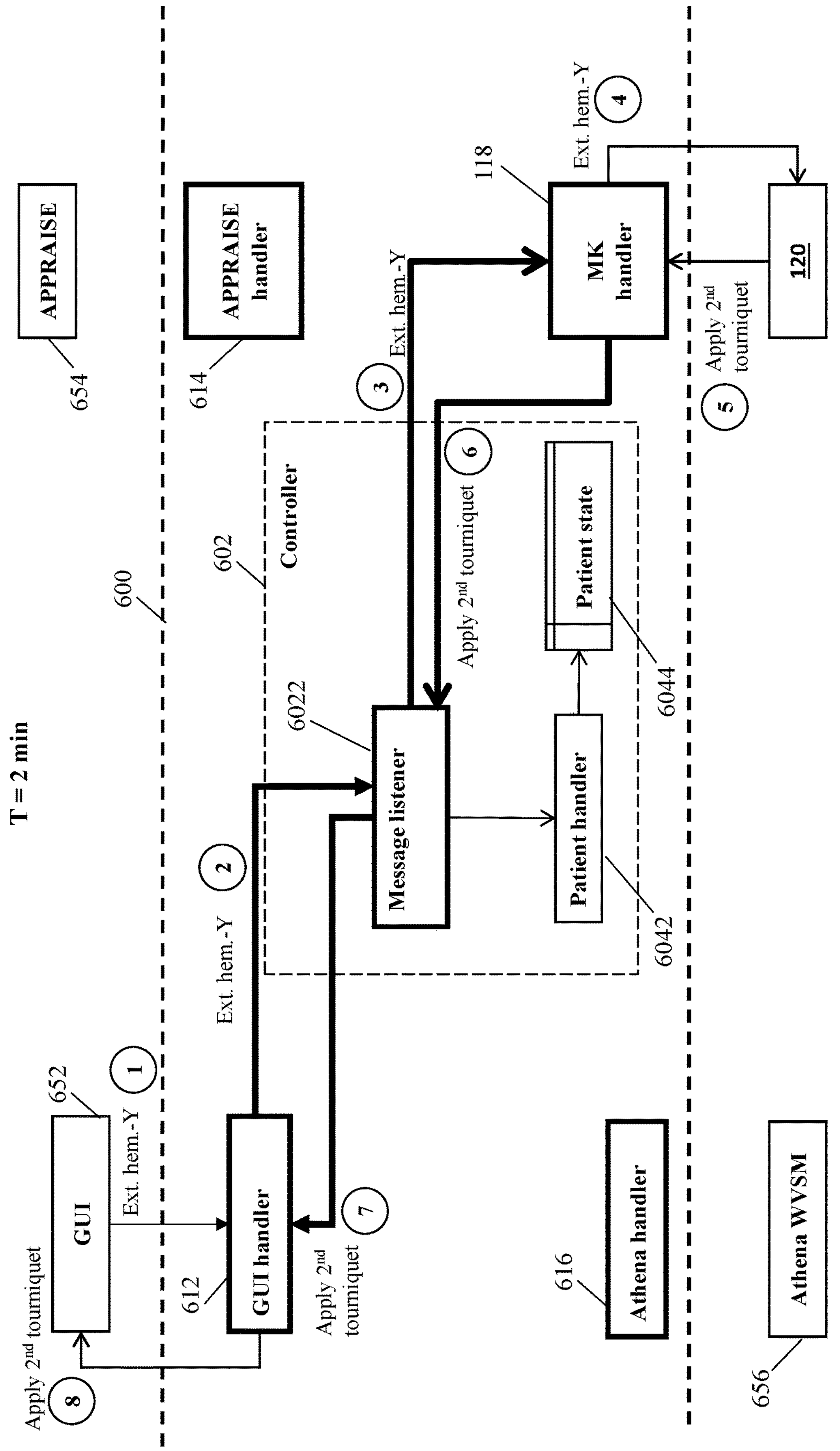
Figure 8D:
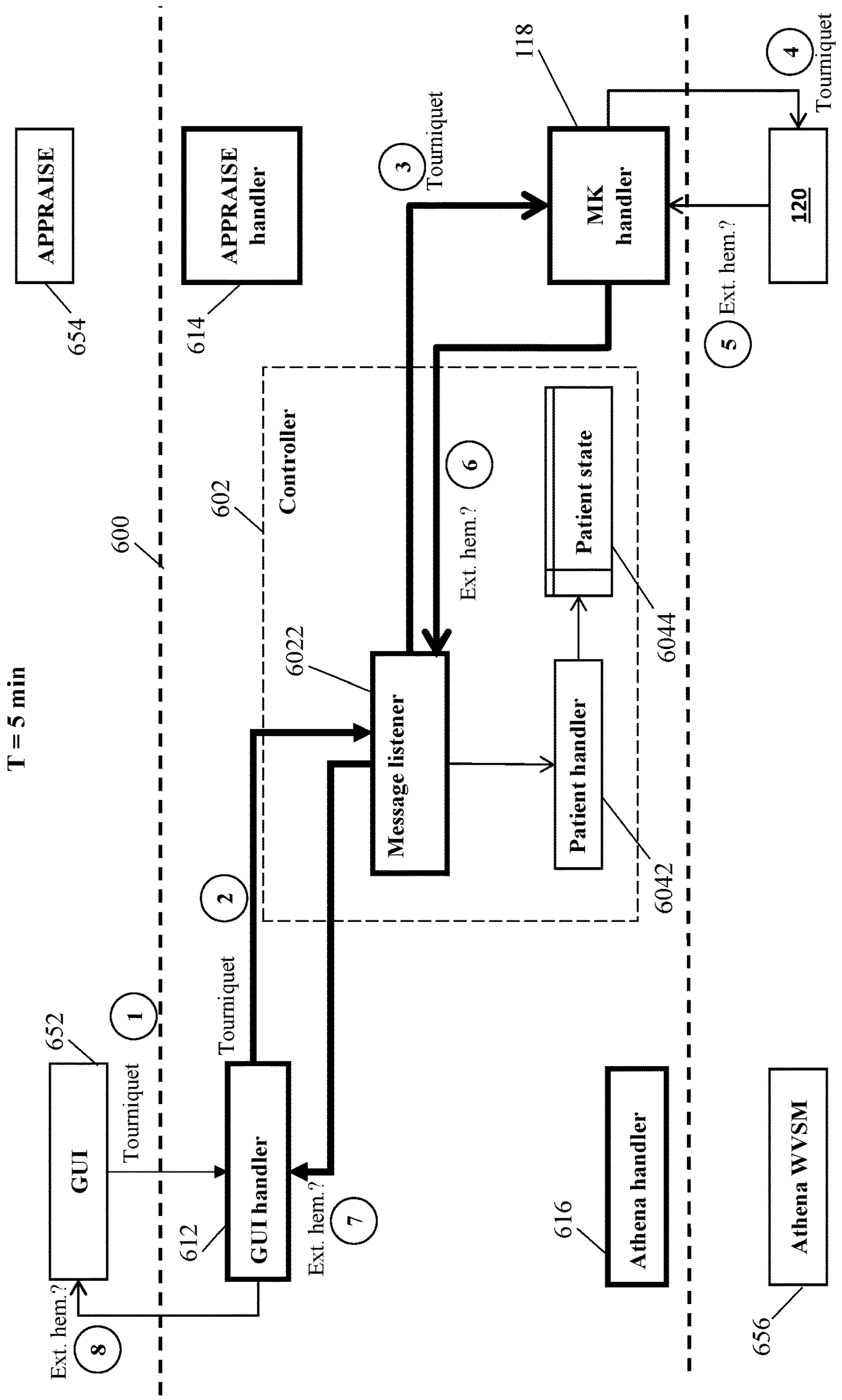
Figure 8E:
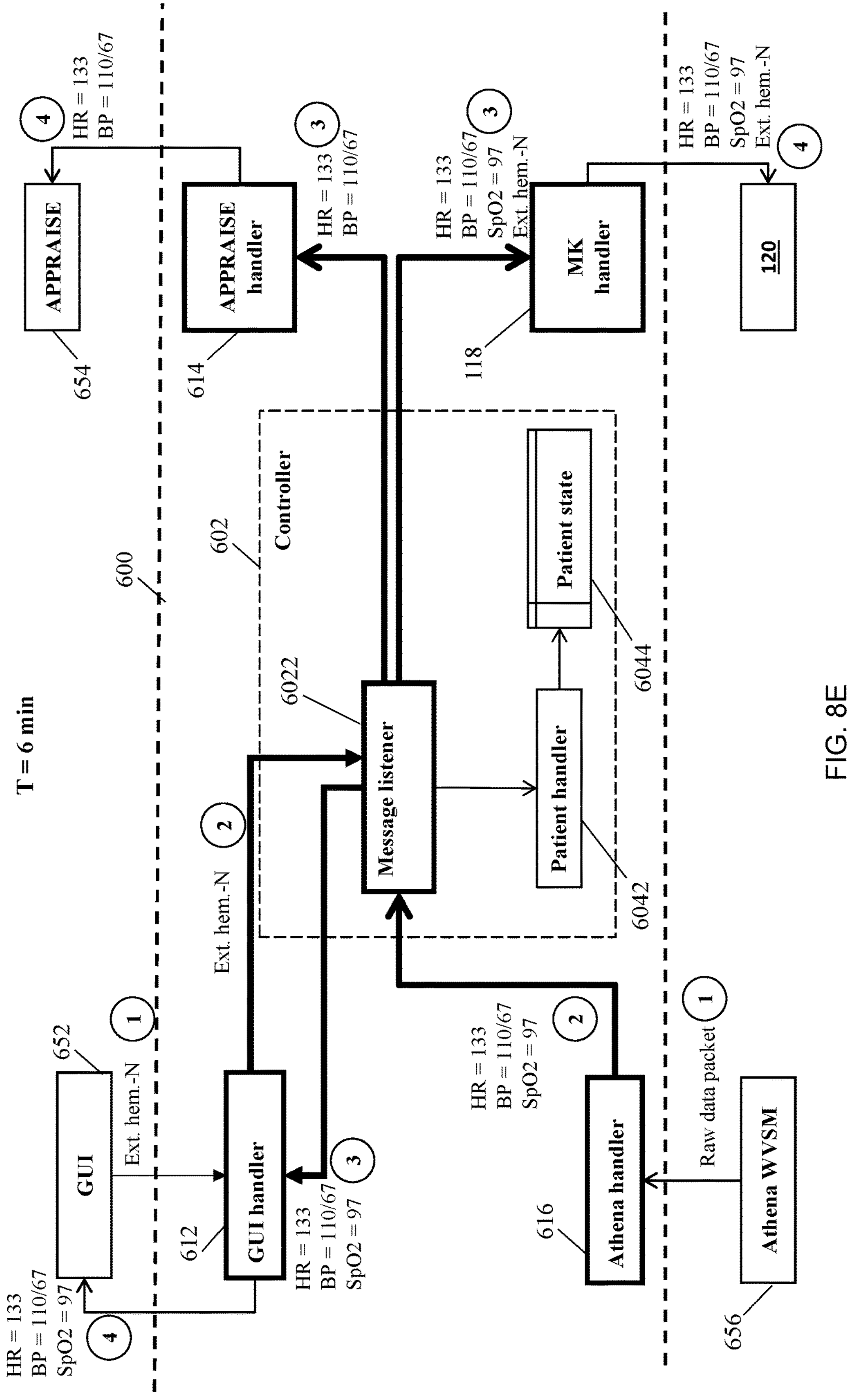
Figure 8F:
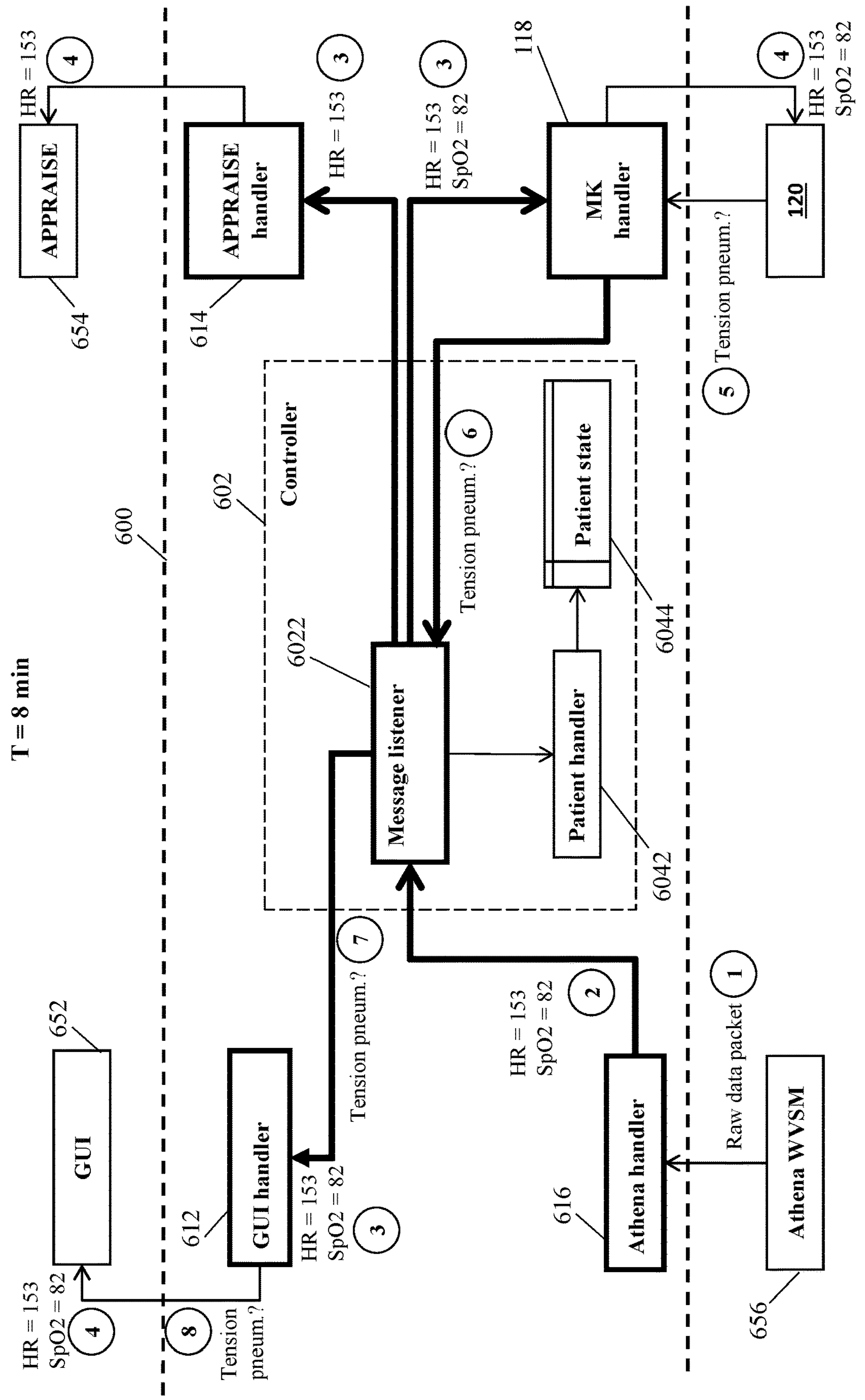
Figure 8G:
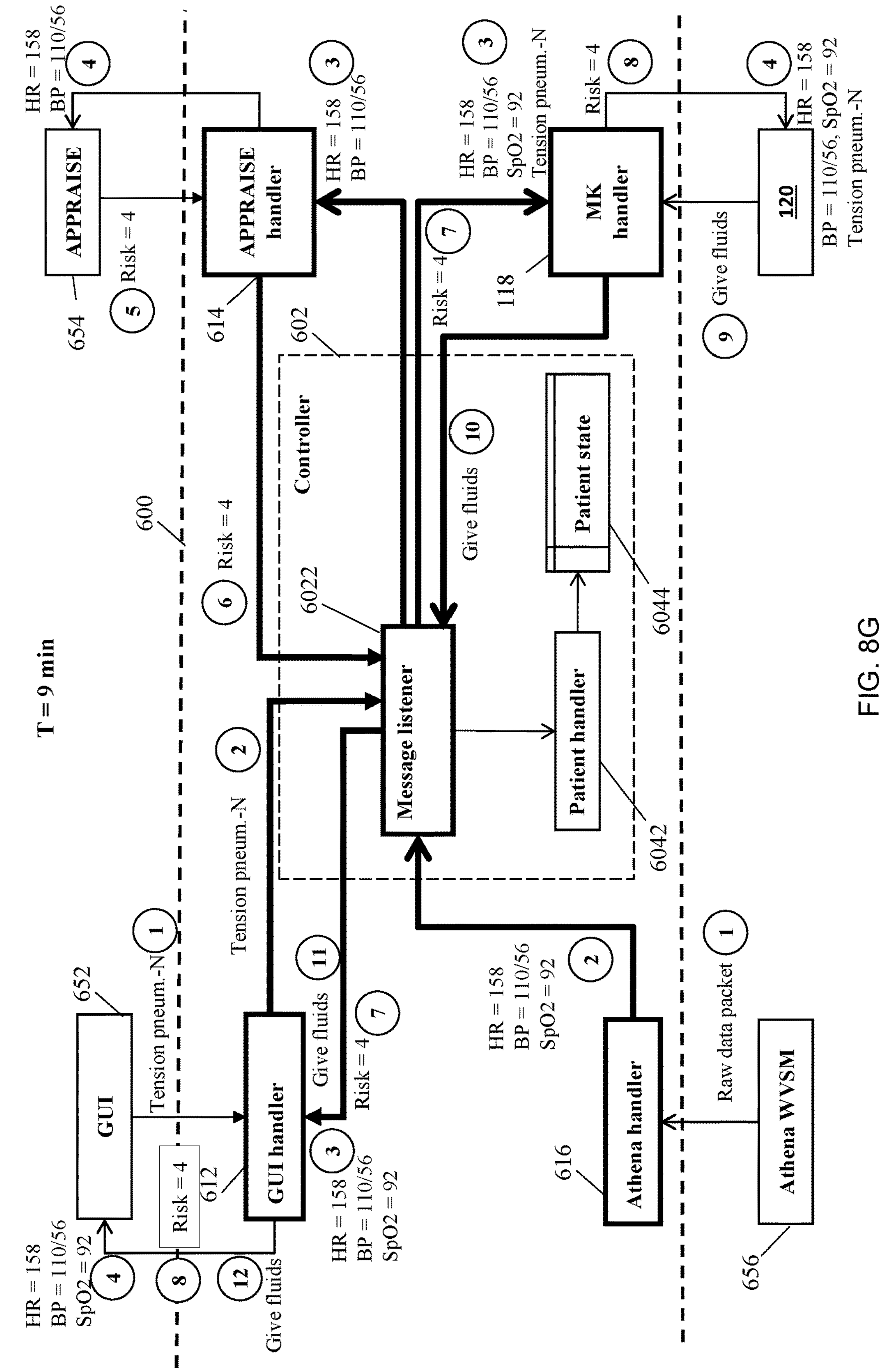
Figure 8H:
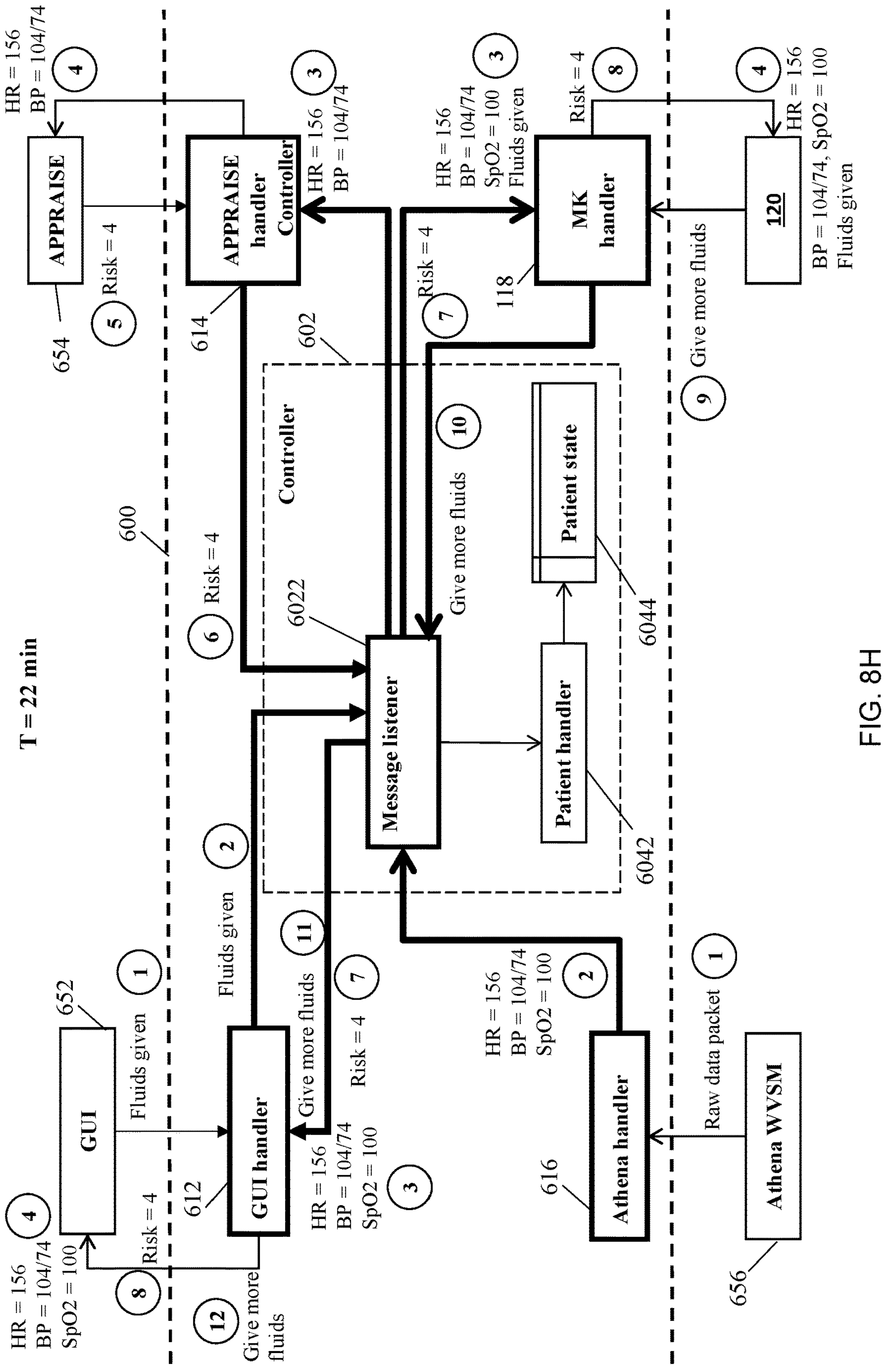
Figure 8I:
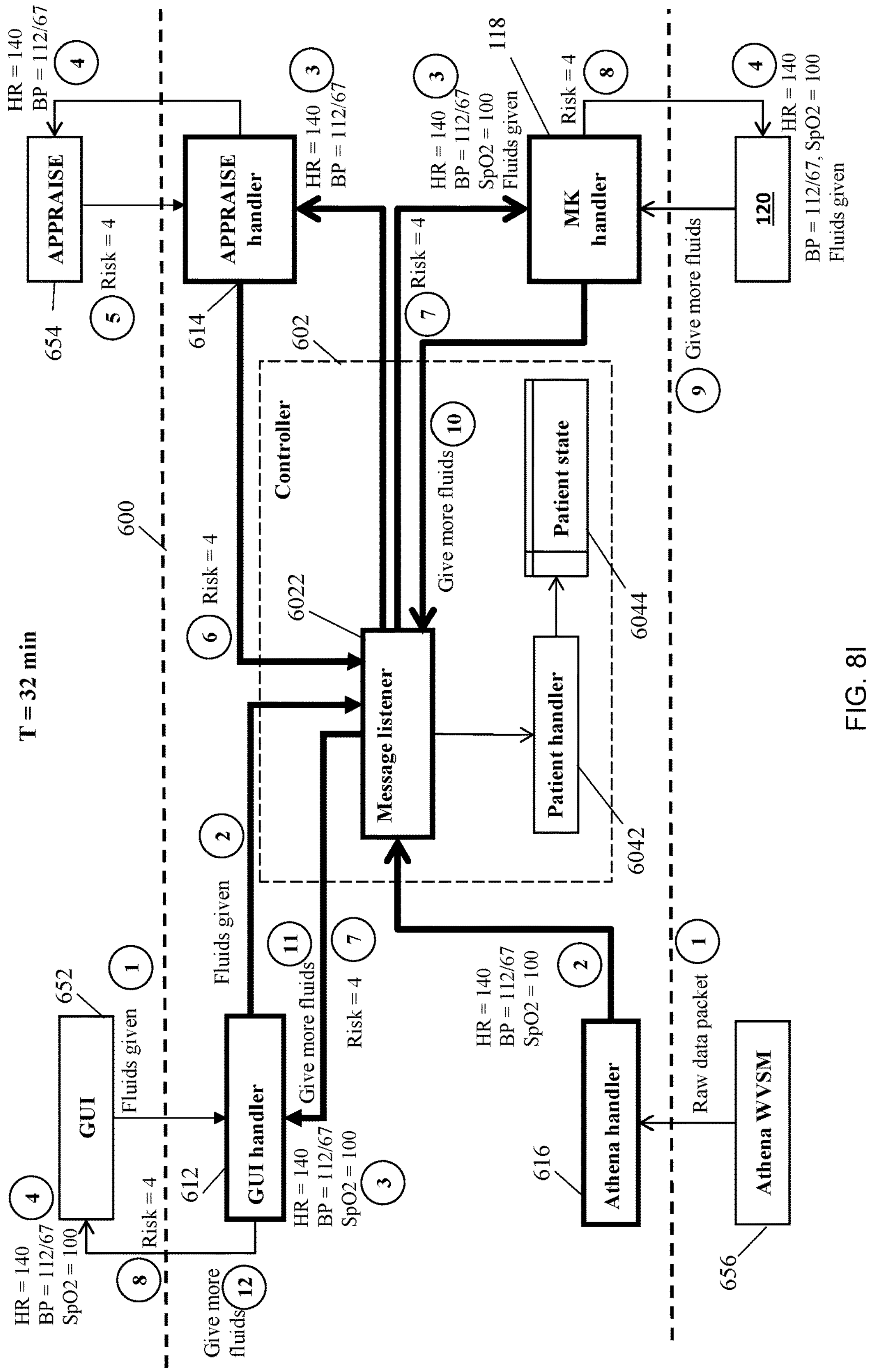

The second example is a 23 years old, conscious male. His GCS score was a 15. He suffered a traumatic above knee amputation after being pinned between two cars. Prior to arrival at the hospital, he received 1700 cc of Crystalloids. The table shown in FIG. 8A describes the sequence of events with each row showing the events happening and the data flowing at around the time shown in the first column with a vital sign monitor being attached at time 5 minutes. The medic response columns include injury, airway obstruction, tension pneumothorax, external hemorrhage, and treatment. The output columns include hemorrhage risk level and rules engine prompt(s). Each of the FIGS. 8B-8I correspond to a respective point in time in the table in FIG. 8A. This illustrative example provides an example of how the vital-signs monitor and the APPRAISE system were not in every data flow at each of the minute marks as represented by no flow lines to and from those components. FIGS. 8B-8D and 8F include information flows with eight sequence steps. FIG. 8E includes an information flow with four sequence steps. FIGS. 8G-8I include information flows with twelve sequence steps.

In a situation when the front end system is not connected to any external monitors or user interfaces, for example as could occur when the group is moving about or has been isolated without such equipment, the main system 100 will still function in at least one embodiment. The user would log into the main system 100 before opening up an existing individual's record in the system database or requesting to create a new casualty record to bring up a user interface on the display. In response to this occurring, the controller 102 will determine whether an instance of the medical knowledge library (or module) 120 is running for the casualty, if an instance does not exist for the casualty starting an instance for the particular casualty and loading the instance with preliminary facts based on any information present in the system database 104 including about the casualty and/or inventory information. In response to receiving a selection through the user interface from the user as to what assessment to perform or injury information in the form of a message to the controller 102, the controller 102 and/or the medical knowledge handler 118 create a fact based on that message for the medical knowledge library 120 to process in the rules engine 124 to generate questions and/or instruction messages to the controller 102 to populate the user interface on a display to receive additional information from the user that will be converted into facts for use by the medical knowledge library 120. As that information about the casualty and/or the treatment of the casualty is received, the controller 102 and/or the medical knowledge handler 118 will generate message(s) containing the information, which in an alternative embodiment are in a fact syntax to the medical knowledge library 120. The controller 102 will also send the information to the system database 104 to be stored in a medical record for the casualty. The medical knowledge library 120 acting upon those messages to generate further assessment questions and/or intervention suggestions to be performed by the user that will be packaged in a message(s) to the controller 102 to present the information in the user interface on the display 108. The user interface receives input from the user in response to the displayed assessment and/or suggested treatment(s) that are sent by the controller 102 (depending on the implementation via the user interface handler). The controller 102 creating a message to the medical knowledge library 120 and the system database 104 to provide this new information. This process will continue until the user switches to a different casualty or is finished with this stage. Although as discussed previously, the medical knowledge library 120 through its control module 122 may set alarms for follow-up action by the user. In an alternative embodiment where the device with the system on it also has the APPRAISE system and/or another AI/ML system, then the information flows may include interactions with these systems similar to what is illustrated in FIGS. 6A and 6D.

Figure 9:
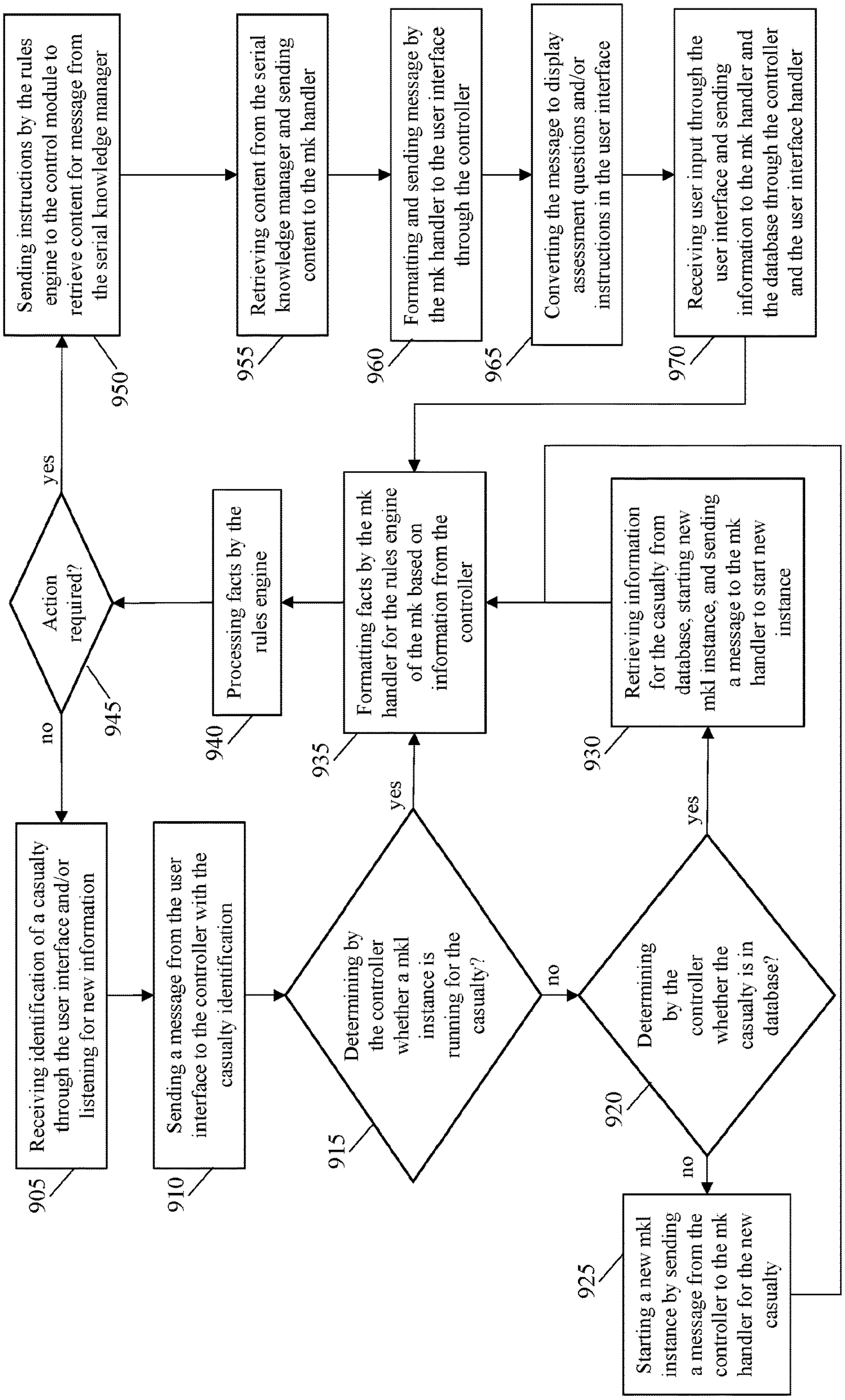
FIG. 9 illustrates information flows according to at least one embodiment without or unconnected external handlers.

FIG. 9 illustrates an information flow for such a situation that includes using multiple instances of the medical knowledge library 120 (e.g., FIG. 1G) by the controller 102 loading (or initiating) a new instance of the medical knowledge library 120 for each casualty being actively monitored by the system. In at least one embodiment, the method begins with receiving identification of a casualty from the user through a user interface and/or listening for new information from any active handlers, 905. The user interface module or active handler sends a message to the controller 102 with the casualty identification or other new information, 910. The controller 102 in response to such a message determines whether that is a medical knowledge library (mkl) instance running for the identified casualty or the casualty associated with the new information, 915. If a medical knowledge library instance is not running for the casualty, then the controller 102 determines whether the casualty is present in the system database 104, 920. If the casualty is not present in the database 104, the controller 102 initiates a new medical knowledge library instance by sending a message to the medical knowledge (mk) handler for the new casualty to start the instance, 925. In a further embodiment, the controller 102 sends a message to the database 104 to create a new casualty record providing any information received regarding the new casualty. If there is an existing record for the casualty in the database 104, the controller 102 retrieves information for the casualty form the database 104 and starts a new medical knowledge library instance by sending a message to the medical knowledge handler 118 to start a new instance with information retrieved from the database 104, 930. The initiation of the medical knowledge library instance can be accomplished as discussed earlier in this disclosure. After the medical knowledge library instance is started or if the instance was already running, the medical knowledge hander formats the information received from the controller 102 into facts for the rules engine 124 to use, 935. The rules engine 124 processes the received facts sent by the medical knowledge handler 118 through the control module 122 of the medical knowledge library 120, 940. Depending on the outcome of the facts processing by the rules engine 124, there is a decision if any action is required, 945. Examples of an action including requesting additional facts or providing suggested treatments. Info action is required, then the method returns to a listening mode at the start of the method. If there is action to be taken, the rules engine 124 sends instructions to the control module 122 to retrieve content for a message to be sent to the medical knowledge handler 118 where the content is obtained from the serial knowledge manager 127, 950. The control module 122 retrieves content from the serial knowledge manager 127 and sends the content in a message to the medical knowledge handler 118, 955. The medical knowledge handler 118 formats the content into a message to send to the user interface through the controller 102, 960. The user interface module or handler converts the message to remove the content to display the assessment questions and/or treatment instructions in the user interface, for example on display 108, 965. Receiving with the user interface module 106 user input that is converted into a message (if not embedded in the interface to trigger upon selection of a button) and sending that message to the controller 102 to send onto the medical knowledge handler 118 and the database 104. The medical knowledge handler 118 formats the information into one or more facts for the medical knowledge library 120, 935.

The present invention may be a system, a method, and/or a computer program product at any possible technical detail level of integration. The computer program product may include a computer readable storage medium (or media) having readable program instructions thereon for causing a processor to carry out aspects of the present invention.

The computer readable storage medium is a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a memory stick, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages and procedural programming languages. The computer readable program instructions may execute entirely on the user's device, partly on the user's device, as a stand-alone software package, partly on the user's device and partly on a remote device or entirely on the remote device. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart/workflow illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus (e.g., Android base device) to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 10:
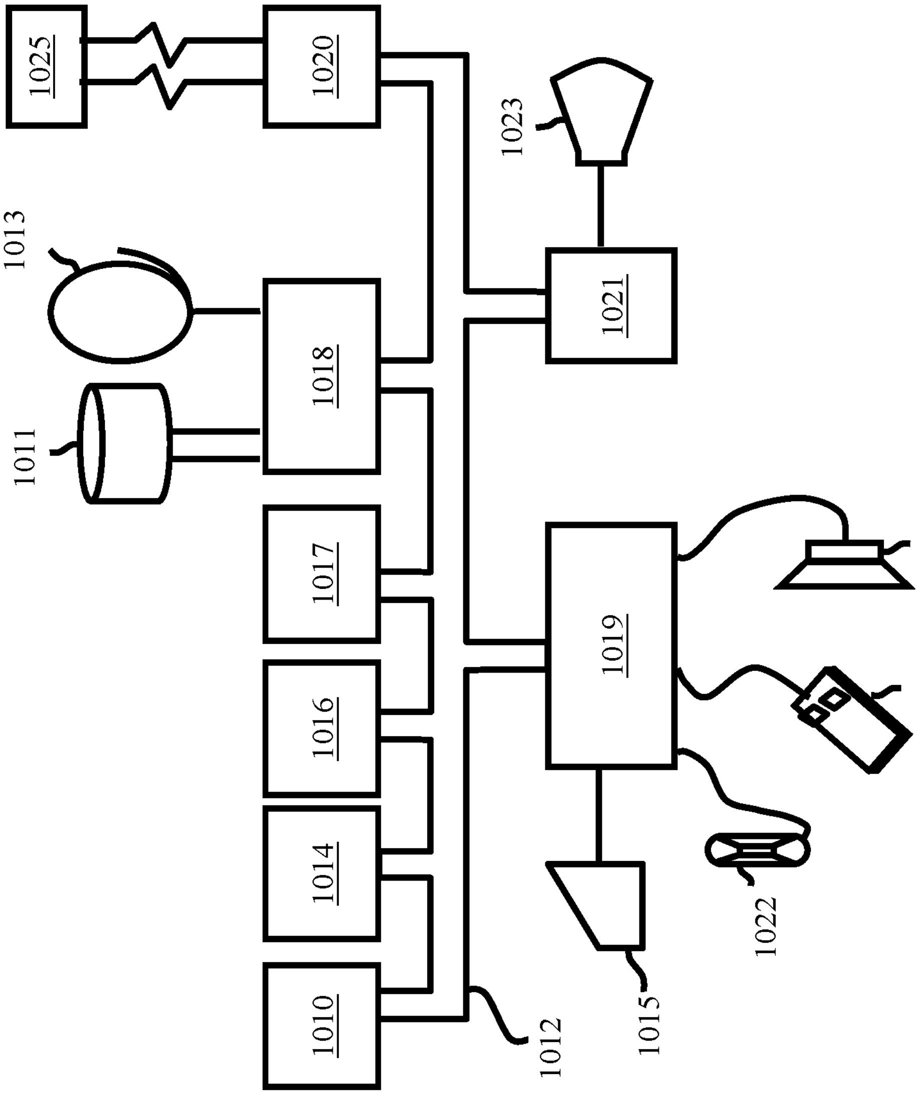
FIG. 10 illustrates a schematic representation of a computer or other processor-based device.

Referring now to FIG. 10, a representative hardware environment for practicing at least one embodiment is illustrated. This figure illustrates a hardware configuration of information handling/computer system components, which in a further embodiment may be representative of a smart phone architecture other than the I/O adapter and some peripheral components, in accordance with at least one embodiment of the invention. The illustrated system includes at least one processor or central processing unit (CPU) 1010 (for simplicity, one CPU is illustrated) configured to run code for the front end system and the medical knowledge library. The CPU(s) 1010 is interconnected with a system bus 1012 to various devices such as a random-access memory (RAM) 1014, a read-only memory (ROM) 1016, an internal non-volatile storage 1017, and an input/output (I/O) adapter 1018. The RAM 1014, the ROM 1016, and the storage 1017 are examples of a memory, which may store the local database and any databases from the rules engine module. The I/O adapter 1018 may connect to peripheral devices, such as disk (or storage) units 1011 and tape drives 1013, or other program storage devices that are readable by the system. The system can read the stored instructions and follow these instructions to execute the methodology of at least one embodiment of the invention. The system further includes a user interface adapter 1019 that connects, for example, to a (virtual) keyboard 1015, a mouse (or virtual cursor) 1017, a speaker 1024, a microphone 1022, and/or other user interface devices such as a touch screen device (not shown) to the bus 1012 to gather user input. Depending on the implementation, what the user interface adapter 10110 connects to may depart from that illustrated. Additionally, a communication adapter 1120 connects the bus 1012 to a data processing network 1025 (e.g., wireless network, cellular network, or broadband connection), and a display adapter 1021 connects the bus 1012 to a display device 1023 which may be built into the system or embodied as an output device such as a monitor, printer, or transmitter, for example. In at least one embodiment, the display device 1023 shows the user interface like those illustrated in FIGS. 2A-5G.

Although the methods discussed in this disclosure are done without reference to particular flowcharts, it should be understood that the order of the steps shown to be varied from the order illustrated in other embodiments, that steps discussed as being separate can be combined (e.g., various displays and request for data can be combined into a single output screen), and that not all steps illustrated are necessarily required in all embodiments. Additionally, in at least one embodiment where the implementation uses a processor, the processor executes code for the steps as such is an example of means for performing the discussed function.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the root terms “include” and/or “have”, when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While a specific embodiment of the invention will be shown and described in detail to illustrate the application of the principles of the invention, it will be understood that the invention may be embodied otherwise without departing from such principles.

In the claims that follow this specification, it should be understood that the invention includes placing the claims into nested (or multiple levels) of multiple dependency form where no conflict exists between dependent claims.

E. FIRST EXAMPLE

A. AIRWAY
B. Tab: 2, Airway
C. Initial Questions:
- Group 1:
  - Priority 2
  - Question: Mechanism of Injury?=Blast/Blunt/Burn/GSW/Trauma/Fall/MVA
- Group 2:
  - Priority 2
  - Question: AVPU?
    - More Information: Choose the first that applies. A=Alert, V=Responds to Voice, P=Responds to Pain, U=Does not Respond
- Group 3:
  - Priority 2
  - Question: Airway Open?
    - More Information: An open airway means that air can flow freely in/out of the lungs without obstruction. A casualty with an obstructed airway will be struggling to move air (think about a person choking). Eventually they will lose consciousness and die if the obstruction is not removed, or a secondary airway placed.
- Group 4:
  - Priority 2.1
  - Question: Type and Location of Facial Injuries? Indicate treatment if already treated.

Location needed on Neck and Face (forehead, R orbit, L orbit, nose, upper jaw, lower jaw, neck, back of head, R ear, L ear)
Options for type: fracture, laceration, penetrating, burn, none
Multiple options for treatment: res pos, head tilt, jaw thrust, npa, ega, cric, none
Options for condition: airway open, airway blocked
NOTE: set burns=false and injuries=false for head and for neck as appropriate based on answers Group 5:
Priority 2.2
Question: Trauma to Cervical Spine?

Group 6:
Priority 2.2
Question: Burns to Chest?
Condition: Only ask if burns to face=false and burns to neck=false Group 7:
Priority 2.21
Condition: Do not ask if burns to face=true, burns to neck=true, or burns to chest=true
Question: Inhalation Injury?
More Info: known exposure to fire, smoke or fumes, soot around face and mouth, coughing D. Follow On Questions:

E. After Intervention Questions:

Group 1:
Priority: 2
Question: Airway Open?
More Info: air moving freely from nose and/or mouth F. Rules:

1. IF: Airway Open=TRUE (and airway was not previously closed)
AND: AVPU=A
AND: Trauma to cervical spine=FALSE
AND: Neck trauma=FALSE
AND: Facial trauma=FALSE
AND: Burns to face=FALSE
AND: Burns to neck=FALSE
AND: Burns to chest=FALSE
AND: Inhalation Injury=FALSE
THEN: Go to Respiration
2. IF Burns to Neck=TRUE
OR: Burns to Face=TRUE
OR: Burns to Chest=TRUE
THEN inhalation injury=true
3. IF MOI=blast or fall
AND injury to face
THEN facial trauma=true
4. IF facial trauma=true
THEN head trauma=true
5. IF MOI=blast or fall
AND injury to neck
THEN trauma to neck=true G. Follow up Rules:

1. IF: Placed in Rescue Position=applied
THEN: ask after intervention question group 1
2. IF: Head Tilt=applied
THEN: ask after intervention question group 1
3. IF: Jaw Thrust=applied
THEN: ask after intervention question group 1
4. IF: Extraglottic airway=applied
THEN: ask after intervention question group 1
5. IF: NPA=applied
THEN: ask after intervention question group 1
6. IF: Endotracheal intubation=applied
THEN: ask after intervention question group 1
7. IF: Initial cervical spine stabilization=applied
THEN: ask after intervention question group 1
8. IF: remove cervical spine stabilization=applied
THEN: ask after intervention question group 1

F. SECOND EXAMPLE

```
(defmodule HEMORRHAGE (import MAIN ?ALL))
(defrule HEMORRHAGE :: massive-external-extremity-hemorrhage
   ?condition <- (condition (name external-hemorrhage) (value yes) (location ?location))
   (not (exists (treatment (name extremity-tourniquet))))
   (test (neq (is-extremity ?location) FALSE))
=>
   (modify ?condition (value wait))
   (assert (procedure (name amenable-to-tourniquet) (location ?location)
   (assert (priority (name priority) (value 1)))
   (assert (activity))
)
(defrule HEMORRHAGE::massive-external-extremity-hemorrhage2
   ?condition <- (condition (name external-hemorrhage) (value yes) (location ?location))
   (treatment (name extremity-tourniquet) (location ?tournlocation))
   (test (neq (is-extremity ?location) FALSE))
   (test (neq ?location ?tournlocation))
=>
   (modify ?condition (value wait))
   (assert (procedure (name amenable-to-tourniquet) (location ?location)))
   (assert (priority (name priority) (value 1)))
   (assert (activity))
)
(defrule HEMORRHAGE::massive-external-junctional-hemorrhage
   ?condition <- (condition (name external-hemorrhage) (value yes) (location ?location))
   (not (exists (treatment (name junctional-tourniquet))))
   (test (neq (is-junctional ?location) FALSE))
=>
   (modify ?condition (value wait))
   (assert (procedure (name amenable-to-junctional-tourniquet) (location ?location)))
   (assert (priority (name priority) (value 1)))
   (assert (activity))
)
```

-continued

```
(defrule HEMORRHAGE::massive-external-junctional-hemorrhage2
   ?condition <– (condition (name external-hemorrhage) (value yes) (location ?location))
   (treatment (name junctional-tourniquet) (location ?tournlocation))
   (test (neq (is-junctional ?location) FALSE))
   (test (neq ?location ?tournlocation))
=>
   (modify ?condition (value wait))
   (assert (procedure (name amenable-to-junctional-tourniquet) (location ?location)))
   (assert (priority (name priority) (value 1)))
   (assert (activity))
)
(defrule HEMORRHAGE::pressure-dressing-apply
   ?condition <– (condition (name external-hemorrhage) (value wait) (location ?location))
   (treatment (name extremity-tourniquet) (value notamenable) (location ?tournlocation))
=>
   (retract ?condition)
   (assert (condition (name compressible-external-hemorrhage) (value yes) (location ?location)
)
(defrule HEMORRHAGE::extremity-tourniquet-apply
   (condition (name external-hemorrhage) (value wait) (location ?location))
   ?treatment <– (treatment (name extremity-tourniquet) (value amenable) (location ?tournlocation))
   (test (neq (is-extremity ?location) FALSE))
   (test (eq ?location ?tournlocation))
=>
   (modify ?treatment (value apply))
)
(defrule HEMORRHAGE::extremity-tourniquet-apply-ask
   (treatment (name extremity-tourniquet) (value apply) (location ?tournlocation))
   (not (exists (inventory (name extremity-tourniquet)))
=>
   (assert (procedure (name ask-extremity-tourniquets)))
)
```

G. THIRD EXAMPLE

```
<?xml version=“1.0” encoding=“utf-8”?>
<procedures>
   <procedure index=“1”>
      <name>airway-question</name>
      <steps>
         <step index=“1”>
            <questions>
               <question>
                  <conditionQuestion>(find-fact ((?f condition)) (eq ?f:name airway))</conditionQuestion>
                  <questionText>Is Airway open ?</question Text>
                  <optiions>
                     <option Yes value=“Yes”>(condition (name airway) (value unobstructed))
                     </option Yes>
                     <optionNo value=“No”>(condition (name airway) (value obstructed))</optionNo>
                  </optiions>
               </question>
            </questions>
         </step>
      </steps>
   <procedure index=“3”>
      <name>airway-closed-questions</name>
      <steps>
         <step index=“1”>
            <questions>
               <question>
                  <conditionQuestion>(find-fact ((?f condition)) (eq ?f:name conscious))</conditionQuestion>
                  <questionText>Is Casualty Conscious ?</question Text>
                  <optiions>
                     <optionYes value=“Yes”>(condition (name conscious) (value yes))
                     </optionYes>
                     <optionNo value=“No”>(condition (name conscious) (value no))</optionNo>
                  </optiions>
               </question>
               <question>
                  <conditionQuestion>(find-fact ((?f condition)) (eq ?f:name alert))</conditionQuestion>
                  <questionText>Is Casualty Alert ?</question Text>
                  <optiions>
                     <optionYes value=“Yes”>(condition (name alert) (value yes))</optionYes>
                     <optionNo value=“No”>(condition (name alert) (value no))</optionNo>
                  </options>
```

-continued

```
          </question>
          <question>
            <conditionQuestion>(find-fact ((?f condition)) (eq ?f:name verbal))</conditionQuestion>
            <questionText>Is Casualty Responding to Verbal Stimuli ?</questionText>
            <optiions>
              <optionYes value="Yes">(condition (name verbal) (value yes))</optionYes>
              <optionNo value="No">(condition (name verbal) (value no))</optionNo>
            </options>
          </question>
          <question>
            <conditionQuestion>(find-fact ((?f condition)) (eq ?f:name pain))</conditionQuestion>
            <questionText>Is Casualty Responding to Pain Stimuli ?</questionText>
            <optiions>
              <optionYes value="Yes">(condition (name pain) (value yes))</optionYes>
              <optionNo value="No">(condition (name pain) (value no))</optionNo>
            </optiions>
          </question>
          <question>
            <conditionQuestion>(find-fact ((?f injury)) (eq ?f:name trauma) (eq ?f:location
cervical))</conditionQuestion>
            <questionText>Evidence of Trauma to the neck/cervical spine ?</question Text>
            <optiions>
              <optionYes
                value="Yes">(injury (name trauma) (value yes) (location cervical))
              </optionYes>
              <optionNo
                value="No">(injury (name trauma) (value no) (location cervical))
              </optionNo>
            </optiions>
          </question>
          <question>
            <conditionQuestion>(find-fact ((?f injury)) (eq ?f:name trauma) (eq ?f:location
face))</conditionQuestion>
            <questionText>Evidence of facial trauma ?</questionText>
            <optiions>
              <optionYes
                value="Yes">(injury (name trauma) (value yes) (location face))
              </optionYes>
              <optionNo value="No">(injury (name trauma) (value no) (location face))
              </optionNo>
            </optiions>
          </question>
          <question>
            <conditionQuestion>(find-fact ((?f injury)) (eq ?f:name burn) (eq ?f:location
face))</conditionQuestion>
            <questionText>Evidence of burns to face/neck/chest ?</question Text>
            <optiions>
              <optionYes value="Yes">(injury (name burn) (value yes) (location face))
              </optionYes>
              <optionNo value="No">(injury (name burn) (value no) (location face))
              </optionNo>
            </optiions>
          </question>
          <question>
            <conditionQuestion>(find-fact ((?f injury)) (eq ?f:name inhalation)</conditionQuestion>
            <questionText>Evidence of Smoke Inhalation Injury ?</question Text>
            <optiions>
              <optionYes value="Yes">(injury (name inhalation) (value yes))
              </optionYes>
              <optionNo value="No">(injury (name inhalation) (value no))</optionNo>
            </optiions>
          </question>
        </questions>
      </step>
    </steps>
  </procedure>
  <procedure index="4">
    <name>head-tilt-procedure</name>
    <steps>
      <step index="1">
        <textBlock>
          <text>Place one hand on forehead.</text>
        </textBlock>
```

-continued

```
      </step>
      <step index="2">
        <textBlock>
          <text>Tuck fingers of the other hand under the chin.</text>
        </textBlock>
      </step>
      <step index="">
        <textBlock>
          <text>Tilt head backwards while pressing down on the chin and opening airway.</text>
          <photo>
            <photoname>HEADTILT1.png</photoname>
          </photo>
        </textBlock>
      </step>
      <step index="4">
        <textBlock>
          <text>Visually inspect mouth area to check for occlusion .< /text>
        </textBlock>
      </step>
      <step index="5">
        <textBlock>
          <text>Look down the chest to look for rise and fall of the chest.</text>
          <photo>
            <photoname>HEADTILT2.png</photoname>
          </photo>
        </textBlock>
      </step>
      <step index="6">
        <textBlock>
          <text>Feel for breathing against your cheek.</text>
        </textBlock>
      </step>
      <step index="7">
        <textBlock>
          <text>Once airway is open in unconscious casualty place NPA.</text>
        </textBlock>
      </step>
      <step index="8">
        <textBlock>
          <text>Roll into recovery position if you cannot stay with the casualty.</text>
        </textBlock>
      </step>
    </steps>
  </procedure>
      <step index="8">
```

H. FOURTH EXAMPLE

A. Procedure
1. Put on Gloves
2. Obtain supplies
3. Identify insertion site on injured side (Mid-clavicular OR Axillary)
   a. 2nd Intercostal Space Mid-Clavicular Line: annotated image
   b. Locate middle of clavicle annotated image
   c. Move finger down over first and second rib to intercostal space annotated image
   d. Insertion will be just above third rib annotated image
   e. Insertion must be done between nipple line and shoulder annotated image
   f. OR 5th Intercostal Space Anterior Axillary Line: annotated image
   g. Follow anterior axillary line to just lateral and below nipple annotated image
4. Prepare for insertion
   a. Prepare area with antiseptic solution
   b. Select 10 or 14 gauge, 3% inch long needle
   c. Remove luer lock cap from needle catheter, if applicable
5. Insert needle at 90-degree angle, perpendicular to casualty's chest annotated image
   a. Insert just over top of rib
   b. Insert needle and catheter to hub annotated image
   c. Leave in place 5-10 seconds to allow for decompression annotated image
   d. Remove needle leaving catheter in place annotated image
6. Secure catheter hub to chest
7. Reassess for successful placement
   a. Respiratory distress improves
   b. Hissing sound is heard (may be difficult to hear)
   c. Sat Increases to >90 annotated image
   d. Casualty with no VS has returned to consciousness
   e. Radial pulse now present
   f. annotated image

What is claimed is:

1. A medical decision support system comprising:

at least one handler configured to communicate with a respective non-system device;

a medical knowledge library having a control module, a rules engine configured to use information received by said control module and a facts repository configured to store facts for one or more casualties, at least one reference database containing step-by-step instructions, images, videos, and/or assessment questions;

a serial knowledge manager in communication with said control module and configured to receive instructions from said rules engine through said control module to retrieve information based on content from said at least one reference database and to output retrieved information to said control module, and a system database configured to store at least casualty information, a controller in communication with said at least one handler, said medical knowledge library, and said system database, said controller configured to route information between said at least one handler, said medical knowledge library, and said system database based on present routing information identifying what types of information to route to which part of said decision support system.

2. The medical decision support system according to claim 1, wherein said medical knowledge library or said at least one handler further includes a medical knowledge handler configured to convert information received from said controller into facts for use by said rules engine and to receive instructions from said control module to send to said controller.

3. The medical decision support system according to claim 1, wherein said at least one reference database of said medical knowledge library includes an instructions database storing the step-by-step instructions, images and videos, and an assessments database storing the assessment questions.

4. The medical decision support system according to claim 3, wherein the step-by-step instructions and the assessment questions are stored as xml or html files;

the step-by-step instructions are structured to allow a user of the support system to drill down from a high level to a more detailed level to match requests received from the user, or a high level to a more detailed level to match requests received from the user for additional details;

the step-by-step instructions including at least one prompt reflecting completion of each step of the instructions, wherein completion of the high-level instructions will result in marking of the sub-steps in the same manner, or a completion button to select once the instructions are completed by the user;

each assessment question includes a prompt for an answer; and said medical knowledge library or a medical knowledge handler configured to convert the responses to the prompts into facts.

5. The medical decision support system according to claim 3, wherein the assessment questions and/or instructions have embedded within them one or more conditional facts to be sent from a user interface through said controller to said medical knowledge library based on user input received by the user interface satisfying the condition, the decision support system further comprising a medical knowledge handler configured to convert the conditional fact sent from the user interface into a message with information for storage in said database and controller configured to send the message to other handlers listening for that message type, and said serial knowledge manager configured to check whether the fact being sought by the conditional fact is already known based on contents of said facts repository and, further, the fact is temporally relevant and/or close in time, when the fact is known, not sending the assessment question.

6. The medical decision support system according to claim 1, further comprising a display in communications with said controller and configured to receive instructions from the controller to display a user interface.

7. The medical decision support system according to claim 1, wherein said at least one handler includes a vital-signs handler configured to facilitate communication between said controller and an external medical monitor capable of providing vital-sign measurements, and/or a second vital-signs handler configured to facilitate communication between said controller and another external medical monitor capable of providing vital-sign measurements, and/or an analysis handler configured to facilitate communication between said controller and an external artificial intelligence and/or machine learning system.

8. The medical decision support system according to claim 1, wherein said controller or said database includes a message listener routing table containing routing information for each type of message passed to said controller, and/or said system database includes a database controller in communication with said controller and a local database, said controller configured to send all received data to said database controller for storage in said local database with a timestamp.

9. The medical decision support system according to claim 1, wherein said medical knowledge library includes an API in communication with said control module and said controller.

10. A system for providing prolonged casualty care, the system comprising a medical support system:

at least one handler configured to communicate with a respective non-system device;

a database configured to store at least casualty information, a controller in communication with said at least one handler and said database, said controller configured to route information between said at least one handler and said database based on present routing information identifying what types of information to route to which part of said support system; and a medical knowledge library having a control module in communication with said controller, a rules engine with a facts repository, said rules engine connected to said control module, a serial knowledge manager in communication with said control module and configured to receive instructions from said control module, and at least one reference database containing intervention instructions and/or assessment questions; and wherein said at least one handler includes a medical knowledge handler configured to convert information received from said controller into facts to be sent to said control module, and said medical knowledge handler further configured to receive instructions from said control module to send to said controller.

11. The system according to claim 10, wherein said at least one reference database of said medical knowledge library includes an instructions database storing the intervention instructions including text, images and/or videos, and an assessments database storing the assessment questions.

12. The system according to claim 11, wherein the intervention instructions and the assessment questions are stored as xml or html files, the intervention instructions are structured to allow a user of the system to drill down from a high level to a more detailed level to match requests received from the user for additional details, the intervention instructions including at least one prompt reflecting completion of each step of the instruction or a completion button to select once the instructions are completed by the user, wherein completion of the high-level instructions will result in marking of the sub-steps in the same manner, and each assessment question includes a prompt for an answer, and said medical knowledge handler is configured to convert the responses to the prompts into facts.

13. The system according to claim 10, further comprising a display in communications with said controller and configured to receive instructions from the controller to display a user interface.

14. The system according to claim 10, wherein said at least one handler includes a vital-signs handler configured to facilitate communication between said controller and an external medical monitor capable of providing vital-sign measurements, and/or a second vital-signs handler configured to facilitate communication between said controller and another external medical monitor capable of providing vital-sign measurements, and/or an analysis handler configured to facilitate communication between said controller and an external artificial intelligence and/or machine learning system.

15. The system according to claim 10, wherein said controller or said database includes a message listener routing table containing routing information for each type of message passed to said controller, and/or said database includes a database controller in communication with said controller and a local database, said controller configured to send all received data to said database controller for storage in said local database with a timestamp.

* * * * *